US011617787B2

(12) United States Patent
Steinmetz et al.

(10) Patent No.: US 11,617,787 B2
(45) Date of Patent: *Apr. 4, 2023

(54) CANCER IMMUNOTHERAPY USING VIRUS PARTICLES

(71) Applicant: CASE WESTERN RESERVE UNIVERSITY, Cleveland, OH (US)

(72) Inventors: Nicole F. Steinmetz, Cleveland, OH (US); Amy M. Wen, Cleveland, OH (US); Steven Fiering, Hanover, NH (US); Patrick H. Lizotte, Hanover, NH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 641 days.

This patent is subject to a terminal disclaimer.

(21) Appl. No.: 16/612,214

(22) PCT Filed: May 8, 2018

(86) PCT No.: PCT/US2018/031661
§ 371 (c)(1),
(2) Date: Nov. 8, 2019

(87) PCT Pub. No.: WO2018/208828
PCT Pub. Date: Nov. 15, 2018

(65) Prior Publication Data
US 2021/0085777 A1 Mar. 25, 2021

Related U.S. Application Data

(63) Continuation-in-part of application No. 15/589,677, filed on May 8, 2017, now Pat. No. 10,639,363, which is a continuation-in-part of application No. PCT/US2015/059675, filed on Nov. 9, 2015.

(60) Provisional application No. 62/364,997, filed on Jul. 21, 2016, provisional application No. 62/159,389, filed on May 11, 2015, provisional application No. 62/107,617, filed on Jan. 26, 2015.

(51) Int. Cl.
| | | |
|---|---|---|
| A61K 39/12 | (2006.01) |
| A61K 41/00 | (2020.01) |
| A61P 35/04 | (2006.01) |
| A61N 5/10 | (2006.01) |
| A61N 2/00 | (2006.01) |
| A61B 18/02 | (2006.01) |
| A61B 18/12 | (2006.01) |
| A61K 39/00 | (2006.01) |
| A61B 18/00 | (2006.01) |

(52) U.S. Cl.
CPC .............. *A61K 39/12* (2013.01); *A61B 18/02* (2013.01); *A61B 18/12* (2013.01); *A61K 41/0052* (2013.01); *A61N 2/002* (2013.01); *A61N 5/10* (2013.01); *A61P 35/04* (2018.01); *A61B 2018/00577* (2013.01); *A61K 2039/5258* (2013.01); *A61K 2039/585* (2013.01); *A61N 2005/1098* (2013.01)

(58) Field of Classification Search
CPC ........... C12N 2770/18011; C12N 2770/18023; C12N 2770/18032; C12N 2770/18034; A61K 2039/54; A61K 2039/544; A61K 2039/585

See application file for complete search history.

(56) References Cited

U.S. PATENT DOCUMENTS

| | | |
|---|---|---|
| 2007/0248617 A1 | 10/2007 | Bachmann et al. |
| 2007/0284545 A1 | 12/2007 | Isacsson et al. |
| 2015/0033418 A1 | 1/2015 | Lommel et al. |
| 2015/0265696 A1 | 9/2015 | Gourapura et al. |

FOREIGN PATENT DOCUMENTS

| | | |
|---|---|---|
| JP | 2009524699 A | 7/2009 |
| WO | 01/18199 A1 | 9/2002 |
| WO | 2013181557 A1 | 12/2013 |
| WO | 2014059021 A1 | 4/2014 |
| WO | 2015/188110 A1 | 12/2015 |
| WO | 2016019393 A1 | 2/2016 |
| WO | 2016/073972 A1 | 5/2016 |
| WO | 2016/149264 A1 | 9/2016 |
| WO | 2017/004123 A1 | 1/2017 |

OTHER PUBLICATIONS

Applicant: Case Western Reserve University; "Cancer Immunotherapy Using Virus Particles"; European Patent Application No. 18764856.3 for Supplementary European Search Report dated Dec. 22, 2020; 8 pgs.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Nicole F.Steinmetz; "Viral Nanoparticle Multimers"; U.S. Appl. No. 14/761,444, filed Jul. 16, 2015; Final Office Action dated Mar. 11, 2021; 11 pgs.
Office action for Chinese Patent Application No. 201580063662.6, dated Mar. 4, 2020.
Office action for European Patent Application No. 15 857 504.3-1111, dated Mar. 18, 2020.
Yildiz et al., "Applications of viral nanoparticles in medicine", Current Opinion in Biotechnology, vol. 22, Issue 6, pp. 901-908.
Attaluri, et al., "Magnetic nanoparticle hyperthermia enhances radiation therapy: A study in mouse models of human prostate cancer", Int J Hyperthermia Jun. 2015 ; 31(4): 359-374.

(Continued)

*Primary Examiner* — Karen A. Canella
(74) *Attorney, Agent, or Firm* — Tarolli, Sundheim, Covell & Tummino LLP

(57) ABSTRACT

A method of treating cancer in a subject that includes administering in situ to the cancer a therapeutically effective amount of a plant virus or virus-like particle to the subject.

17 Claims, 39 Drawing Sheets

(56) References Cited

OTHER PUBLICATIONS

Chauhan, et al., "Solubility Enhancement of Poorly Water Soluble Molecules using Dendrimers", 2007; vol. 2; No. 1 pp. 1-5.
Setaro, et al., "Generation-dependent templated self-assembly of biohybrid protein nanoparticles around photosensitizer dendrimers", Feb. 11, 2015, Abstract.
Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.
Applicant: Case Western Reserve University; "Cancer Immunotherapy Using Virus Particles"; European Patent Application No. 21201960.8; Extended European Search Report dated Jan. 19, 2022; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Gonzalez Maria Jet Al: "Interaction of Cowpea Mosaic Virus (CPMV) Nanoparticles with Antigen Presenting Cells In Vitro and In Vivo", PLOS One, vol. 4, No. 11, Nov. 2009 (Nov. 2009), XP002780311, ISSN: 1932-6203.
Patrick h. lizotte: "Novel approaches to targeting innate immunity for cancer immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Saunders Ket Al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
Office action for Japanese Patent Application No. 2017-524349, dated Jan. 31, 2020.
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Sheen et al., "Stimulating Antitumor Immunity with Nanoparticles", Wiley Interdiscip Rev Nanomed Nanobiotechnol, Oct. 2014, vol. 6, pp. 496-505.
"CWRU researcher to turn plant virus shells against human cancers", The Daily, CWRU Researcher to Turn Plant Virus Shells Against Human Cancers. Case Western Reserve University, Apr. 18, 2016.
Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.
Applicant: Case Western Reserve University; "Cancer Immunotherapy Using Virus Particles"; Canadian Office Action, dated Aug. 4, 2020; 3 pgs.
Applicant: Case Western Reserve University; "Plant Virus Particles for Delivery of Antimitotic Agents"; Extended European Search Report; dated Aug. 25, 2020; 11 pgs.
Canan Uluog, et al.: "Intermediate dose of methotrexate toxicity in non-Hodgkin lymphoma", General Pharmacology, vol. 32, 1999, pp. 215-218, XP55711259.

Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.
European Search Report for Patent Application No. 15857504.3-1111/3215520, dated May 7, 2018.
Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
International Search Report for Application No. PCT/US15/59675 (2016).
Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.
Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.
Lee et al. "Biodegradable Viral Nanoparticle/Polymer Implants Prepared via Melt-Processing", ACS Nano ePub Sep. 13, 2017 vol. 11 No. 9 pp. 8777-8780.
Lee et al., "PEGylation to Improve Protein Stability During Melt Processing", Macromol Biosci 1-43, 57-75, Oct. 2015 vol. 15 No. 10 pp. 1332-1337.
Lizotte, et al., "Plant-derived viral-like nanoparticle immunotherapy suppress development of metastatic lung cancer", Journal of Immunology, vol. 194, Issue 1 Supplement, May 2015; 4 pgs.
Matsuura et al. Self-assembly of Ni-NT A-modified [3-annulus peptides into artificial viral capsids and encapsulation of His-tagged proteins. Org Biomol. Chem., 2016, 14, 7869 DOI: 10.1039/c6ob01227b (Year: 2016).
Nicole F. Steinmetz; U.S. Appl. No. 16/347503, filed May 3, 2019; NonFinal Rejection dated Jun. 15, 2022; 36 pgs.
Nicole F. Steinmetz; U.S. Appl. No. 16/614676, filed Nov. 18, 2019; NonFinal Rejection dated Jun. 3, 2022; 28 pgs.
Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Ptchova et al. Expression of Human papillomavirus 16 E7ggg oncoprotein on N- and C-terminus of Potato virus X coat protein in bacterial and plant cells. Protein Expression and Purification 77 (2011); p. 146-152.
Smyth etal. Treatment of rapidly growing K-Balb and CT26 mouse tumours using Semliki Forest virus and its derived vector. Gene Therapy (2005) 12, 147-159.
Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.
Wen et al. Design of virus-based nanomaterials for medicine, biotechnology, and energy. Chem. Soc. Rev., 2016, 45, 4074. DOI: 10.1039/c5cs00287g (Year: 2016).
Chinese Patent Appl. No. 201580063662.6; Chinese Office Action; dated May 5, 2022; 3 pgs.

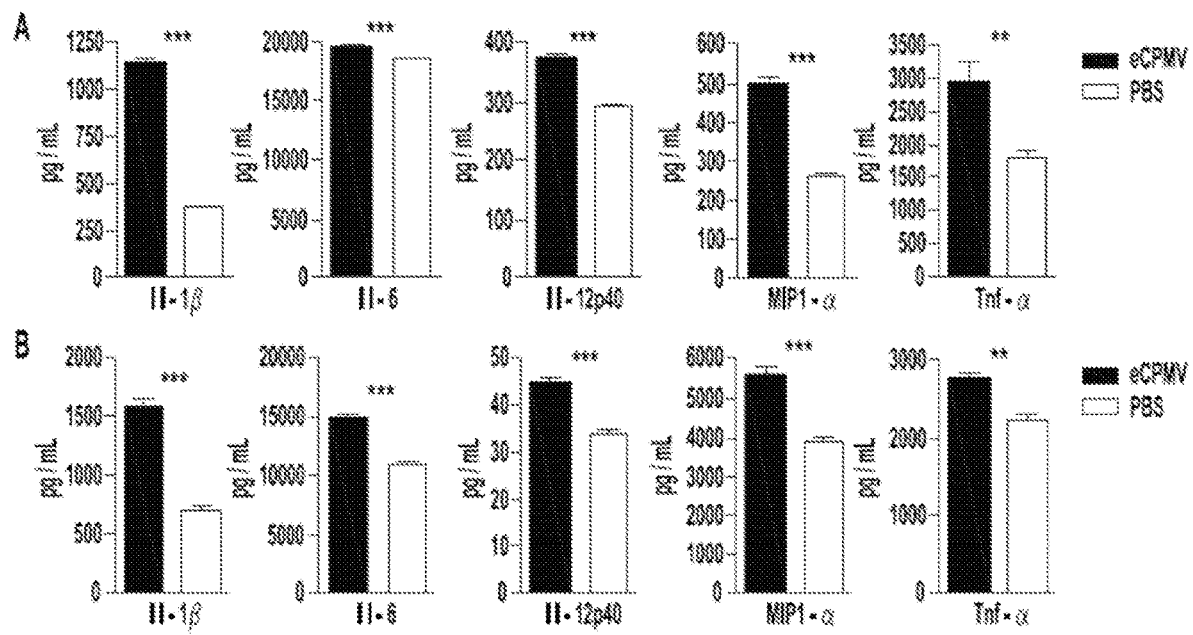
Figs. 1A-B
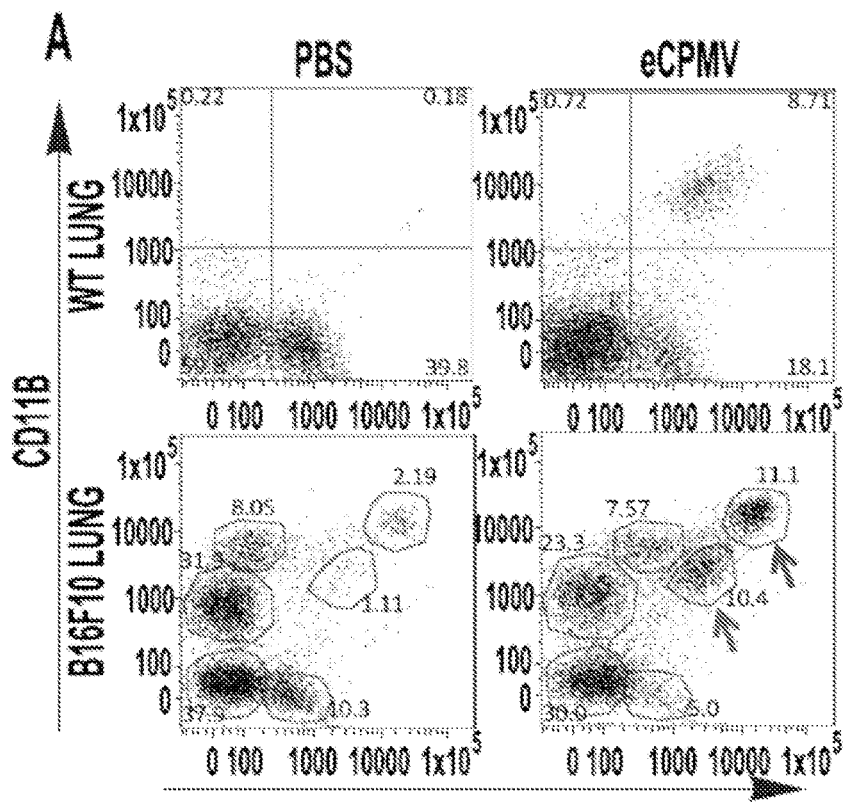
Fig. 2A

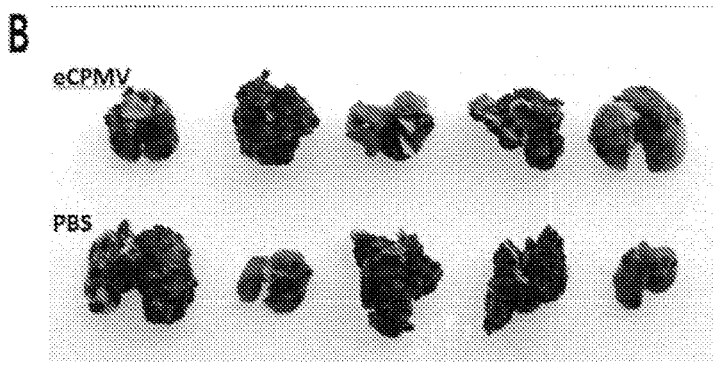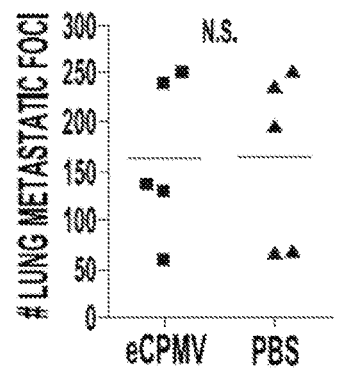
Fig. 4B
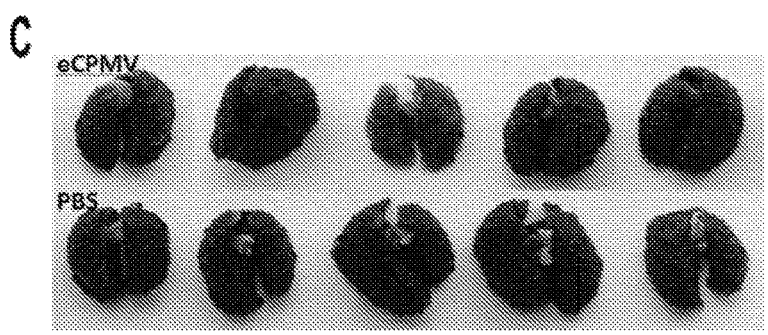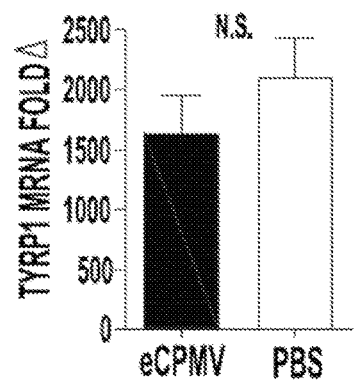
Fig. 4C
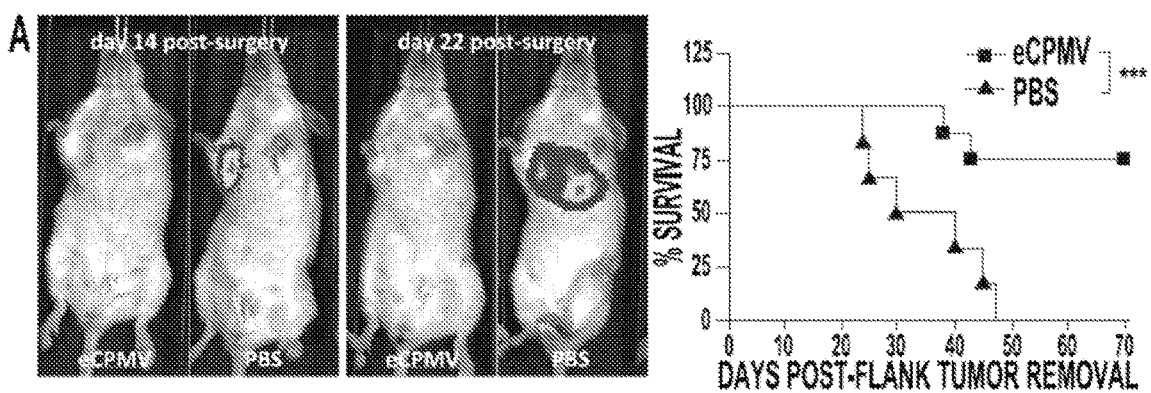
Fig. 5A

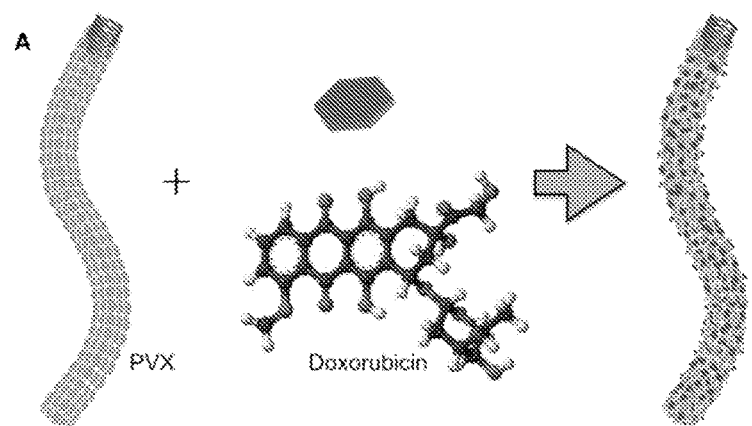
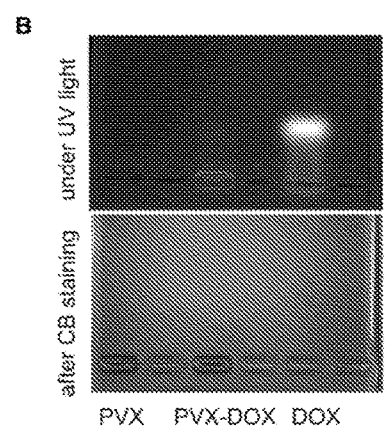
Fig. 8A
Fig. 8B
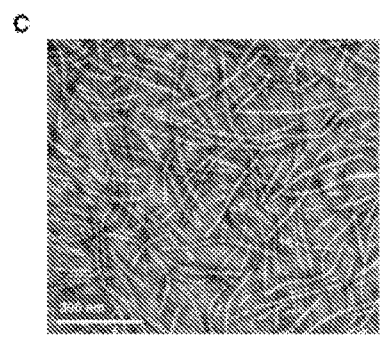
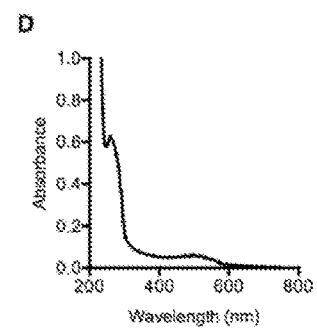
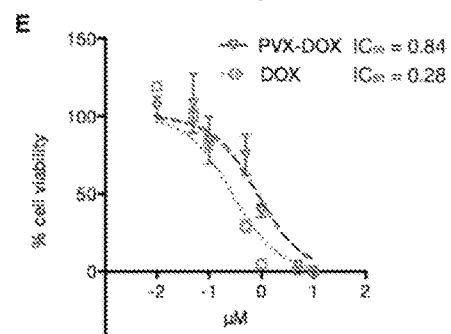
Fig. 8C
Fig. 8D
Fig. 8E

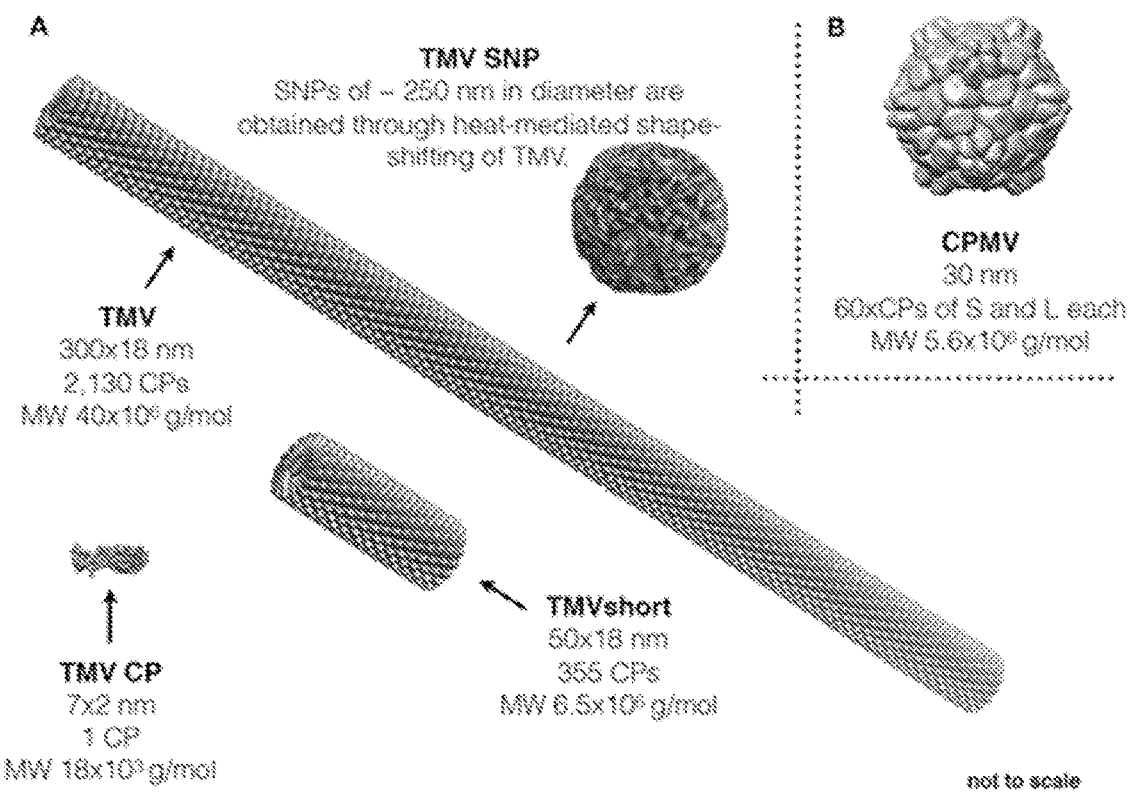
Figs. 10A-B
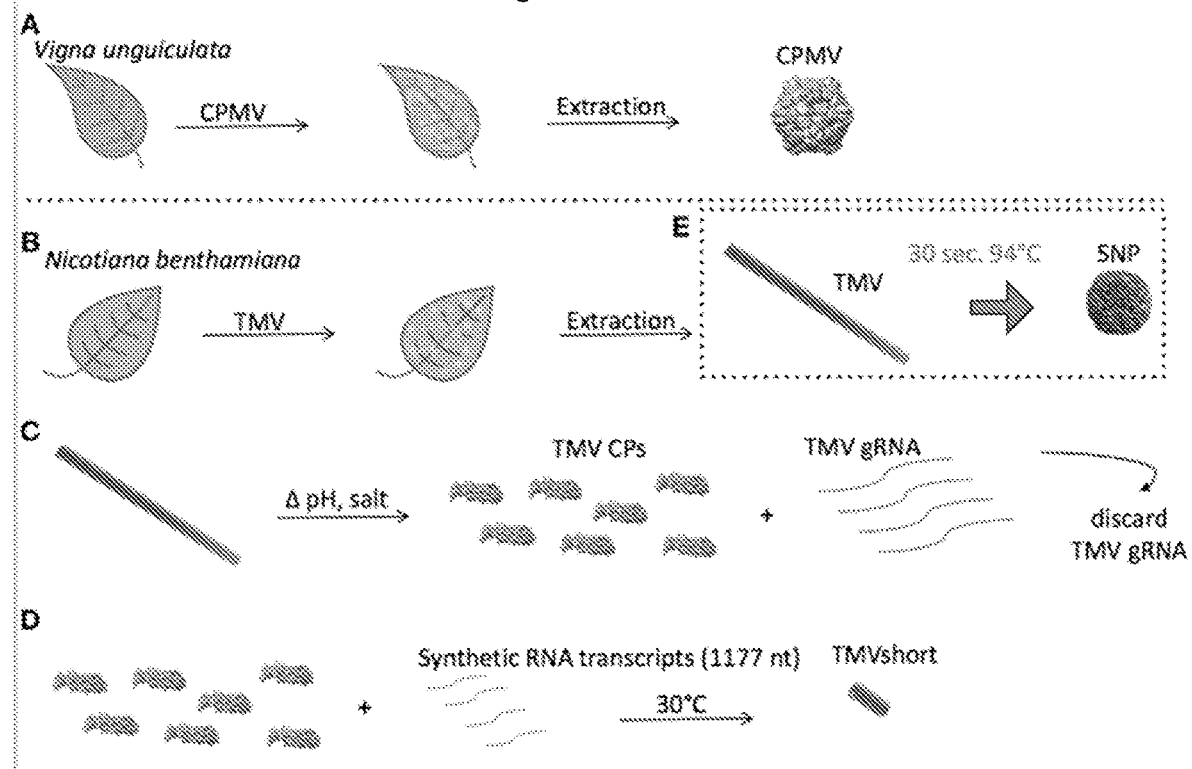
Figs. 11A-E

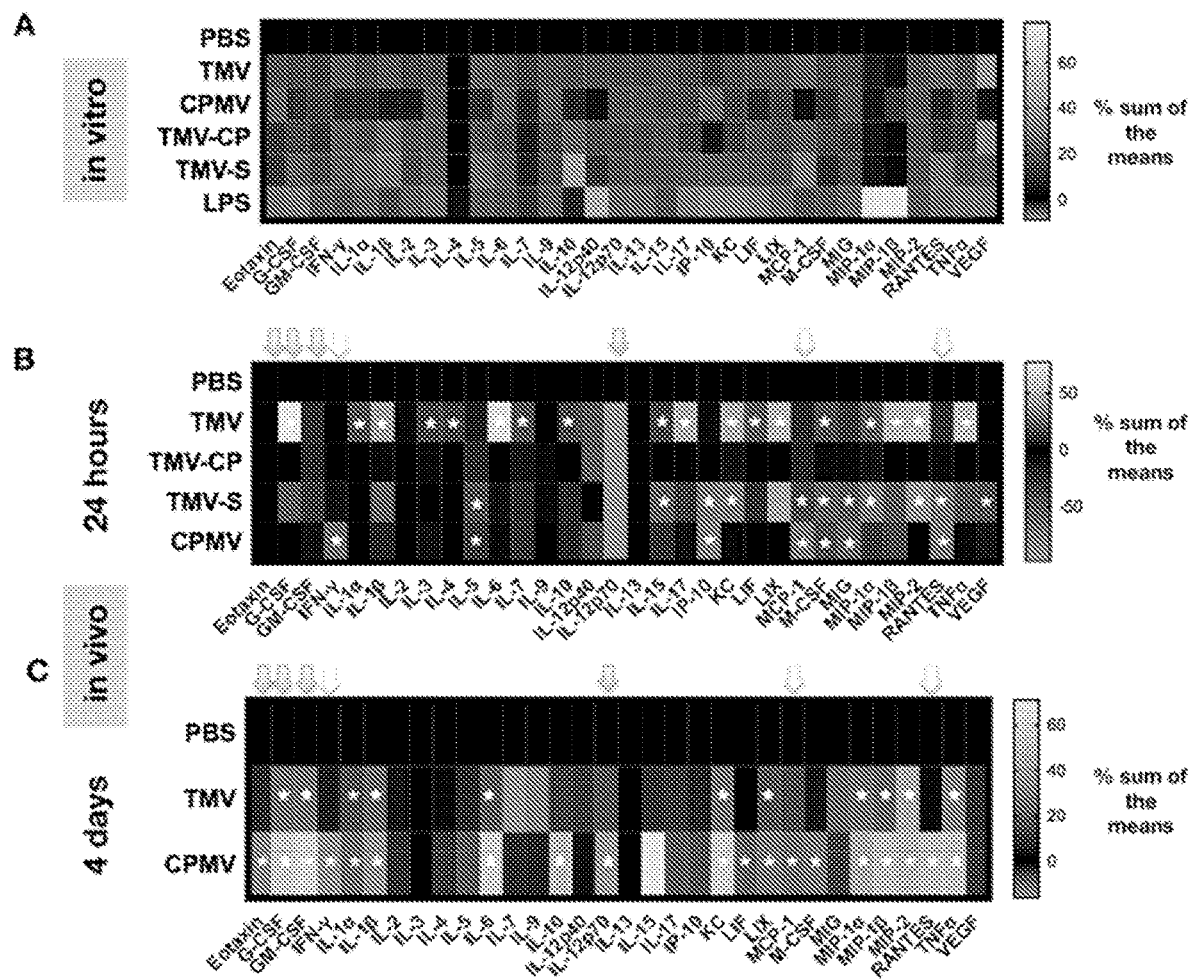
Figs. 14A-C

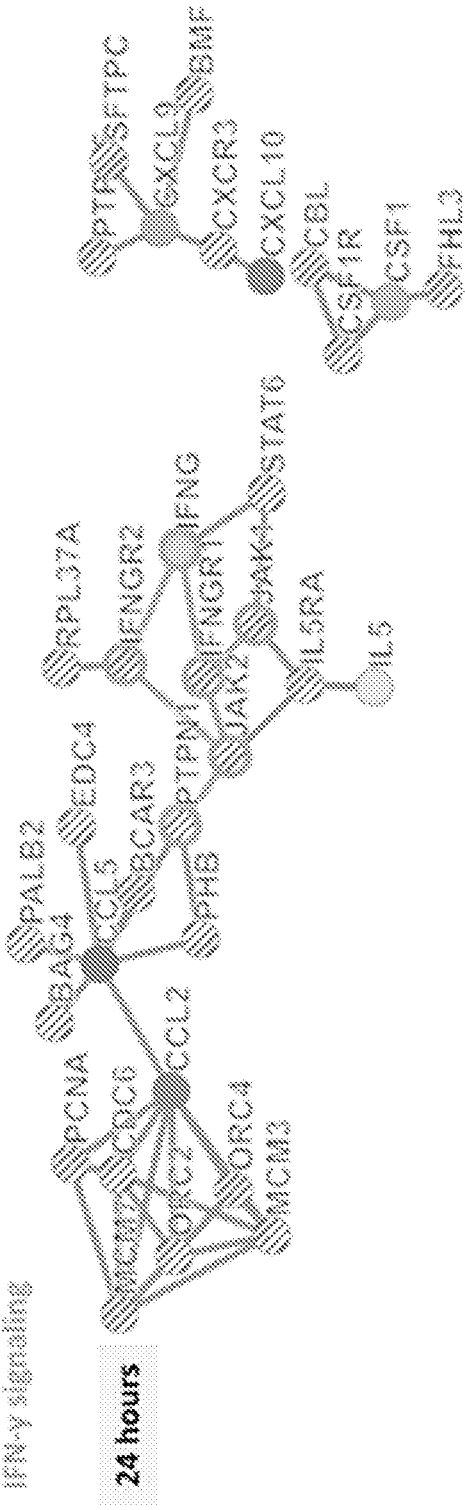
Figs. 15A-B

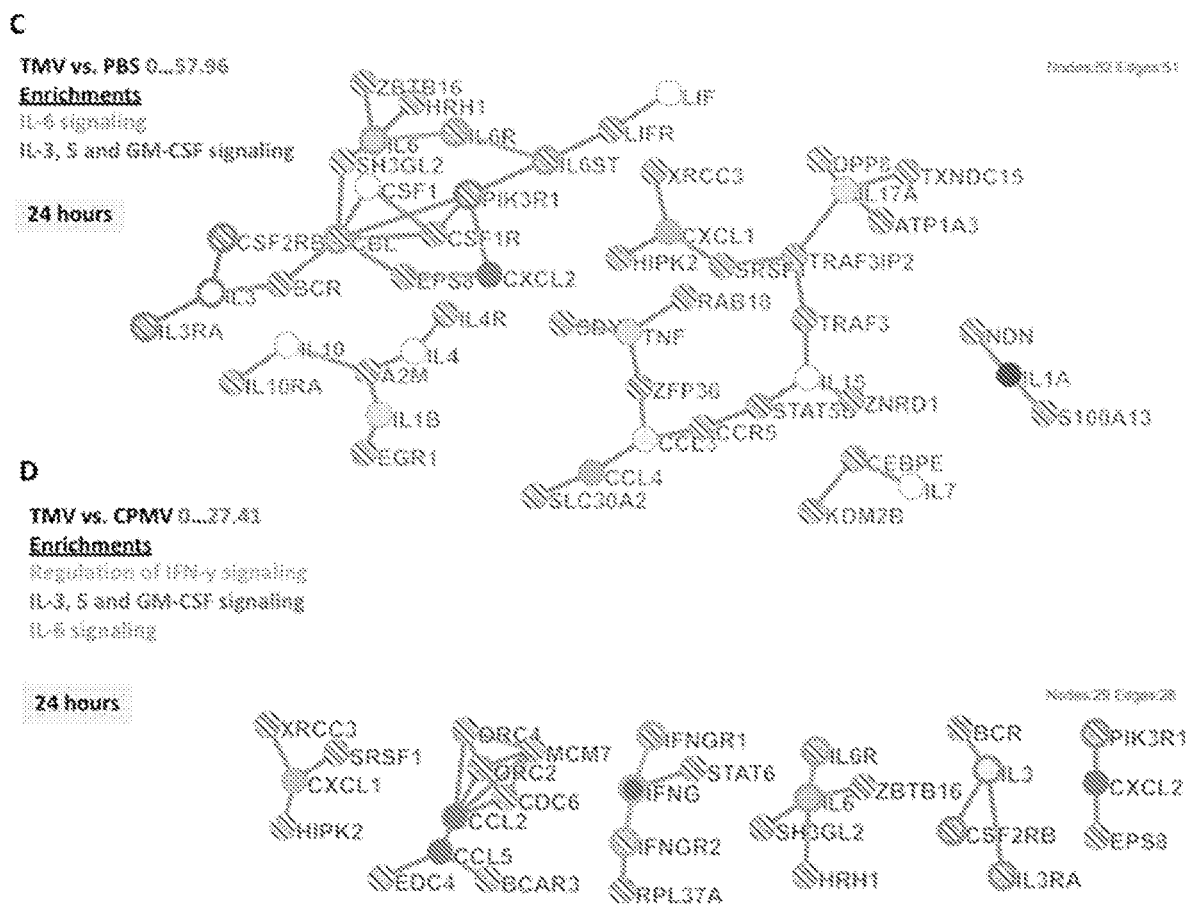
Figs. 15C-D

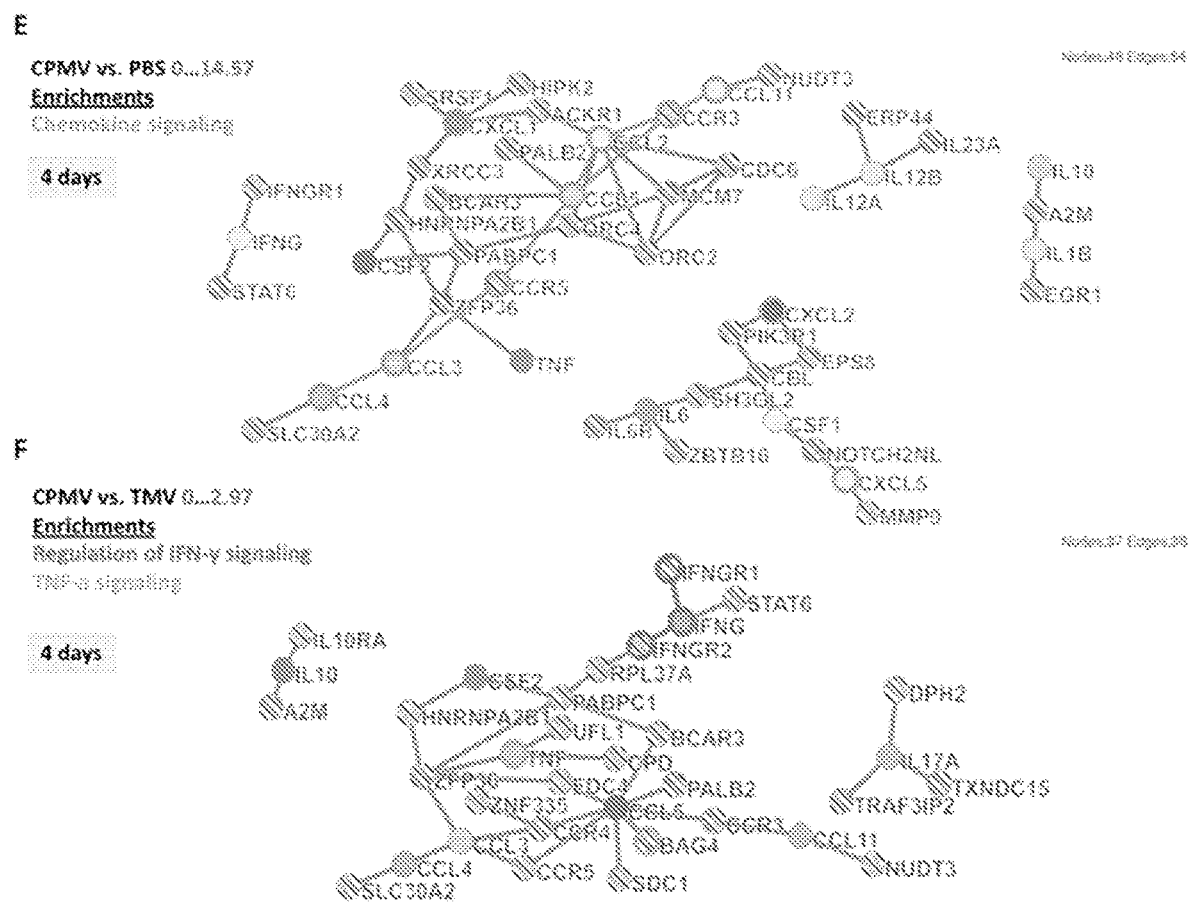
Figs. 15E-F

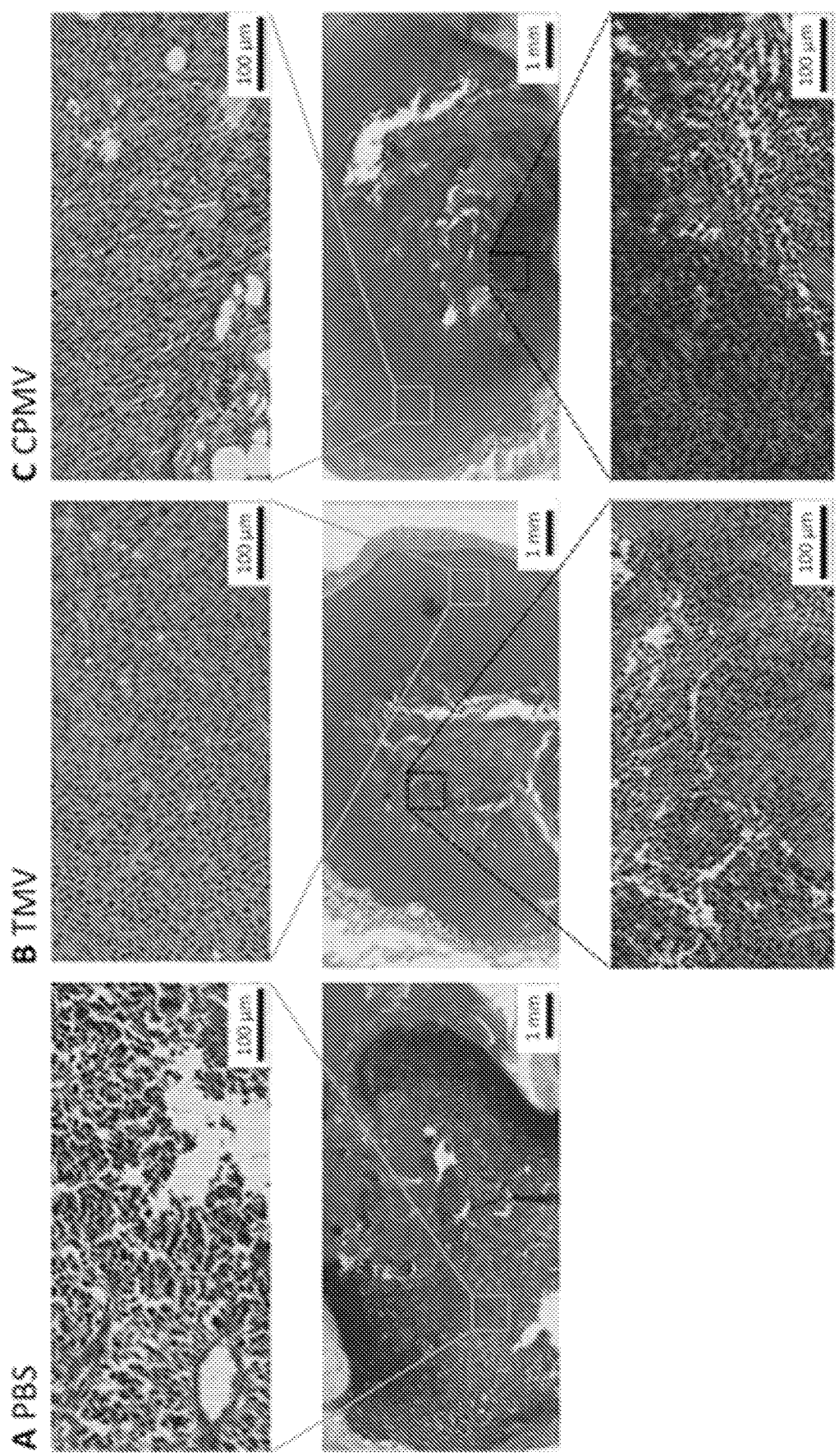
Figs. 16A-C

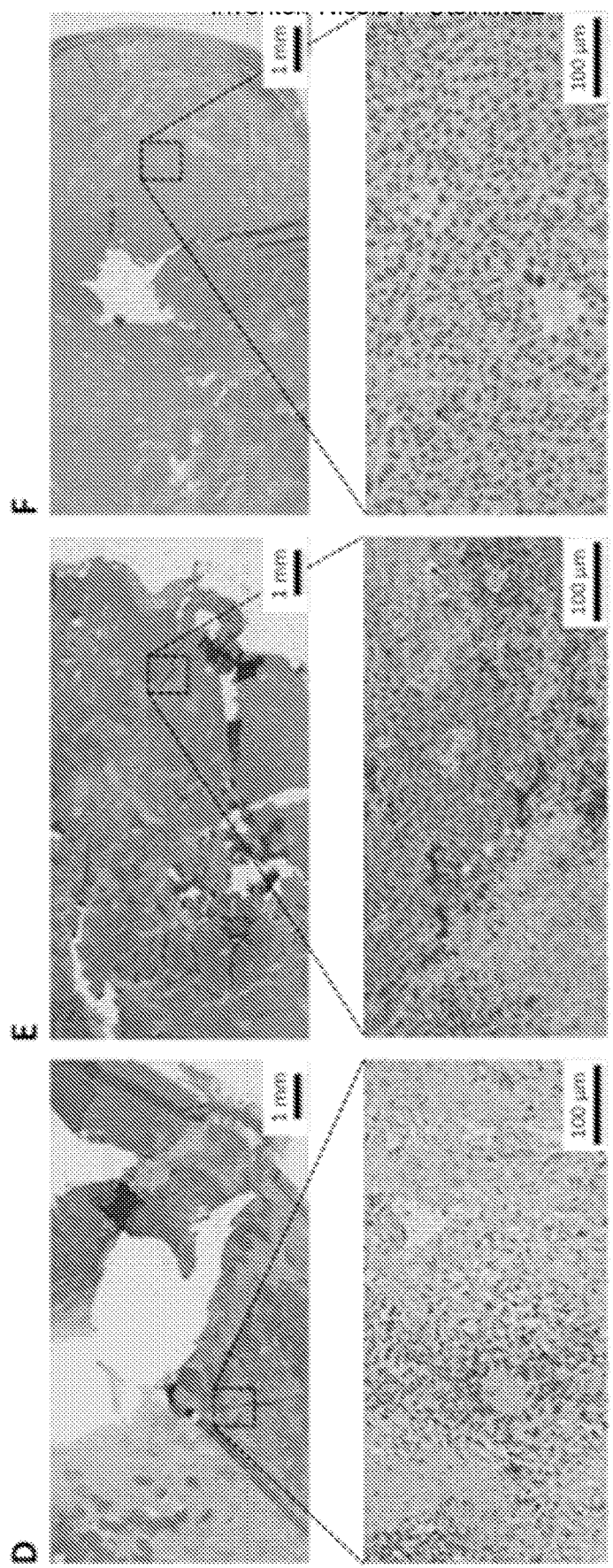
Figs. 16D-F

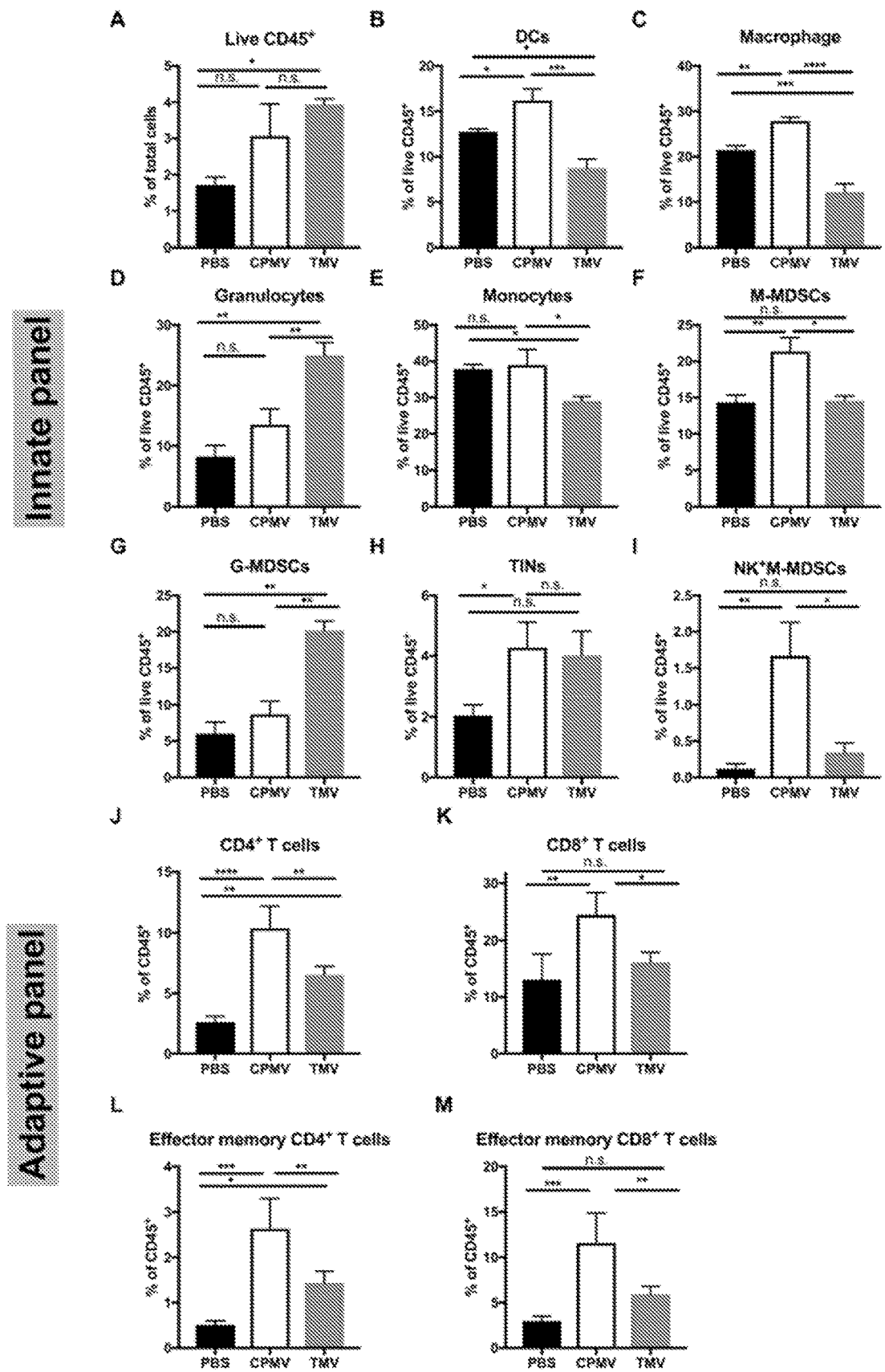
Figs. 17A-M

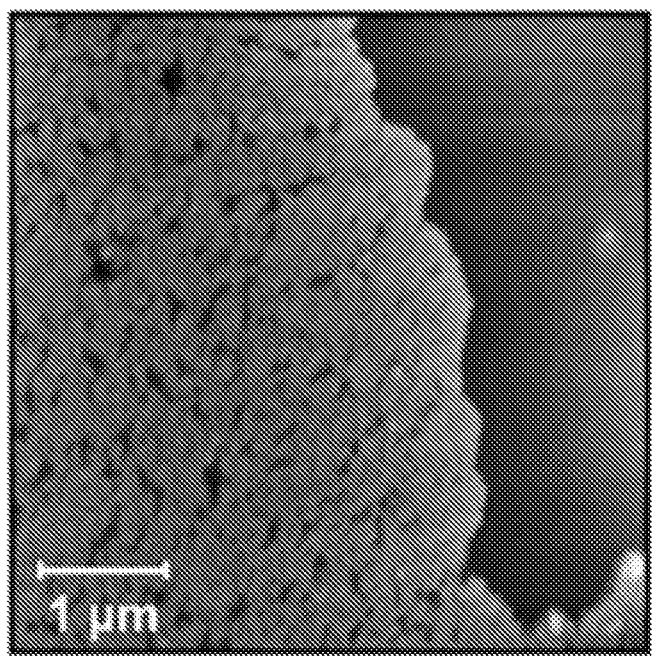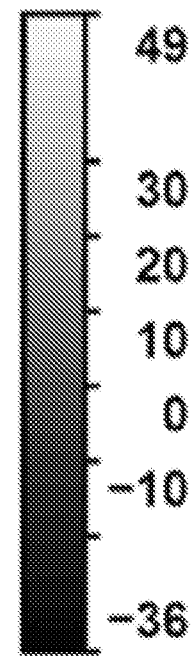
Fig. 19B
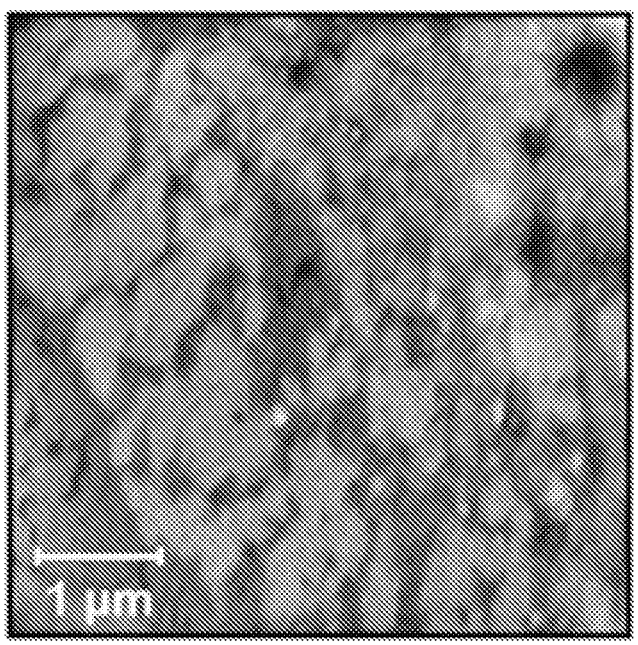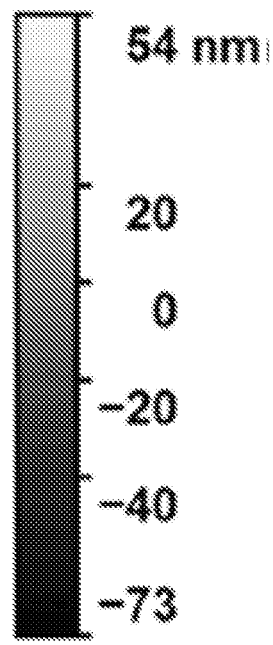
Fig. 19C (C)
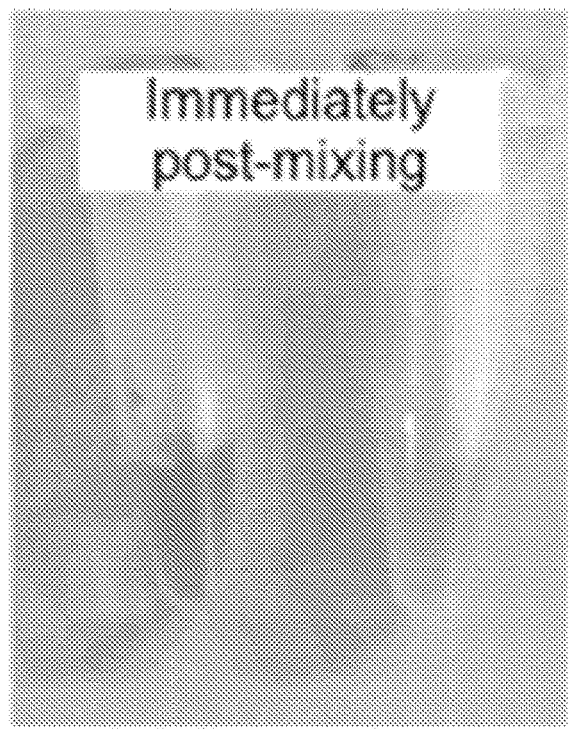
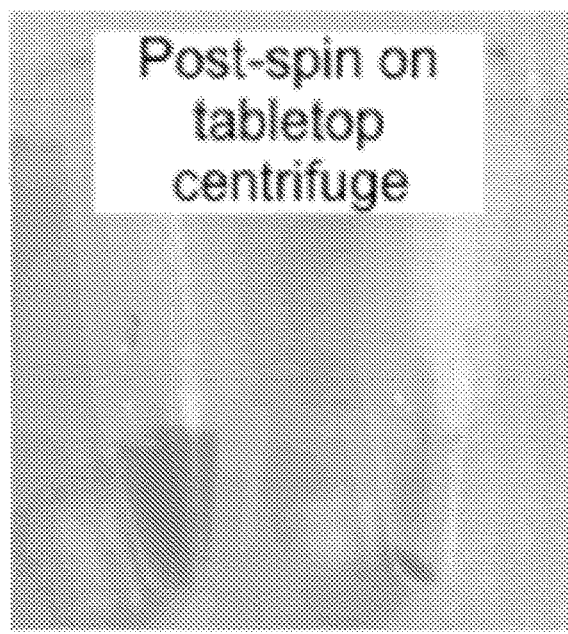
Fig. 21C A
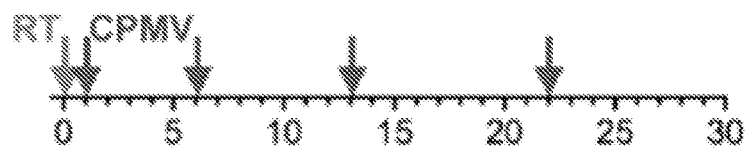
B
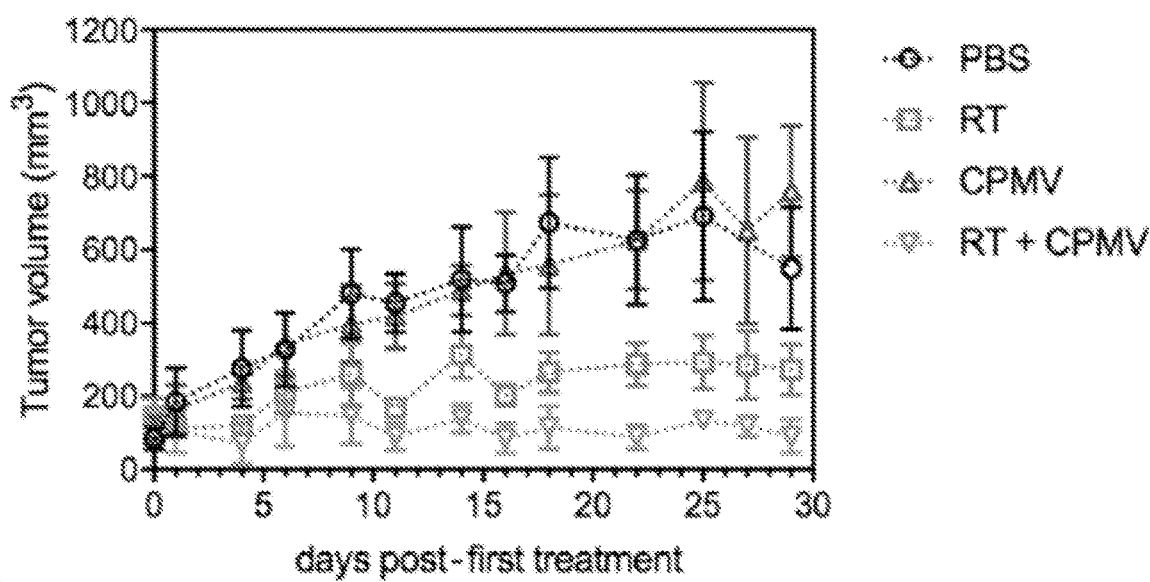
C
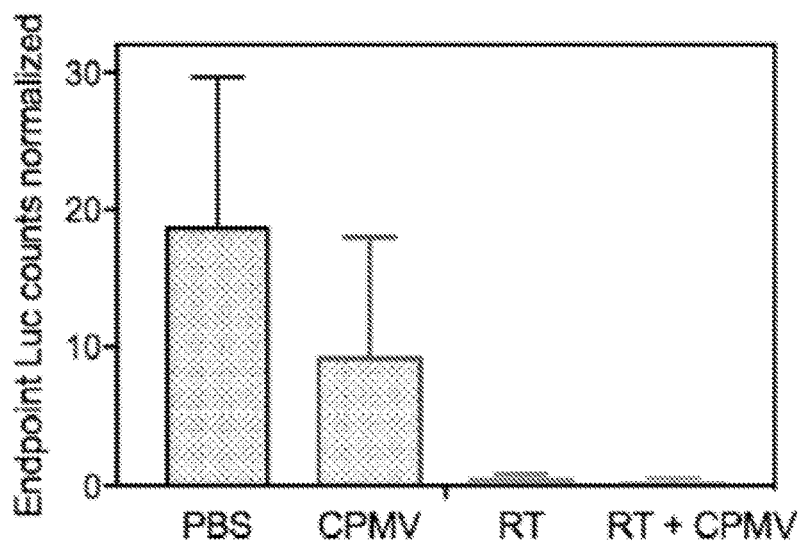
Figs. 23A-C

CANCER IMMUNOTHERAPY USING VIRUS PARTICLES

GOVERNMENT FUNDING

This invention was made with Government support under NIH Training Grant No. 5T32AI007363-22, NIH Training Grant No. T32 HL105338, and Grant No. NIH 1 U54 CA151662 awarded by the National Institutes of Health, and Grant No. CMMI 1333651 awarded by the National Science Foundation. The Government has certain rights in the invention.

RELATED APPLICATION

This application claims priority to Ser. No. 15/589,677, filed May 8, 2017, the subject matter of which is incorporated herein by reference in its entirety.

BACKGROUND

Regardless of tissue of origin, metastatic cancers uniformly carry poor prognoses. Conventional chemo- and radiotherapy are largely ineffective for late stage disease. The emerging field of tumor immunology offers new therapeutic options. Novel therapeutics that seek to induce anti-tumor immunity, such as immune checkpoint inhibitors, chimeric antigen receptor cell therapies, and tumor-associated antigen cancer vaccines show promise, but the development of immunotherapy for cancer is in an early stage and it is likely that, as with other cancer therapies, immunotherapies will be combined for optimal efficacy. Each cancer type is unique but many solid tumors metastasize to the lungs. An option with limited exploration is direct application of immunostimulatory reagents into the suspected metastatic site or an identified tumor. This approach, in situ vaccination, can modulate the local microenvironment and, like therapies such as T cell checkpoint blocking antibodies, can relieve immunosuppression and potentiate anti-tumor immunity against antigens expressed by the tumor.

Research into nanoparticles as cancer therapies to this point has largely focused on them as a delivery platform: the loading of particles with tumor-associated antigen and immune agonists for the stimulation of anti-tumor immunity, or the loading of particles with pre-existing conventional chemotherapeutic drugs for delivery to tumors as a means to reduce toxicity. Sheen et al., Wiley Interdiscip Rev Nanomed Nanobiotechnol., 6(5):496-505 (2014). However, the tendency of nanoparticles to interact with and to be ingested by innate immune cells gives them potential as immunostimulatory, immunoregulatory and immunostimulatory agents if they modulate the characteristics of the ingesting innate immune population.

Virus-like particles (VLPs) refer to the spontaneous organization of coat proteins into the three dimensional capsid structure of a particular virus. Like active viruses, these particles are in the 20-500 nm size range, but they are devoid of the virus nucleic acid. VLPs have already been deployed as antigen components of antiviral vaccines against infectious counterpart viruses hepatitis B (Halperin et al., Vaccine, 30(15):2556-63 (2012)) and human papilloma virus (Moreira et al., Hum Vaccin., 7(7):768-75 (2011)). By preventing infection with viruses that cause cancer, vaccines utilizing VLPs are currently contributing to reductions in cancer incidence.

Recent studies have demonstrated that VLP therapeutic efficacy extends beyond the specific antigen array that they carry and that they may possess inherent immunogenic properties that can stimulate immune responses against infectious agents that do not carry any antigen included in the VLP. Rynda-Apple et al., Nanomed., 9(12):1857-68 (2014)). VLPs have shown the ability to induce protective immune responses in the respiratory tract in mouse models of infectious diseases of the lungs. VLP treatment protected mice from bacterial pneumonia caused by methicillin-resistant Staphylococcus aureus (MRSA) (Rynda-Apple et al., Am J Pathol., 181(1):196-210 (2012)) and Coxiella burnetii (Wiley et al., PLoS ONE., 4(9):e7142 (2009)). VLPs have also been shown to protect mice in various influenza models. Patterson et al., ACS Nano., 7(4):3036-44 (2013); Richert et al., Eur J Immunol., 44(2):397-408 (2014). Protective immunity in these models was associated with recruitment, activation, and increased antigen-processing capabilities, formation of inducible bronchus-associated lymphoid tissue (iBALTs), and stimulation of $CD4^+$ T and B lymphocytes and $CD8^+$ T cells. It is important to note that these studies reported robust induction of both innate and adaptive immunity and that the VLPs utilized were not antigenic ally related to the infectious agents, yet appeared to exert their therapeutic effect via the inherent immunomodulatory nature of the particles. The mechanistic basis of immunomodulation of any VLP is not known, but it is possible that some VLPs have more of that capacity than others.

SUMMARY

Embodiments described herein relate to methods of treating cancer in a subject. The method includes administering in situ to the cancer a therapeutically effective amount of a plant virus or virus-like particle to the subject. The method can further include administering a therapeutically effective amount of an anticancer agent to the subject.

In some embodiments, the anticancer agent is administered to the subject systemically. In some embodiments, the virus-like particle is administered by inhalation. In some embodiments, the plant virus or virus-like particle is administered proximal to a tumor in the subject. The virus-like particle can be administered with a pharmaceutically acceptable carrier.

In some embodiments, the virus-like particle is a non-infectious virus particle. In some embodiments, the virus or virus-like particle is selected from the group consisting of a plant picornavirus or virus like particle, a rod-shaped plant virus or virus like particle, and a filamentous plant virus or virus like particle. For example, the plant virus or virus-like particle can be selected from the group consisting of a cowpea mosaic virus-like particle, a tobacco mosaic virus, and a potato virus X virus-like particle.

In some embodiments, the in situ administration of a plant virus or virus-like particle to the cancer increases recruitment of tumor infiltrating lymphocytes (TILs) at a tumor site of the subject. The tumor infiltrating lymphocytes can include tumor infiltrating neutrophils (TINs).

In particular embodiments, the plant virus or virus-like particle is a cowpea mosaic virus-like particle. The cowpea mosaic virus-like particle can include an empty RNA free cowpea mosaic virus-like particle (eCPMV). In some embodiments, the cowpea mosaic virus-like particle stimulates an anti-tumor response through recruitment of monocytes into a tumor microenvironment (TME), promotes signaling of the IFN-gamma pathway, and/or increase recruitment of TINs and natural killer cells.

In some embodiments, the plant virus or virus-like particle is a tobacco mosaic virus (TMV) or virus-like particle.

In some embodiments, the TMV or TMV virus-like particle can induces IL-6 production at a TME.

The cancer treated can include a metastatic cancer. In some embodiments, the cancer is selected from the group consisting of melanoma, breast cancer, colon cancer, lung cancer, and ovarian cancer.

In some embodiments, the plant virus-like particle is loaded with or conjugated to a cargo molecule. The cargo molecule can include an anticancer agent.

The method can further include the step of ablating the cancer. The method can further include the step of administering a therapeutically effective amount of a radiotherapy (RT) to the subject.

In certain embodiments, the method can further include a therapeutically effective amount of a magnetic iron oxide nanoparticle (mNPH) to the subject. The mNPH can be activated with an alternating magnetic field (AMF) to produce moderate heat. In some embodiments, the mNPH can be administered in combination with hypofractionated RT (HERT).

In some embodiments, the plant virus or virus-like particle is formulated in a slow-release formulation. The slow release formula can include a plant virus or virus-like particle and dendrimer hybrid aggregate.

Other embodiments described herein also relate to methods of treating cancer in a subject. The method includes administering to the subject a therapeutically effective amount of a potato virus X virus-like particle and an anticancer agent. In some embodiments, the anticancer agent can be conjugated directly or indirectly to the potato virus X virus-like particle. In some embodiments, the potato virus X virus-like particle and/or anticancer agent can be administered together with a pharmaceutically acceptable carrier.

In some embodiments, the potato virus X virus-like particle can be administered in situ to the cancer and the anticancer agent is administered to the subject separately. In some embodiments, the anticancer agent is administered to the subject systemically.

In some embodiments, the potato virus X virus-like particle administered to the subject stimulates an anti-tumor response through recruitment of monocytes into a tumor microenvironment (TME), promotes signaling of the IFN-gamma pathway, and/or increases IL1β and M-CSF in the TME.

In some embodiments, the anticancer agent is an antitumor agent. The antitumor agent can include doxorubicin (DOX). The cancer treated can be selected from the group consisting of melanoma, breast cancer, ovarian cancer, and colon cancer. In certain embodiments, the cancer can include a melanoma.

BRIEF DESCRIPTION OF THE FIGURES

FIGS. 1A and 1B provides bar graphs showing eCPMV nanoparticles are inherently immuonogenic. (A) Bone marrow-derived dendritic cells (BMDCs) exposed to eCPMV produce elevated levels of pro-inflammatory cytokines in vitro. (B) Thioglycollate-elicited primary macrophages also secrete significantly elevated levels of the same panel of cytokines. Both cell types were cultured for 24 hr with 20 μg eCPMV (dark gray bars) and cytokine levels were analyzed using a multiplexed luminex array.

FIG. 2A-2D provides graphs showing eCPMV inhalation induces dramatic changes in immune cell composition and cytokine/chemokine milieu in B16F10 lung tumor-bearing mice. (A) Representative FACS plots pre-gated on live $CD45^+$ cells of non-tumor-bearing mice treated with PBS (top left) or eCPMV (top right) and B16F10 lung tumor-bearing mice treated with PBS (bottom left) or eCPMV (bottom right). B16F10 mice were treated on day 7 post-B16F10 IV injection. Lungs were harvested 24 hr after intratracheal injection of PBS or 100 ug eCPMV. Labeling indicates (i) quiescent neutrophils, (ii) alveolar macrophages, (iii) monocytic MDSCs, (iv) granulocytic MDSCs, (v) tumor-infiltrating neutrophils, and (vi) activated neutrophils. Numbers beside circled groups is % of $CD45^+$ cells. Arrows indicate TINs (blue) and $CD11b^+$ activated neutrophils (red). Gating strategies available in supplemental data. (B) Changes in innate cell subsets induced by eCPMV inhalation are quantified as a percentage of $CD45^+$ cells (top) and total number of cells (bottom) as presented in panel (A). (C) Representative histograms for TINs, activated neutrophils, alveolar macrophages, and monocytic MDSCs indicating uptake of Alexa488-labeled CPMV, class-II, and CD86 activation markers. (D) Lungs of B16F10 lung tumor-bearing mice exhibited elevated levels of pro-inflammatory cytokines and chemoattractants when treated with eCPMV as in panel (A).

FIGS. 4A-4C provide graphs showing eCPMV treatment efficacy in B16F10 lung model is immune-mediated. (A) eCPMV inhalation did not significantly affect tumor progression when mice lack Il-12. (B) Treatment efficacy was also abrogated in the absence of Ifn-γ. (C) NOD/scid/Il2R-γ$^{-/-}$ mice lacking T, B, and NK cells also failed to respond to eCPMV inhalation therapy.

FIGS. 5A-5D provide graphs and images showing eCPMV immunotherapy is successful in metastatic breast, flank melanoma, colon, and ovarian carcinoma models. (A) Mice challenged with 4T1 breast tumors and intratracheally injected with PBS rapidly developed (IVIS images) and succumbed (Kaplan-Meier) to metastatic lung tumors beginning on day 24, whereas tumor development was delayed and survival significantly extended in mice receiving intratracheal injection of eCPMV. (B) Mice bearing intradermal flank B16F10 tumors directly injected with eCPMV (arrows indicate treatment days) showed noticeably delayed tumor progression relative to PBS-injected controls and, in half of eCPMV-treated mice, the tumor was eliminated altogether. (C) Mice bearing intradermal flank CT26 colon tumors also responded to direct injection of eCPMV (arrows indicate treatment days) with significantly delayed growth when compared to PBS-injected controls. (D) eCPMV also proved successful as a therapy for ID8-Defb29/Vegf-A ovarian cancer-challenged mice, significantly improving survival when injected IP relative to PBS-injected controls.

FIGS. 8A-E illustrate Synthesis and characterization of PVX-DOX. A) Scheme of DOX loading onto PVX. B) Agarose gel electrophoresis of PVX, PVX-DOX, and free DOX under UV light (top) and after Coomassie Blue staining (bottom). C) TEM images of negatively stained PVX-DOX. D) UV/visible spectrum of PVX-DOX. E) Efficacy of PVX-DOX vs. DOX in B16F10 cells after 24 hours exposure (MTT assay).

FIGS. 10A-B illustrate CPMV and TMV nanoparticle library. (A) Schematic showing the different TMV formulations: native TMV measures 300×18 nm and consists of 2,130 copies of an identical coat protein (CP). Free CP was obtained through TMV disassembly and TMVshort was obtained through assembly using in vitro transcribed RNA of defined lengths; spherical TMV nanoparticles (SNPs) were obtained through heat-mediated shape-shifting. (B) Depiction of CPMV; CPMV consists of 60 copies each of a small (S) and large (L) CP.

FIGS. 11A-E illustrate the production of viral nanoparticle library. Schematic showing the molecular farming of CPMV (A) and TMV (B). (C) Disassembly of TMV into its CPs (and genomic RNA [gRNA]). (D) Assembly TMVshort via RNA templated assembly. (E) Thermal transition of TMV into SNP.

FIGS. 14A-C illustrate cytokine release profiles. (A) Heat maps depicting cytokines and chemokines levels BMDCs after exposure to PBS, TMV, TMV-CP, TMV-S (TMVshort), CPMV or LPS, data were obtained using a 32-plex Luminex assay; all samples were analyzed in duplicates, averaged values were analyzed and % sum of the means are plotted (green signal indicates an increase and red indicates a decrease in signal). (B+C) 32-plex Luminex assay of homogenized B16F10 dermal tumors at 24 hours post initial in situ vaccination (B) and 4 days post-initial treatment (C) animals received two treatments; one on day 1 and the second on day 4, tumors were harvested 4 hours post the second treatment). Results are normalized to PBS levels and by the sum of each column. Yellow and green arrows highlight critical chemo/cytokines. The asterisks (*) indicate statistical significance over PBS with p<0.05 being statistical significant.

FIGS. 15A-F illustrate Cytokine Pathway Analyses. Cytokine/chemokine release data were used to develop pathways based on p-value and fold changes in expression. (A) Table showing cytokine/chemokine names along with gene symbol [used in pathways]. Cytokine pathways comparing (B) CPMV vs. PBS, (C) TMV vs. PBS, and (D) TMV vs. CPMV at 24 hours post in situ vaccination. Pathways at 4 days post in situ vaccination compare (E) CPMV vs. PBS and (F) CPMV vs. TMV. Colored circles represent input cytokines whose expression was significant compared to reference group (p<0.05). Intensity of color indicates degree of fold change with brighter colors having the largest difference (Red is a positive fold change while blue is a negative fold change). Lined circles indicate other genes that were mapped based on interactions with input genes. Outlines of circles and connections indicate the enriched pathway associated with the specific color.

FIGS. 16A-F illustrate histological Analyses. Paraffin embedded B16F10 tumors. (A–C) H&E stained tumors six days post in situ vaccination with PBS, TMV vs. CPMV. Inset row one (orange boxes) showing normal tumor morphology. Inset row two (black boxes) with altered tumor morphology. Insets at 20× magnification. (D–F) CD45 stained tumors six days post in situ vaccination with PBS, TMV vs. CPMV. Inset row at 20× magnification.

FIGS. 17A-L illustrate CPMV and TMV administration induces tumor immune-cell infiltration and activation. C57BL/6 mice bearing dermal B16F10 tumors were treated intratumorally with 100 μg of CPMV, TMV, or PBS on days 8- and 12-post implantation. For the innate panel, 4 hours following the second treatment, tumor cells were harvested to quantify immune-cell infiltration by flow cytometry. (A) proportions of total live CD45$^+$ cells. B–H, proportions of tumor-infiltrated dendritic cells (B) and macrophages (C), granulocytic cells (D), monocytic cells (E), M-MDSCs (F), G-MDSCs (G), and tumor-infiltrated neutrophils (TINs) (H) within the live CD45$^+$ cells. (I) proportions of NK1.1$^+$ in M-MDSCs. For the adaptive panel, animals were sacrificed and tumor harvested 10 days post the first treatment (which occurred on day 8). Analysis of the percentage of CD4+ T cells (J), and CD8$^+$ T cells (K) infiltration is depicted as a percentage of CD45$^+$ cells. Analysis of percentage of effector memory cells (CD44$^+$CD62L$^-$) in CD4$^+$ T cells (L) and CD8$^+$ T cells (M). *p<0.05, p<0.01, *p<0.001, ****p<0.0001.

FIGS. 19A-D illustrate topographical tapping-mode AFM images of A) 0.15 mg mL$^{-1}$ CPMV and 0.15 mg mL$^{-1}$ CPMV-G4 (1:1) in B) 0×10$^{-3}$ m, C) 50×10$^{-3}$ m, and D) 150×10$^{-3}$ m NaCl, which were dropcasted on a freshly cleaved mica surface.

FIGS. 21A-C illustrate a characterization of dye-labeled CPMV and CPMV-G4 assemblies. A) Representative UV-vis absorption spectra of AF647, CPMV, and CPMVAF647 particles. B) SDS-PAGE analysis of wild type CPMV and CPMV-AF647 in white light and after Coomassie Blue staining C) Free CPMV-AF647 and aggregates of CPMV-AF647-G4 immediately following mixing and after a brief spin in a table-top centrifuge (aggregates are too large to be measured with DLS).

FIGS. 23A-C illustrate tumor growth was monitored by caliper measurement and by bioluminescence. (A) Schedule for treatment of tumors with RT and CPMV in situ vaccine injections. (B) Tumor volume as a function of time is plotted for each treatment group (n=4). (C) Total luciferase counts on day 29 (endpoint) normalized to their starting baseline values is shown for each treatment group (n=4).

DETAILED DESCRIPTION

Figure 2B:
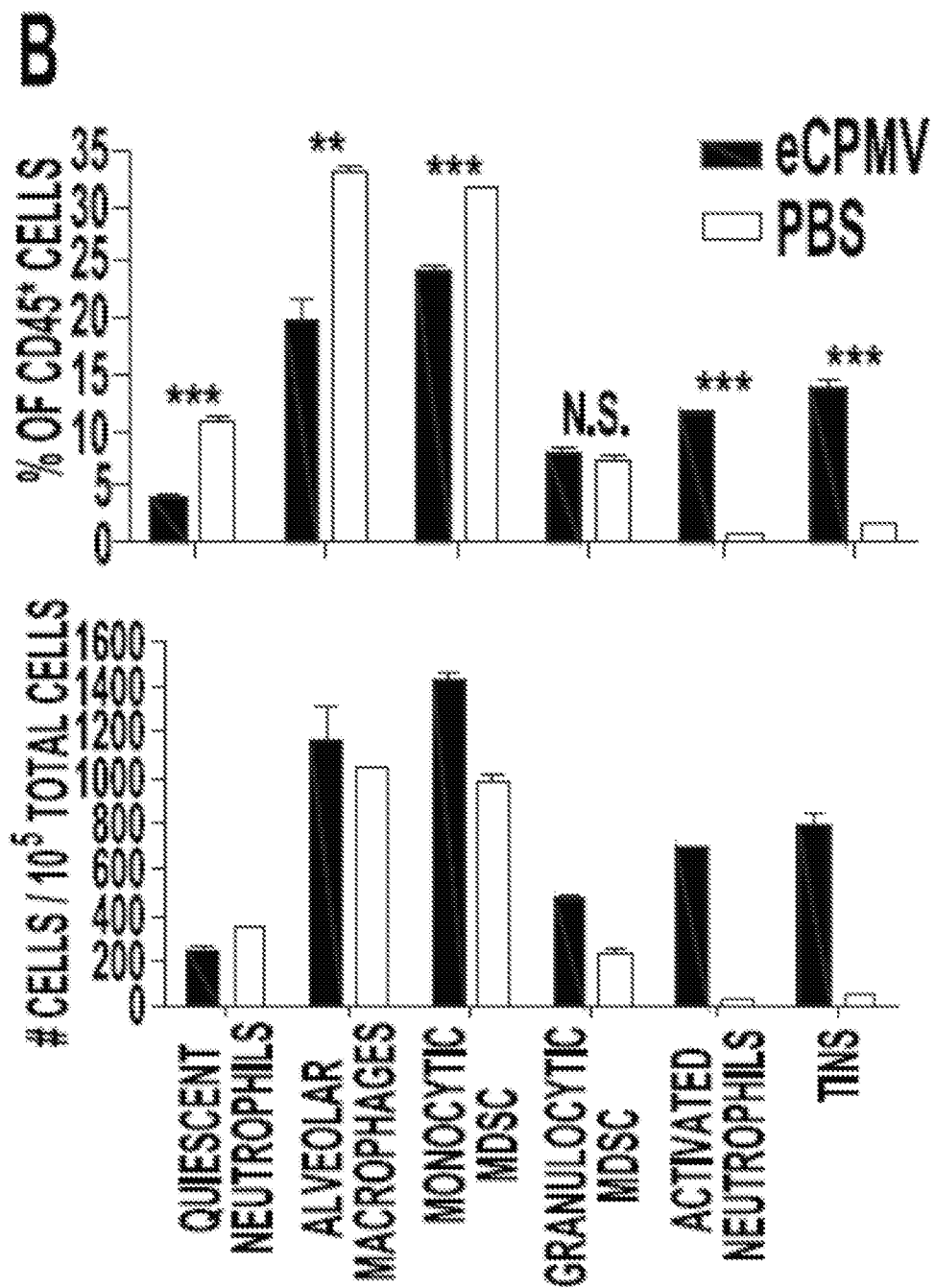

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "nanoparticle" refers to any particle having a diameter of less than 1000 nanometers (nm). In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

The phrases "parenteral administration" and "administered parenterally" are art-recognized terms and include modes of administration other than enteral and topical administration, such as injections, and include, without limitation, intratumoral, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., tumor site), such that it enters the animal's system and, thus, is subject to metabolism and other like processes, for example, subcutaneous administration.

As used herein, the terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. A protein may be a receptor or a non-receptor.

A "nucleic acid" refers to a polynucleotide and includes polyribonucleotides and polydeoxyribonucleotides.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a sufficient amount of the composition used in the practice of the invention that is effective to provide effective treatment in a subject, depending on the compound being used. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to methods of treating cancer in a subject in need thereof by administering in situ to the cancer a therapeutically effective amount of a plant virus or virus-like particle to the subject. The in situ vaccination approach does not rely on the virus-like particles as a vehicle for drug or antigen delivery, but rather on their inherent immunogenicity. In some embodiments, the in situ administration of the virus particle can be proximal to a tumor in the subject or directly to the tumor site to provide a high local concentration of the virus particle in the tumor microenvironment (TME). The method represents a type of in situ vaccination, in which application of an immunostimulatory reagent directly to the tumor modifies the tumor microenvironment so that the immune system is able to respond to the tumor.

It was found that plant virus and virus-like particles and their unique therapeutic features, originally observed in lung infectious disease models, could be utilized for a new application: treating cancer, such as lung cancer and melanoma. In situ vaccination or administration of CPMV, TMV or PVX VLPs alone or in combination with a chemotherapeutic in a model of metastatic lung melanoma as well as dermal melanoma and other cancers (breast, colon, ovarian), was found to have striking efficacy in treating the cancer.

The virus or virus-like particle can be nonreplicating and noninfectious in the subject to avoid infection of the subject and can be regarded as safe from a human health and agricultural perspective. In planta production prevents endotoxin contamination that may be a byproduct of other VLP systems derived from *E. coli*. The VLPs are scalable, stable over a range of temperatures (4-60° C.) and solvent:buffer mixtures.

In some embodiments, plant virus particles or virus-like particles (VLPs) in which the viral nucleic acid is not present are administered in situ to cancer of the subject. Virus-like particles lacking their nucleic acid are non-replicating and non-infectious regardless of the subject into which they are introduced. An example of virus-like particles is empty eCPMV, which is RNA-free.

In other embodiments, the plant virus particles include a nucleic acid within the virus particle. If present, the nucleic acid will typically be the nucleic acid encoding the virus. However, in some embodiments the viral nucleic acid may have been replaced with exogenous nucleic acid. In some embodiments, the nucleic acid is RNA, while in other embodiments the nucleic acid is DNA. A virus particle including nucleic acid will still be nonreplicating and non-infectious when it is introduced into a subject which it cannot infect. For example, plant virus particles will typically be nonreplicating and noninfectious when introduced into an animal subject.

In some embodiments, the plant virus is a plant picornavirus. A plant picornavirus is a virus belonging to the family Secoaviridae, which together with mammalian picornaviruses belong to the order of the Picornavirales. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily Examples of viruses from the Comovirinae subfamily include Cowpea mosaic virus (CPMV), Broad bean wilt virus 1, and Tobacco ringspot virus. In a further embodiment, the virus particles are from the Genus comovirus. A preferred example of a comovirus is the cowpea mosaic virus particles.

In some embodiments, the plant virus or virus-like particle is a rod-shaped plant virus. A rod-shaped plant virus is a virus that primarily infects plants, is non-enveloped, and is shaped as a rigid helical rod with a helical symmetry. Rod shaped viruses also include a central canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus or virus-like particle belongs to a specific virus family, genus, or species. For example, in some embodiments, the rod-shaped plant virus belongs to the Virgaviridae family. The Virgaviridae family includes the genus Furovirus, Hordevirus, Pecluvirus, Pomovirus, Tobamovirus, and Tobravirus. In some embodiments, the rod-shaped plant virus belongs to the genus Tobamovirus. In further embodiments, the rod-shaped plant virus belongs to the tobacco mosaic virus (TMV) species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are ~300 nm in length and ~18 nm in diameter. Negatively stained electron microphotographs show a distinct inner channel of ~4 nm.

In further embodiments, the rod-shaped plant virus or virus-like particle can be combined with other rod-shaped plant virus particles by means of a thermal transition to form an RNA-free spherical nanoparticle (SNP). A SNP is a spherical arrangement of the coat proteins of a plurality of rod-shaped plant virus particles formed by thermal transition of the rod-shaped virus particles. SNPs can be labeled with suitable chemicals prior or post thermal transition; for example, NHS-based chemistries allow one to conjugate functional molecules to SNPs post thermal transition; the SNPs are stable and remain structurally sound after chemical modification. The SNPs can be formed from rod-shaped plant virus particles (e.g., TMV virus particles) by briefly heating the rod-shaped plant virus particles. For example, the rod-shaped plant virus particles can be induced to undergo a thermal transition into SNPs by heating at about 96° C. for about 10 to about 20 seconds. The SNPs are formed from the coat proteins of one or more individual rod-shaped plant virus particles. In various embodiments, the SNP can be formed from about 1 to 10 virus particles, from about 10 to about 20 virus particles, from about 20 to about 30 virus particles, from about 30 to about 40 virus particles, or from about 40 to about 50 virus particles. Depending on the nature of the coat proteins, the number of virus particles incorporated, and the virus particle concentration in the solution in which the thermal transition occurs, the spherical nanoparticles can also vary in size. In some embodiments, the SNPs have a size from about 50 nm to about 800 nm. In further embodiments, the SNPs have a size from about 100 to about 300 nm, or from about 150 to about 200 nm.

In other embodiments, the plant virus or plant virus-like particle is an Alphaflexiviridae virus or virus-like particle. The genera comprising the Alphaflexiviridae family include Allexivirus, Botrexvirus, Lolavirus, Mandarivirus, Potexvirus, and Sclerodarnavirus. In further embodiments, the plant virus particle of the vaccine composition is a Potexvirus particle. Examples of Potexvirus include Allium virus X, Alstroemeria virus X, Alternanthera mosaic virus, Asparagus virus 3, Bamboo mosaic virus, Cactus virus X, Cassava common mosaic virus, Cassava virus X, Clover yellow mosaic virus, Commelina virus X, Cymbidium mosaic virus, Daphne virus X, Foxtail mosaic virus, Hosta virus X, Hydrangea ringspot virus, Lagenaria mild mosaic virus, Lettuce virus X, Lily virus X, Malva mosaic virus, Mint virus X, Narcissus mosaic virus, Nerine virus X, Opuntia virus X, Papaya mosaic virus, Pepino mosaic virus, Phaius virus X, Plantago asiatica mosaic virus, Plantago severe mottle virus, Plantain virus X, Potato aucuba mosaic virus, Potato virus X, Schlumbergera virus X, Strawberry mild yellow edge virus, Tamus red mosaic virus, Tulip virus X, White clover mosaic virus, and Zygocactus virus X. In some embodiments, the plant virus like particle is a Potato virus X virus-like particle.

The virus or virus-like particles can be obtained according to various methods known to those skilled in the art. In embodiments where plant virus particles are used, the virus particles can be obtained from the extract of a plant infected by the plant virus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves are harvested and viral nanoparticles are extracted. In the case of cowpea mosaic virus, 100 mg of virus can be obtained from as few as 50 plants. Procedures for obtaining plant picornavirus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

Cancer Treatment by Virus Particle Administration

This application describes a method of treating cancer in a subject in need thereof by administering in situ a therapeutically effective amount of a plant virus or virus-like particle to the subject. While not intending to be bound by theory, it appears that the plant virus particles have an anticancer effect as a result of eliciting an immune response to the cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers treated by a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

The inherent immunogenicity resulting from an in situ vaccination approach described herein appears to be uniquely potent when the particles are inhaled or when administered through intratumoral administration into dermal tumors or as IP administration when treating disseminated, metastatic ovarian cancer. For treatment of lung tumors, the particles can be intratracheally injected into a subject with established lung tumors and this immunostimulatory treatment results in the rejection of those tumors and systemic immunity that prevents growth of distal tumors. The virus-like particles described herein (e.g., CPMV or PVX) alone are able to stimulate systemic anti-tumor immunity. The virus can potentially render the lung microenvironment inhospitable to tumor cell seeding or continued growth.

Primary lung cancer is the second most common cancer in the United States, behind only breast cancer. Additionally, most other majors cancers frequently metastasize to the lung, including breast, bladder, colon, kidney, melanoma, and prostate. Therefore, in some embodiments, the virus particles are used to treat cancer selected from the group consisting of but not limited to melanoma, breast cancer, bladder cancer, kidney cancer, colon cancer, lung cancer, prostate cancer and ovarian cancer. In some embodiments, the virus particles are used to treat lung cancer. Inhalation is a preferred method of administering the virus or virus-like particles when treating lung cancer. However, inhaled virus particles are able to treat cancer beyond the lung as a result of their ability to stimulate a systemic immune response. For example, in some embodiments, the virus particles are used to treat metastatic cancer which has spread to one or more sites beyond the initial point where cancer has occurred. In other embodiments, the virus or virus-like particles can be administered proximal to tumors in other tissues.

In some embodiments, the method can further include the step of administering a therapeutically effective amount of a cancer therapeutic or cancer therapy to the subject. A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy.

In some embodiments, the method can further include the step of administering a therapeutically effective amount of an anticancer therapeutic agent to the subject. The anticancer therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA. In some embodiments, cytotoxic compounds are included in an anticancer agent described herein. Cytotoxic compounds include small-molecule drugs such as doxorubicin, mitoxantrone, methotrexate, and pyrimidine and purine analogs, referred to herein as antitumor agents.

The anticancer therapeutic agent can include an anticancer or an antiproliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of anticancer therapeutic agents that can be administered in combination with a plant virus or virus-like particle described herein include Taxol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin;

batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-nl; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; temozolomide, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anticancer therapeutic agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; silicon phthalocyanine (PC4) sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosamOinoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Other anticancer agents can include the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Arnad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Still other anticancer therapeutic agents include alkylating agents, such as nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.), antimetabolites, such as folic acid analog (e.g., methotrexate), or pyrimidine analogs (e.g., fluorouracil, floxouridine, Cytarabine), purine analogs (e.g., mercaptopurine, thioguanine, pentostatin, vinca alkaloids (e.g., vinblastin, vincristine), epipodophyllotoxins (e.g., etoposide, teniposide), platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, amino glutethimide).

In particular embodiments, anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-degulin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin, and derivatives (as defined for imaging agents) thereof.

In some embodiments, the method can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, the step ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers).

In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanized or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in-vivo targeting are suitable immunotherapies that can be used together with the virus or virus-like particles of the invention for cancer treatment.

In some embodiments, the step of ablating the cancer includes administering a therapeutically effective amount of radiotherapy (RT) to the subject. It has been found that the combination treatment of radiotherapy and CPMV in situ vaccine resulted in significantly reduced tumor growth compared to RT or CPMV treatment alone. Without being bound by theory, it is believed that RT can prime the tumor by debulking the tumor to provide a burst of tumor antigens in the context of immunogenic cell death that fosters specific immune recognition and response to those antigen; in turn, plant virus nanoparticle-mediated immune stimulation can further augment antitumor immunity to protect from outgrowth of metastases and recurrence of the disease. Thus, in some embodiments, RT is administered prior to in situ administration of the plant virus nanoparticle. In some embodiments, administering in situ to the cancer, (e.g., a tumor site) a therapeutically effective amount of a plant virus or virus-like particle to the subject in combination with administering radiotherapy to the subject can result in an increase in tumor infiltrating lymphocytes (TILs), such as tumor infiltrating neutrophils (TINs) at the tumor site of the subject.

Radiotherapy uses high-energy rays to treat disease, usually x-rays and similar rays (such as electrons). Radiotherapy administered to a subject can include both external and internal. External radiotherapy (or external beam radiation) aims high-energy x-rays at the tumor site including in some cases the peri-tumor margin. External radiotherapy typically includes the use of a linear accelerator (e.g., a Varian 2100C linear accelerator). External radiation therapy can include three-dimensional conformal radiation therapy (3D-CRT), image guided radiation therapy (IGRT), intensity modulated radiation therapy (IMRT), helical-tomotherapy, photon beam radiation therapy, proton beam radiation therapy, stereotactic radiosurgery and/or sterotactic body radiation therapy (SBRT).

Internal radiotherapy (brachytherapy) involves having radioactive material placed inside the body and allows a higher dose of radiation in a smaller area than might be possible with external radiation treatment. It uses a radiation source that's usually sealed in an implant. Exemplary implants include pellets, seeds, ribbons, wires, needles, capsules, balloons, or tubes. Implants are placed in your body, very close to or inside the tumor. Internal radiotherapy can include intracavitary or interstitial radiation. During intracavitary radiation, the radioactive source is placed in a body cavity (space), such as the uterus. With interstitial radiation, the implants are placed in or near the tumor, but not in a body cavity.

In some embodiments, a checkpoint inhibitor can be further administered to eradicate suppressive regulatory T cells prior to RT and initiating an effector immune response with the in situ administration of the plant virus nanoparticle. Exemplary checkpoint inhibitors can include CTLA4 and PD-1/PDL-1 inhibitors. The cytotoxic T-lymphocyte-associated antigen 4 (CTLA-4) and programmed death 1 (PD-1) immune checkpoints are negative regulators of T-cell immune function and inhibition of these targets, results in increased activation of the immune system. Therefore, in some embodiments, a checkpoint inhibitor administered to a subject can include a CTLA-4 and/or PD-1 inhibitor. For example, Ipilimumab, an inhibitor of CTLA-4, is approved for the treatment of advanced or unresectable melanoma. Nivolumab and pembrolizumab, both PD-1 inhibitors, are approved to treat patients with advanced or metastatic melanoma and patients with metastatic, refractory non-small cell lung cancer. In addition the combination of ipilimumab and nivolumab has been approved in patients with BRAF WT metastatic or unresectable melanoma.

It has been shown that moderate magnetic nanoparticle hyperthermia (mNPH) treatment administered to a tumor can generate immune-based systemic resistance to tumor rechallenge. Therefore, in some embodiments, a therapeutically effective amount of a moderate magnetic nanoparticle hyperthermia (mNPH) treatment can be administered to the subject in combination with a plant virus-like particle and/or radiotherapy, wherein the mNPH is activated with an alternating magnetic field (AMF) to produce moderate heat. Without being bound by theory, it is believed that plant virus-like particle immune adjuvants, such as a plant virus nanoparticle and/or a mNPH, will combine with RT-induced generation of immunogenic cell death (ICD) to expand the tumor specific effector T cell population causing longer local and distant tumor remission.

A mNPH treatment can include the use of a magnetic iron oxide nanoparticle (IONP). Once administered to the subject intratumorally, the mNPH can, in some embodiments, be activated with an alternating magnetic field (AMF) to produce moderate heat (e.g., 43°/60 min) at the tumor site. In some embodiments the RT is hypofractionated RT (HFRT) that delivers larger but fewer doses/fractions than typical RT therapies. In an exemplary embodiment, a therapeutically effective amount of RT can be administered to a subject in combination with a combination of a plant virus nanoparticle and/or a mNPH for the treatment of oral melanoma.

Cargo Molecules

In some embodiments, the virus particle is loaded with or bonded to a cargo molecule. A variety of different types of cargo molecules can be loaded into or bonded to the virus particles. Cargo molecules that are loaded into the virus particle must be sufficiently small to fit within the virus capsid (i.e., have a size of 10 nm or less for a typical icosohedral capsid). Preferred cargo molecules for the present invention include antitumor agents. Alternately, rather than being loaded into the virus particle, the cargo molecule can be bonded or conjugated to the plant virus-like particle. The term "conjugating" when made in reference to an cargo molecule, such as an anticancer agent and a plant virus particle as used herein, means covalently linking the cargo molecule to the virus subject to the single limitation that the nature and size of the agent and the site at which it is covalently linked to the virus particle do not interfere with the biodistribution of the modified virus.

In general, cargo molecules can be conjugated to the plant virus by any suitable technique, with appropriate consideration of the need for pharmacokinetic stability and reduced overall toxicity to the patient. The cargo molecule can be linked to the interior or the exterior of the virus, while in some embodiments the cargo molecule is linked to both the interior and the exterior of the virus. The location of the cargo molecule on the interior or exterior can be governed by the amino acids of the viral coat protein.

A cargo molecule can be coupled to a virus particle either directly or indirectly (e.g. via a linker group). In some embodiments, the cargo molecule is directly attached to a functional group capable of reacting with the agent. For example, a nucleophilic group, such as an amino or sulfhydryl group, can be capable of reacting with a carbonyl-containing group, such as an anhydride or an acid halide, or with an alkyl group containing a good leaving group (e.g., a halide). Alternatively, a suitable chemical linker group can be used. A linker group can serve to increase the chemical reactivity of a substituent on either the agent or the virus particle, and thus increase the coupling efficiency. A preferred group suitable as a site for attaching cargo molecules to the virus particle is one or more lysine residues present in the viral coat protein that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g. alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

Alternatively, a suitable chemical linker group can be used. A linker group can serve to increase the chemical reactivity of a substituent on either the agent or the virus particle, and thus increase the coupling efficiency. Suitable linkage chemistries include maleimidyl linkers, which can be used to link to thiol groups, isothiocyanate and succinimidyl (e.g., N-hydroxysuccinimidyl (NHS)) linkers, which can link to free amine groups, diazonium which can be used to link to phenol, and amines, which can be used to link with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

Dosage and Formulation of Virus or Virus-Like Particles

When used in vivo, the plant virus or virus-like particles can be administered as a pharmaceutical composition, comprising a mixture, and a pharmaceutically acceptable carrier. The plant virus or virus-like particle may be present in a pharmaceutical composition in an amount from 0.001 to 99.9 wt %, more preferably from about 0.01 to 99 wt %, and even more preferably from 0.1 to 95 wt %.

The virus particles, or pharmaceutical compositions comprising these particles, may be administered by any method designed to provide the desired effect. Administration may occur enterally or parenterally; for example orally, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device.

A preferred method for administering the plant virus or virus-like particle to a subject having lung cancer is by inhalation. For example, the virus particles can be administered intratracheally to the lung of the subject. For administration by inhalation, the virus particles are preferably formulated as an aerosol or powder. Various methods for pulmonary delivery of nanoparticles are discussed by Mansour et al., Int J Nanomedicine. 2009; 4:299-319, the disclosure of which is incorporated herein by reference.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

A pharmaceutically acceptable carrier for a pharmaceutical composition can also include delivery systems known to the art for entraining or encapsulating drugs, such as anti-cancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J. Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

Suitable doses can vary widely depending on the therapeutic or imaging agent being used. A typical pharmaceutical composition for intravenous administration would be about 0.1 mg to about 10 g per subject per day. However, in other embodiments, doses from about 1 mg to about 1 g, or from about 10 mg to about 1 g can be used. Single or multiple administrations of the compositions may be administered depending on the dosage and frequency as required and tolerated by the subject. In any event, the administration regime should provide a sufficient quantity of the composition of this invention to effectively treat the subject.

The formulations may be conveniently presented in unit dosage form and may be prepared by any of the methods well known in the art of pharmacy. Preferably, such methods include the step of bringing the virus particles into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect.

One skilled in the art can readily determine an effective amount of plant virus, virus-like particles and/or cancer therapeutics to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the virus particles to be administered can be estimated from the volume of cancer cells to be killed or volume of tumor to which the virus particles are being administered.

Useful dosages of the active agents can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the virus particles vary depending upon many different factors, including means of administration, target site, physiological state of the patient, whether the patient is human or an animal, characteristics of the subject, such as general health, age, sex, body weight and tolerance to drugs as well as the degree, severity and type of cancer, other medications administered, and whether treatment is prophylactic or therapeutic. The skilled artisan will be able to determine appropriate dosages depending on these and other factors using standard clinical techniques.

The methods described herein contemplate single as well as multiple administrations, given either simultaneously or over an extended period of time. A pharmaceutically acceptable composition containing the plant virus, virus-like particle, and/or additional cancer therapeutic can be administered at regular intervals, depending on the nature and extent of the cancer's effects, and on an ongoing basis. Administration at a "regular interval," as used herein, indicates that the therapeutically effective amount is administered periodically (as distinguished from a one-time dose). In one embodiment, the pharmaceutically acceptable composition containing the plant virus, virus-like particle, and/or an additional cancer therapeutic is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased.

For example, the administration of a plant virus or virus like particle and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

In some embodiments, the frequency of administration of a plant-virus nanoparticle can pose challenging for clinical implementation. Therefore, in some embodiments, the plant viral nanoparticle administered in situ to a subject can be formulated in a slow release formulation in order to sustain immune stimulation by maintaining a therapeutic concentration of the plant virus or virus-like nanoparticle in situ while alleviating the need for frequent administrations. In some embodiments, a slow release formulation can include a polymer-based hydrogel or a dendrimer.

In some embodiments, a slow-release formulation can include a plant virus-like particle dendrimer hybrid aggregate. The dendrimer can include a positively-charged polyamidoamine (PAMAM) dendrimer, such as a medium-sized generation 3 (G3) or generation 4 (G4) PAMAM dendrimer. Depending on the specific application, the plant virus-like particle-dendrimer hybrid aggregates can vary in size and release rate of the plant virus-like particle from the dendrimer when administered to a subject. In some embodiments, the plant virus-like particle-dendrimer hybrid aggregates are formulated so that at low salt the assembly of the aggregates is triggered and while under physiologic salt concentrations disassembly and plant virus nanoparticle release is induced. In an exemplary embodiment, CPMV and polyamidoamine generation 4 dendrimer form aggregates (CPMV-G4), see FIG. 18A. In particular embodiments, the plant virus-like particle-dendrimer hybrid aggregates, such as CPMV-G4 aggregates, can be administered in situ for the treatment of ovarian cancer or gliomas.

Examples have been included to more clearly describe particular embodiments of the invention. However, there are a wide variety of other embodiments within the scope of the present invention, which should not be limited to the particular examples provided herein.

EXAMPLES

Example 1

In Situ Vaccination with Plant-Derived Virus-Like Nanoparticle Immunotherapy Suppresses Metastatic Cancer Current therapies are often ineffective for metastatic cancer and emerging immunotherapies, while promising, are early in development. In situ vaccination refers to a process in which immunostimulatory reagents applied directly to the tumor to modify the immunosuppressive microenvironment so that the immune system is able to effectively respond against the tumors. This example shows that inhalation of a self-assembling virus-like particle derived from cowpea mosaic virus (CPMV) suppresses the development of tumors in the lungs of mice after intravenous challenge. The disparity in tumor burden between CPMV- and PBS-treated mice was pronounced, and the effect was immune-mediated as it was not seen in Ifn-$\gamma_{-/-}$, Il-12$^{-/-}$, or NOD/scid/Il2R$\gamma^{-/-}$ mice. Efficacy was also lost in the absence of Ly6G$^+$ cells. CPMV nanoparticles were rapidly taken up by granulocytic cells in the tumor microenvironment and resulted in their robust activation and cytokine/chemokine production. CPMV nanoparticles are stable, nontoxic, highly scalable, and modifiable with drugs and antigens. These properties, combined with their inherent immunogenicity and significant efficacy against a poorly immunogenic tumor, present CPMV as an attractive novel immunotherapy against cancer metastatic to the lung. Additionally, CPMV exhibited clear treatment efficacy in various other tumor models including dermal melanoma, metastatic breast, colon, and ovarian cancers.

Materials and Methods eCPMV Production and Characterization eCPMV capsids were produced through agroinfiltration of *Nicotiana benthamiana* plants with a culture of *Agrobacterium tumefaciens* LBA4404 transformed with the binary plasmid pEAQexpress-VP60-24K, which contains genes for the coat protein precursor VP60 and its 24K viral proteinase to cleave it into its mature form. 6 days post infiltration, the leaves were harvested and eCPMV extracted using established procedures. The particle concentration was measured using UV/vis spectroscopy ($\varepsilon_{280\ nm}$=1.28 mg$^{-1}$ mL cm$^{-1}$), and particle integrity was determined by transmission electron microscopy and fast protein liquid chromatography.

Mice

C57BL/6J (01055) females were purchased from the National Cancer Institute or The Jackson Laboratory. Il-12p35$^{-/-}$ (002692), Ifn-$\gamma^{-/-}$ (002287), BALB/c (000651), and NOD/scid/Il2R$\gamma^{-/-}$ (005557) female mice were purchased from The Jackson Laboratory. All mouse studies were performed in accordance with the Institutional Animal Care and Use Committee of Dartmouth.

Tumor Models

The B16F10 murine melanoma cell line was obtained from Dr. David Mullins (Geisel School of Medicine at Dartmouth College, Hanover, N.H.). 4T1-luciferase murine mammary carcinoma cells were provided by Ashutosh Chilkoti (Duke University, Durham, N.C.). B16F10, 4T1-luc, and CT26 were cultured in complete media (RPMI supplemented with 10% FBS and penicillin/streptomycin). ID8-Defb29/Vegf-A orthotopic ovarian serous carcinoma cells were cultured in complete media supplemented with sodium-pyruvate as previously described. Lizotte et al., Oncoimmunology, 3:e28926. eCollection 2014. Cells were harvested, washed in phosphate-buffered saline (PBS), and injected in the following manner depending on tumor model: $1.25 \times 10^5$ live cells injected intravenously in 200 µL PBS in the tail vein (B16F10 metastatic lung), $1.25 \times 10^5$ live cells injected intradermally in 30 µL PBS in the right flank (B16F10 flank), $1 \times 10^5$ live cells injected intradermally in 30 µL PBS in the right flank (CT26 flank), $2 \times 10^6$ live cells injected intraperitoneally in 200 µL PBS (ID8-Defb29/Vegf-A peritoneal ovarian). For 4T1-luc tumor challenge, $1 \times 10^5$ live cells were injected in 30 µL of PBS into the left mammary fat pad on day 0 and the tumor was surgically removed on day 16, a day by which it is well-established that the tumor has spontaneously metastasized to the lung. Complete removal of primary 4T1-luc tumors was confirmed by bioluminescent imaging. B16F10 and ID8-Defb29/Vegf-A are syngeneic for the C57BL6J strain, whereas CT26 and 4T1-luc are syngeneic for the BALB/c background.

eCPMV Treatment Scheduling

WT, Il-12$^{-/-}$, Ifn-$\gamma^{-/-}$, NOD/scid/IL2R$\gamma^{-/-}$, and Ly6G-depleted mice challenged intravenously with B16F10 were intubated and intratracheally injected with 100 µg of eCPMV in 50 µL PBS on days 3, 10, and 17 post-tumor challenge. For lung challenge experiments, mice were euthanized on day 21 for quantification of metastatic-like lesions and tyrosinase expression. 4T1-luc-bearing mice were intratracheally injected with 20 µg of eCPMV in 50 µL PBS on day 16 (same day as primary tumor removal) and again on day 23 (day 7 post-tumor removal). B16F10 flank tumors were intratumorally injected with 100 µg eCPMV on day 7 post-tumor challenge once tumors had reached 10 mm$^2$ and again on day 14. CT26 flank tumors were intratumorally injected with 100 µg eCPMV on day 8 post-tumor challenge once they had reached 10 mm$^2$ and again on day 15. Flank tumor diameters were measured every other day and mice were euthanized when tumor diameters reached 200 mm$^2$. ID8-Defb29/Vegf-A mice were injected IP with 100 µg of eCPMV weekly beginning on day 7 post-tumor challenge and euthanized when they reached 35 g due to ascites development.

Antibodies and Flow Cytometry

Anti-mouse antibodies were specific for CD45 (30-F11), MHC-II (M5/114.15.2), CD86 (GL-1), CD11b (M1/70), F4/80 (BM8), and Ly6G (1A8) from Biolegend and CD16/CD32 (93) from eBioscience. WT and B16F10 lung tumor-bearing mice were intratracheally injected with 100 µg Alexa-488-labeled CPMV particles 24 hr prior to euthanization. Lungs were harvested and dissociated into single cell suspension using the Miltenyi mouse lung dissociation kit (cat #130-095-927). Red blood cells were removed using lysis buffer of 150 mM NH4Cl, 10 mM KHCO3, and 0.5 mM EDTA. Flow cytometry was performed on a MACSQuant analyzer (Miltenyi). Data were analyzed using FlowJo software version 8.7.

Tyrosinase mRNA Expression Analysis

Whole lungs were dissociated and total RNA was extracted using the RNeasy kit (Qiagen, 74104). cDNA was synthesized using iScript™ cDNA synthesis kit (Bio-Rad, 170-8891). q-PCR was performed on a CFX96™ Real-Time PCR Detection System (Bio-Rad) using iQ™ SYBR® Green Supermix (Bio-Rad, 170-8882) with primers at a concentration of 0.5 µM. mRNA transcript fold-change was calculated using the ΔΔCT method with all samples normalized to mouse Gapdh.

Cytokine Assay

For in vivo cytokine data, total lung homogenate was harvested from B16F10 lung tumor-bearing mice 24 hr post-inhalation of 100 µg eCPMV particles, which was day 8 post-tumor challenge. For in vitro cytokine results, bone marrow-derived dendritic cells (BMDCs) and thioglycollate-stimulated peritoneal macrophages, both derived from C57BL6 mice, were cultured at $1 \times 10^6$ cells/well in 200 µL complete media in 96-well round-bottomed plates with either 20 µg of eCPMV or PBS. Supernatant was harvested after 24 hr incubation. Cytokines were quantified using mouse 32plex Luminex assay (MPXMCYTO70KPMX32, Millipore).

Cell Depletion

Mice were injected with mAb depleting Ly6G (clone 1A8) that was purchased from Bio-X-Cell (cat #BE0075-1) and administered IP in doses of 500 µg one day prior to eCPMV treatment and then once weekly for the duration of survival experiments. Greater than 95% depletion of target cell populations in the lung was confirmed by flow cytometry.

IVIS Imaging

Mice were injected IP with 150 mg/kg of firefly D-luciferin in PBS (PerkinElmer cat #122796) and allowed to rest for 10 min Imagining was conducted using the Xenogen VivoVision IVIS Bioluminescent and Fluorescent Imager platform and analyzed with Living Image 4.3.1 software (PerkinElmer).

Statistics

Unless noted otherwise, all experiments were repeated at least 2 times with 4-12 biological replicates and results were similar between repeats. Figures denote statistical significance of $p<0.05$ as *, $p<0.01$ as , and $p<0.001$ as *. A p-value $<0.05$ was considered to be statistically significant. Data for bar graphs was calculated using unpaired Student's t-test. Error bars represent standard error of the mean from independent samples assayed within the represented experiments. Flank tumor growth curves were analyzed using two-way ANOVA. Survival experiments utilized the log-rank Mantel-Cox test for survival analysis. Statistical analysis was done with GraphPad Prism 4 software.

Results eCPMV Nanoparticles are Inherently Immunogenic

In this Example, eCPMV (eCPMV refers to "empty" cowpea mosaic virus particle devoid of RNA) was used as a novel immunotherapy. eCPMV VLPs were added to in vitro cultures of bone marrow-derived dendritic cells (BMDCs) and primary macrophages harvested from C57BL6 mice. Twenty-four hours of culture with eCPMV particles induced both BMDCs (FIG. 1A) and macrophages (FIG. 1B) to secrete higher levels of canonical pro-inflammatory cytokines including Il-β, Il-6, Il-12p40, Ccl3 (MIP1-α), and Tnf-α, leading the inventors to conclude that eCPMV is inherently immunostimulatory.

eCPMV Inhalation Radically Alters the B16F10 Lung Tumor Microenvironment

The immunomodulatory effect of eCPMV inhalation on the lung microenvironment was determined next, both in terms of immune cell composition and changes in cytokine and chemokine levels. Exposure of non-tumor-bearing mouse lungs to eCPMV revealed significant activation of Ly6G$^+$ neutrophils 24 hours after exposure as assessed by their upregulation of the CD11b activation marker. (FIG. 2A top panels) and CD86 co-stimulatory marker. Alexa488-labeling of the particle allowed for cell tracking, which enabled the inventors to confirm that it is this CD11b$^+$Ly6G$^+$ activated neutrophil subset, specifically, that takes up the eCPMV.

Figure 2C:
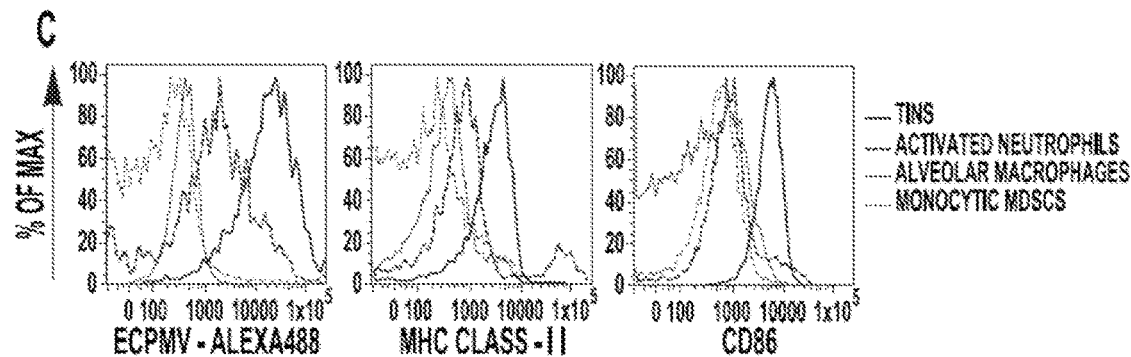

Lungs of mice bearing B16F10 melanoma tumors revealed a more complex immune cell composition. By day 7 the emergence of large populations of immunosuppressive CD11b$^+$Ly6G$^-$F4/80$^{lo}$class-II$^-$SSC$^{lo}$ monocytic myeloid-derived suppressor cells (MDSCs) and CD11b$^+$Ly6G$^+$F4/80$^-$class-II$^{mid}$SSC$^{hi}$ granulocytic MDSCs (FIG. 2A bottom panels) could be observed. The inventors also observed the presence of a small population of CD11b$^+$Ly6G$^+$class-II$^{mid}$CD86$^{hi}$ cells that have been described in the literature as "tumor-infiltrating neutrophils" or "N1 neutrophils" that are known to exert an anti-tumor effect through coordination of adaptive immune responses, production of high levels of pro-inflammatory cytokines, recruitment of T and NK cells, and direct cytotoxicity to tumor cells. Fridlender et al., Cancer Cell. 16(3):183-94 (2009); Mantovani et al., Nat Rev Immunol. (8):519-31 (2011). Inhalation of eCPMV into B16F10-bearing lungs dramatically altered the immune cell composition 24 hours after administration. Significant increases in the tumor-infiltrating neutrophil (TIN) and CD11b$^+$Ly6G$^+$ activated neutrophils populations, as well as a reduction in CD11b$^-$Ly6G$^+$ quiescent neutrophils (FIG. 2A bottom panels, see arrows) were also observed. TIN and activated CD11b$^+$ neutrophil populations increased dramatically both as a percentage of CD45$^+$ cells and also in total number (FIG. 2B). Interestingly, it is these neutrophil subpopulations that took up the vast majority of eCPMV particles, particularly TINs that took up 10-fold more eCPMV than CD11b$^+$activated neutrophils (FIG. 2C). Monocytic MDSC, quiescent neutrophil, and alveolar macrophage populations did not take up eCPMV, and granulocytic MDSCs displayed uneven uptake. The TIN and activated neutrophil populations also expressed MHC class-II, and the TINs, in particular, displayed high levels of co-stimulatory marker CD86, indicating potential antigen presentation and T cell priming capability. Significant changes were not observed in the numbers of monocytic or granulocytic MDSCs.

Figure 2D:
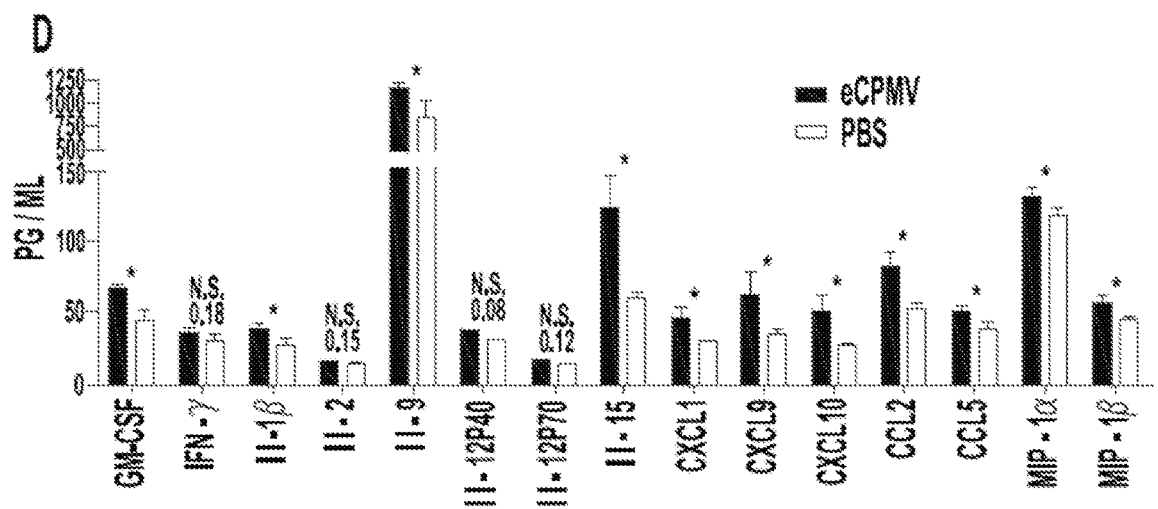

Activation of neutrophil populations by eCPMV is consistent with data collected from a multiplexed cytokine/chemokine array performed on whole lung homogenate of B16F10 tumor-bearing lungs treated with eCPMV or PBS (FIG. 2D). Specifically, significant increases in neutrophil chemoattractants GM-CSF, Cxcl1, Ccl5, and MIP-1α and significant increases in cytokines and chemokines known to be produced by activated neutrophils such as GM-CSF, Il-1β, Il-9, Cxcl1, Cxcl9, Cxcl10, Ccl2, MIP-1α, and MIP-1β were seen. Interestingly, the inventors did not observe significant increases in levels of Il-6 or Tnf-α, which are classical pro-inflammatory cytokines which may be detrimental in the context of lung immunobiology.

eCPMV Inhalation Suppresses B16F10 Metastatic-Like Lung Tumor Development

Figure 3A:
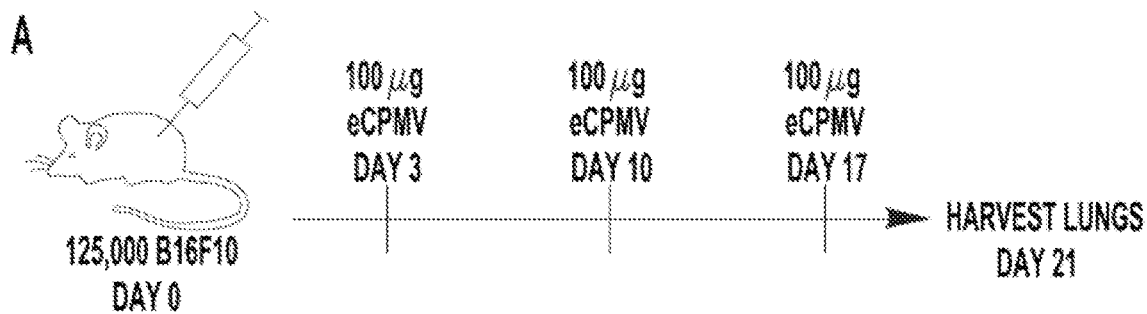
FIGS. 3A-3D provide graphs and images showing eCPMV inhalation prevents formation of B16F10 metastatic-like lung tumors. (A) Schematic of experimental design. (B) Photographic images of lungs from eCPMV- and PBS-treated B16F10 tumor-bearing mice on day 21 post-tumor challenge. (C and D) B16F10 lung metastatic-like tumor foci were quantified both by number in (C) or by qRT-PCR assay for melanocyte-specific Tyrp1 mRNA expression in (D).
Figure 3B:
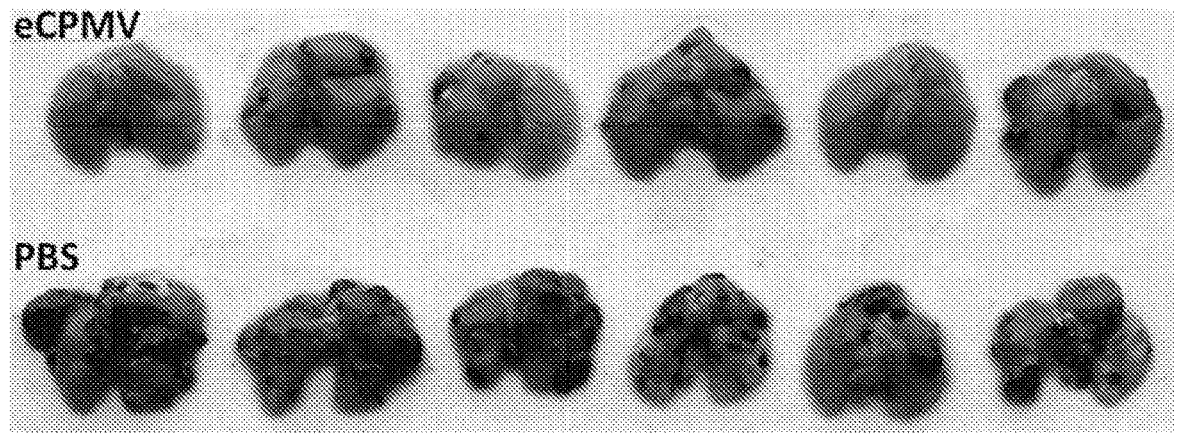
Figure 3C:
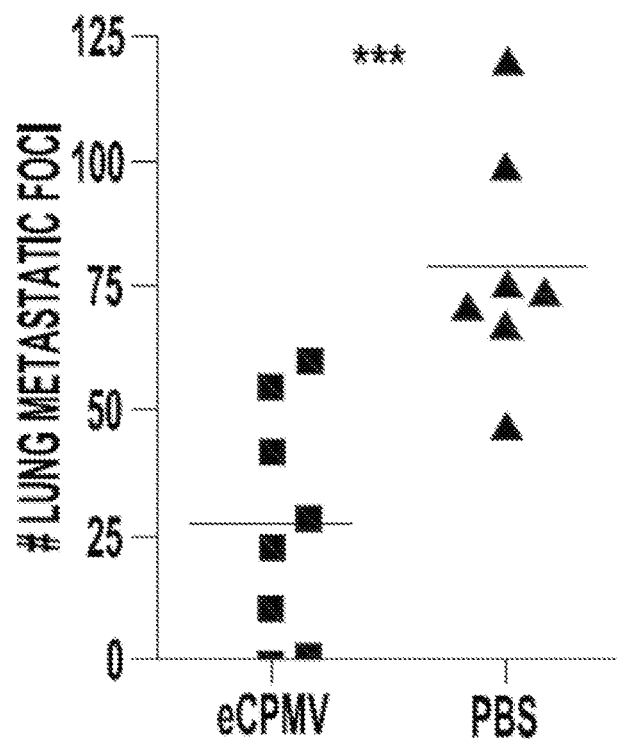
Figure 3D:
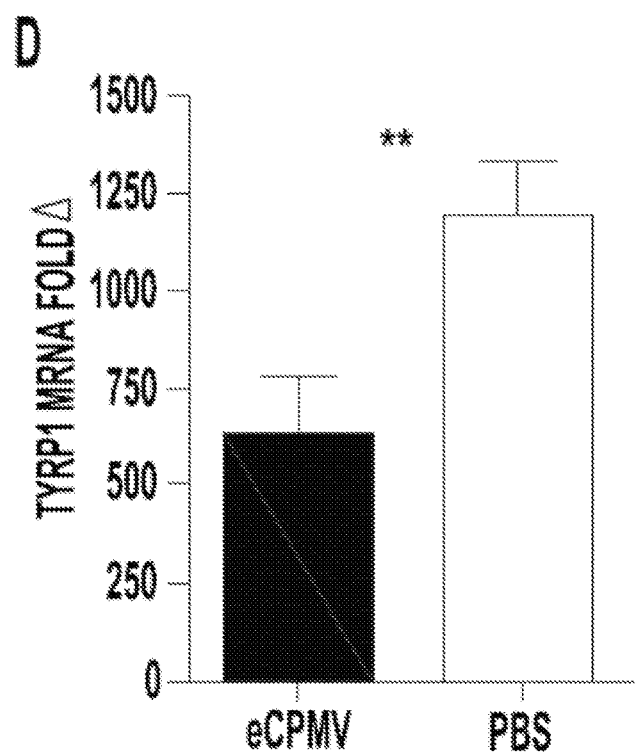

The inventors next investigated whether the inherent immunogenicity of the eCPMV particle in the lung could induce anti-tumor immunity in the B16F10 intravenous model of aggressive metastatic lung cancer. Indeed, weekly intratracheal injection of 100 μg of eCPMV (FIG. 3A) resulted in significantly reduced tumor burden as assessed by both metastatic-like tumor foci number (FIGS. 3, B and C) and tyrosinase expression (FIG. 3D). Tyrosinase-related protein 1 (Tyrp1) is a melanocyte-specific gene (Zhu et al., Cancer Res., 73(7):2104-16 (2013)) whose expression in the lung is restricted to B16F10 tumor cells, which allows for the quantitative measure of tumor development and serves as a control for the varying sizes of metastatic-like foci.

Anti-Tumor Efficacy of eCPMV Inhalation is Immune-Mediated

Figure 4A:
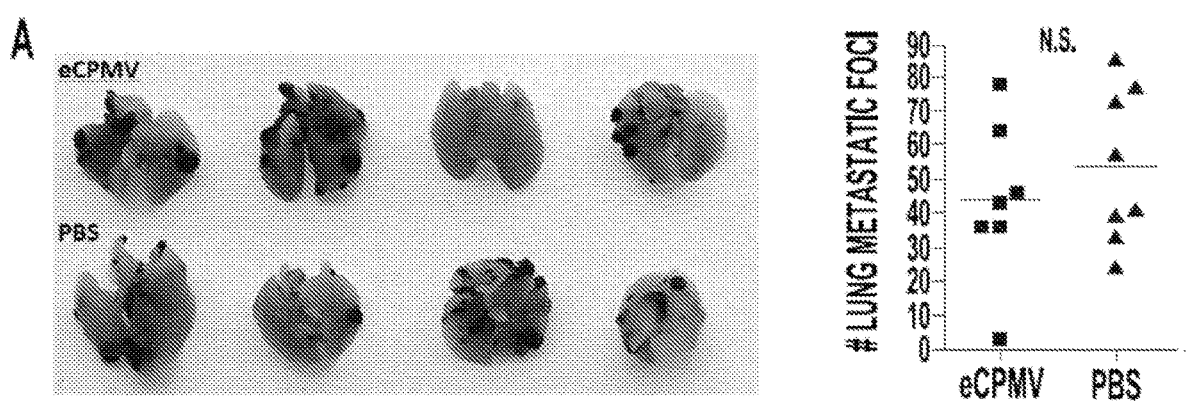

The inventors determined whether the immune system was required for treatment efficacy by repeating their experimental design described in FIG. 3 in the following transgenic mice: Il-12$^{-/-}$, Ifn-γ$^{-/-}$, and NOD/scid/IL2Rγ$^{-/-}$. A significant difference in lung tumor burden between eCPMV- and PBS-treated mice was not observed in the absence of Il-12 (FIG. 4A), Ifn-γ (FIG. 4B), or in NSG mice lacking T, B, and NK cells (FIG. 4C).

eCPMV accumulates in and activates neutrophils in the lungs of B16F10 tumor-bearing mice (FIG. 2, A to C). Additionally, significant increases in neutrophil-associated cytokines and chemokines were detected in the mouse lung following eCPMV inhalation (FIG. 2D). Therefore, neutrophils were depleted using a monoclonal antibody to assess the necessity of neutrophils for treatment efficacy. Depletion of neutrophils from the lungs of tumor-bearing mice abrogated the anti-tumor effect that we observed in WT mice. This, combined with the lack of efficacy observed in Il-12$^{-/-}$, Ifn-γ$^{-/-}$, and NSG mice leads the inventors to conclude that the anti-tumor effect of eCPMV inhalation on B16F10 development is through immunomodulation of the lung tumor microenvironment and, in particular, requires the presence of the neutrophil compartment.

eCPMV Anti-Tumor Efficacy is not Restricted to the B16F10 Intravenous Lung Model The inventors sought to ascertain whether eCPMV treatment efficacy was restricted to the B16F10 metastatic lung model or if the immunomodulatory anti-tumor effect could transfer to other models. The 4T1 BALB/c syngeneic breast cancer model, which is a transferrable yet truly metastatic model, was first utilized. 4T1 tumors established in the mammary fat pad spontaneously metastasize to the lung by day 16, at which point the primary tumor was surgically removed and eCPMV treatment begun, injecting intratracheally to affect lung tumor development. The 4T1 cells also expressed luciferase, allowing the inventors to track metastatic lung tumor development. Mice treated intratracheally with eCPMV particles had significantly delayed lung tumor onset and significantly extended survival (FIG. 5A). Mice from eCPMV and PBS treatment groups had comparable primary mammary fat pad tumor burden at day of surgical removal. Therefore, differences in tumor development and survival were due to treatment. No mice from either group experienced recurrence of primary mammary fat pad tumors.

Figure 5B:
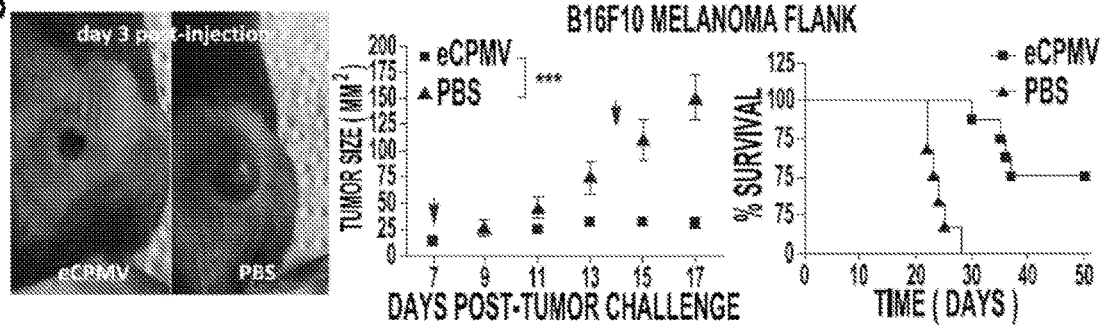
Figure 5C:
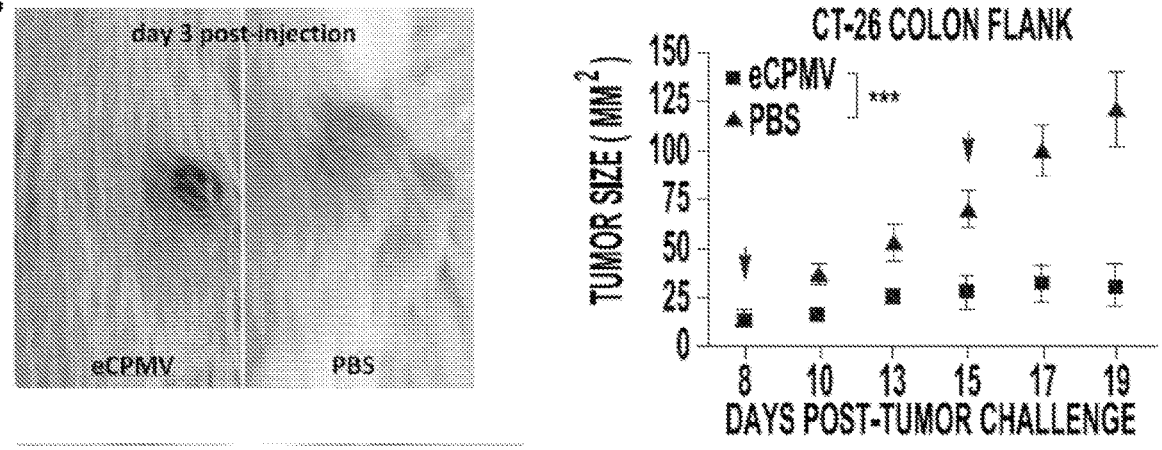

To determine whether the eCPMV particle's unambiguous efficacy in B16F10 and 4T1 metastatic lung models was unique to the lung immune environment, its ability to treat dermal tumors was also tested. Both intradermal B16F10 melanoma (FIG. 5B) and CT26 colon (FIG. 5C) tumor growth was significantly delayed following direct injection with eCPMV and, in half of the B16F10 eCPMV-treated mice, resulted in elimination of the tumors altogether after only two treatments (FIG. 5B).

Figure 5D:
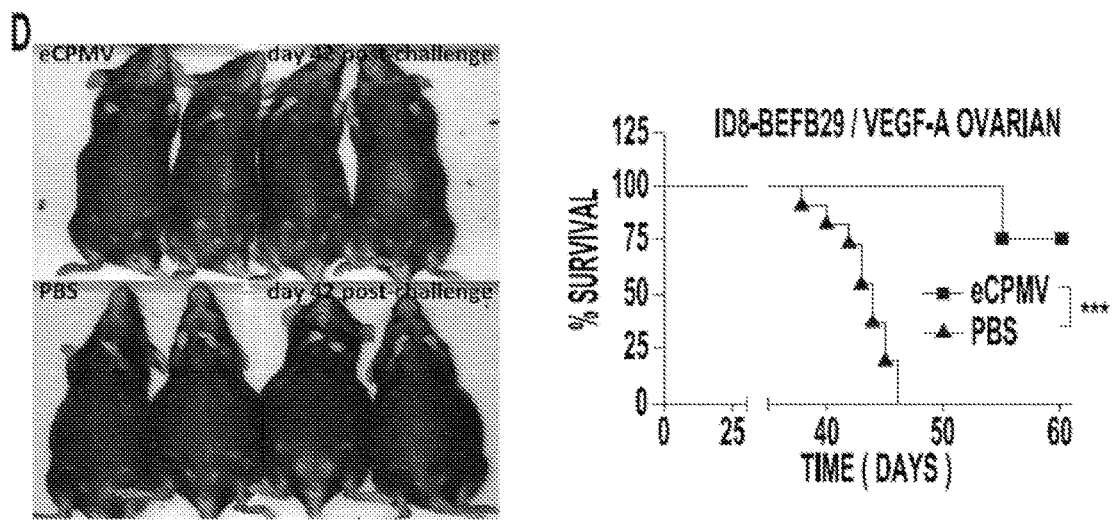

Finally, the therapeutic effect of eCPMV was investigated in a model of disseminated peritoneal serous ovarian carcinoma. Conejo-Garcia et al., Nat Med., (9):950-8 (2004). ID8-Defb29/Vegf-A-challenged mice treated weekly with eCPMV exhibited significantly improved survival relative to PBS-treated controls (FIG. 5D). In fact, mice receiving eCPMV survived longer in comparison than other immunotherapies attempted in this model including a live, attenuated *Listeria monocytogenes* strain (Lizotte et al., Oncoimmunology, 3:e28926. eCollection 2014), avirulent *Toxoplasma gondii* (Baird et al., Cancer Res., 73(13):3842-51 (2013)), combination agonistic CD40 and poly(I:C) (Scarlett et al., Cancer Res., 69(18):7329-37 (2009)), or 11-10 blocking antibody (Hart et al., T Cell Biol., 2:29 (2011)). It is important to note that the anti-tumor effects of eCPMV in the tested models are not attributable to direct tumor cell cytotoxicity, as exposure to high concentrations of the particle in vitro had no effect on cancer cell viability or proliferation. The logical conclusion is that the striking anti-tumor effect induced by eCPMV nanoparticle treatment is fully immune-mediated and translatable to a variety of tumor models across diverse anatomical sites.

eCPMV nanoparticles are immunotherapeutic to a surprisingly high degree and clearly modulate the tumor immune environment. BMDCs and macrophages exposed to the particles robustly secreted select pro-inflammatory cytokines (FIGS. 1A and B). eCPMV particles were produced in plants, then plant contaminants were extracted using polyvinyl-polypyrrolidone, eCPMV isolated through PEG precipitation and sucrose gradient ultracentrifugation, and finally the particles concentrated by ultrapelleting. Purity was checked by UV/Vis absorbance, transmission electron microscopy (TEM), fast protein liquid chromatography (FPLC), and SDS gel electrophoresis. Wen et al., Biomacromolecules, 13(12):3990-4001 (2012). No contaminants were detected during these procedures. Particles were then resuspended in PBS. Additionally, eCPMV is completely devoid of RNA that could stimulate TLR3/7. The inventors therefore conclude that the high immunogenicity of eCPMV is due to the size, shape, or inherent immune recognition of the viral coat protein. This is unlike virus-like or protein cage nanoparticles that are manufactured in *E. coli* or other systems that may contain immunogenic contaminants like endotoxin or viral nucleic acids that are challenging to remove during the purification process.

eCPMV inhalation transforms the lung tumor microenvironment and requires the presence of Ly6G$^+$ neutrophils, a population that is minimally associated with response to tumor immunotherapy. Notably, eCPMV particles appear to specifically target Ly6G$^+$ neutrophils. eCPMV has been shown to bind surface vimentin on cancer cells (Steinmetz et al., Nanomed. 6(2):351-64 (2011)) and some antigen-presenting cells (Gonzalez et al., PLoS ONE. 4(11):e7981 (2009)), although it is not known if this is the mechanism by which lung-resident neutrophils are internalizing the particle, or if surface expression of vimentin is a feature of murine neutrophils. eCPMV appears to target quiescent neutrophils and convert them to an activated CD11b$^+$ phenotype, as well as inducing the recruitment of additional CD11b$^+$ activated neutrophils and CD11b$^+$class-II$^+$CD86$^{hi}$ tumor-infiltrating neutrophils. In fact, these two populations—activated neutrophil and tumor-infiltrating or "N1" neutrophils—are the only innate immune cell populations that significantly change rapidly following eCPMV lung exposure, both dramatically increasing as a percentage of CD45$^+$ cells and in total cell number (FIG. 2B). Neutrophils are viewed canonically as sentinels for microbial infection that quickly engulf and kill bacteria before undergoing apoptosis, yet they have an emerging roll in tumor immunology. Although still controversial, it appears that neutrophils possess phenotypic plasticity analogous to the M1/M2 polarization accepted in macrophage literature. Studies have shown infiltration of an immunosuppressive, pro-angiogenic "tumor-associated neutrophil" population in B16F10 metastatic lung, human liver cancer, sarcoma, and lung adenocarcinoma models that is correlated with enhanced tumor progression. Alternatively, depletion of tumor-resident immunosuppressive neutrophils, conversion of them to a pro-inflammatory phenotype, or recruitment of activated neutrophils to infiltrate the tumor microenvironment is associated with therapeutic efficacy. Activated neutrophils can directly kill tumor cells via release of reactive oxygen intermediates (ROI), prime CD4$^+$ T cells and polarize them to a Th1 phenotype, cross-prime CD8$^+$ T cells, and modulate NK cell survival, proliferation, cytotoxic activity and IFN-$\gamma$ production. Activated neutrophils can also produce Cxcr3 ligands Cxcl9 and Cxcl10 that can recruit CD4$^+$ and CD8$^+$ T cells that are correlated with anti-tumor immunotherapeutic efficacy in melanoma models. The data showing increases in immunostimulatory neutrophil populations (FIG. 2B) agrees with the cytokine data (FIG. 2D), in which increases in neutrophil chemoattractants GM-CSF, Cxcl1, Ccl5, and MIP-1$\alpha$ and cytokines and chemokines known to be produced by neutrophils were observed, including GM-CSF, Il-1$\beta$, Il-9, Cxcl1, Cxcl9, Cxcl10, Ccl2, MIP-1$\alpha$, and MIP-1$\beta$. This data in turn agrees with the in vivo tumor progression data showing that neutrophils are required for eCPMV anti-tumor efficacy. Interestingly, although many cytokine and chemokine levels were elevated to a statistically significant degree following eCPMV treatment, changes were modest when compared to the dramatic differences in actual tumor burden (FIG. 3, B to D). Moreover, increases in pro-inflammatory cytokines Tnf-$\alpha$ or Il-6 that are known to cause tissue damage when upregulated in the lung were not observed. It appears, therefore, that eCPMV treatment of lung tumors is effective without eliciting the kind of inflammatory cytokine response that could cause acute lung injury.

eCPMV inhalation exhibited remarkable efficacy as a monotherapy (FIG. 3) that is very clearly immune-mediated (FIG. 4). This is novel because the eCPMV particle does not directly kill tumor cells or share any antigenic overlap with B16F10 tumors, but induces an anti-tumor response that requires Th1-associated cytokines 11-12 (FIG. 4A) and Ifn-$\gamma$ (FIG. 4B), adaptive immunity (FIG. 4C), and neutrophils. This suggests that the inherent immunogenicity of eCPMV, when introduced into the lung, disrupts the tolerogenic nature of the tumor microenvironment; in essence, removing the brakes on a pre-existing anti-tumor immune response that is suppressed, or allowing a de novo anti-tumor response to develop.

This work also shows that eCPMV anti-tumor efficacy in the intravenous B16F10 metastatic lung model is not an artifact of the C57BL6 mouse strain or the B16F10 model, as eCPMV therapy works equally impressively in flank B16F10, ovarian carcinoma, and two BALB/c models of metastatic breast and colon cancer (FIG. 5). Constitutive luciferase expression in 4T1 breast carcinoma cells and intradermal challenges of B16F10 and CT26 allowed us to measure tumor progression quantitatively in a manner not feasible in the B16F10 lung model. It is in these models that we observed a potent and immediate anti-tumor effect that significantly delayed tumor progression and, in the cases of the B16F10 and CT26 intradermal tumors, induced rapid involution of established tumors and formation of necrotic centers (FIGS. 5, B and C) that remained confined to within the margins of the tumors and did not appear to affect surrounding tissue. Such early responses to eCPMV—day 3 post-intratumoral injection—would indicate that eCPMV particles are inducing innate immune cell-mediated anti-tumor responses. The eCPMV nanoparticle, alone, is immunogenic and highly effective as a monotherapy. However, it can also serve as a nanocarrier for tumor antigens, drugs, or immune adjuvants, opening up the exciting possiblity that eCPMV can be modified to deliver a payload that further augments and improves its immunotherapeutic efficacy.

Example 2 eCPMV Treatment of Dermal B16F10 is Inducing Systemic Anti-Tumor Immunity

Figure 6A:
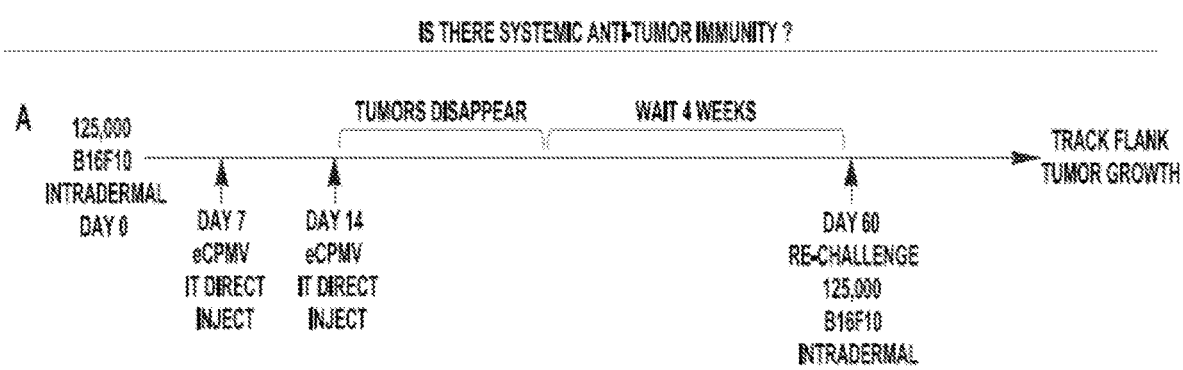
FIGS. 6A and 6B provide a timechart (A) and a graph (B) showing eCPMV treatment of dermal B16F10 induces systemic anti-tumor immunity.
Figure 6B:
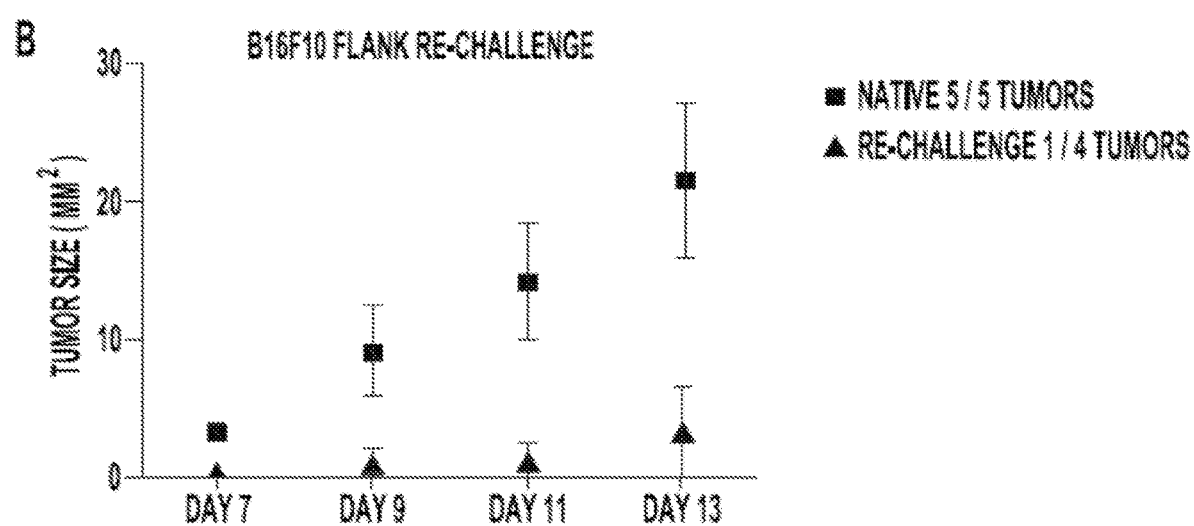
Figure 7A:
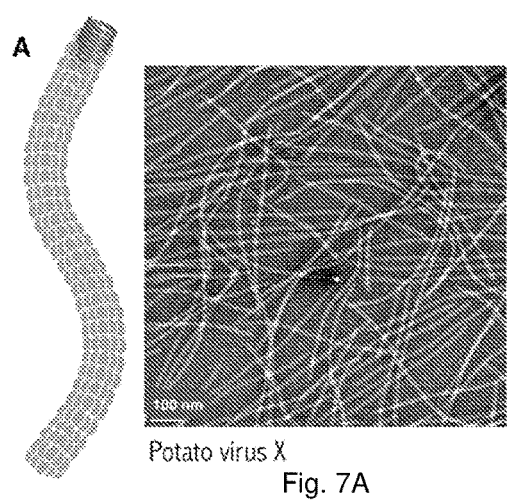
FIGS. 7A-D are a schematic and transmission electron micrographs of (A) PVX and (B) CPMV. C+D) Tumor treatment study. Tumors were induced with an intradermal injection of 125,000 cells/mouse. Mice (n=3) were treated with 100 μg of PVX or CPMV (or PBS control) once weekly, starting 8 days post-induction. Arrows indicate injection days; mice were sacrificed when tumor volumes reached 1000 mm3. (C) Tumor growth curves shown as relative tumor volume. (D) Survival rates of treated mice.
Figure 7B:
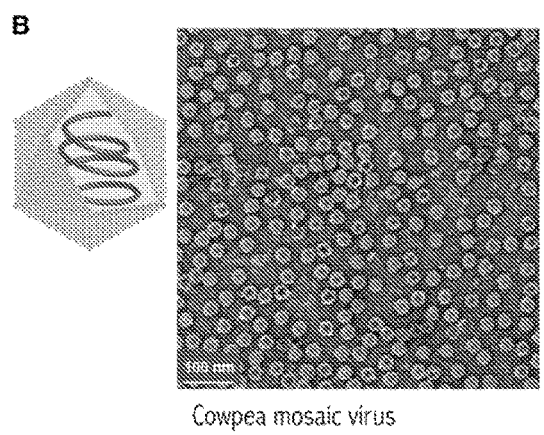
Figure 7C:
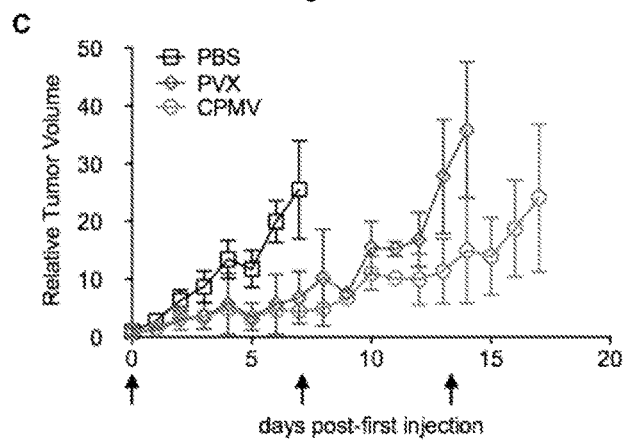
Figure 7D:
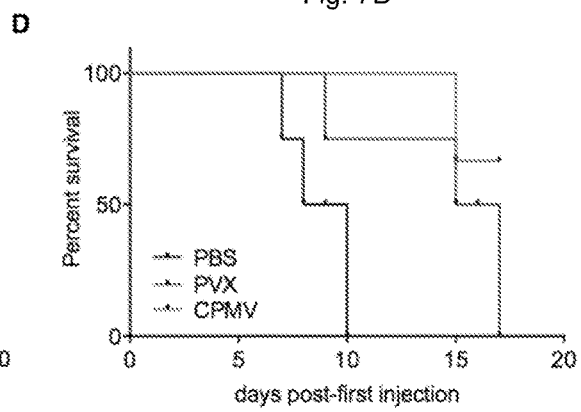

As shown in FIG. 6, the inventors established dermal melanoma tumors and injected the eCPMV particles directly into them (100 µg/injection, arrows indicate injection days). In half of the mice this results in complete disappearance of the tumors. In the cured mice, we then waited 4 weeks and re-challenged with the same tumor cells, but we injected tumor cells on the opposite flank. Most of those mice did not develop secondary tumors. To clarify: primary tumors were directly injected with particles, whereas mice bearing secondary tumors received no treatment. They had to rely on systemic anti-tumor immune memory alone. The eCPMV was applied locally in the first tumors, but induced systemic immunity. "Re-challenge" mice where those that previously had B16F10 dermal tumors that were direct-injected and that shrank and disappeared.

Example 3

Using a plant virus-based nanotechnology, we demonstrated that virus like particles (VLPs) from the icosahedral virus cowpea mosaic virus (CPMV, 30 nm in diameter) stimulate a potent anti-tumor immune response when applied as an in situ vaccine. Efficacy was demonstrated in mouse models of melanoma, breast cancer, ovarian cancer, and colon cancer. Data indicate that the effect is systemic and durable, resulting in immune-memory and protecting subjects from recurrence. While the underlying mechanism has not been elucidated in depth, initial studies, in which VLPs were inhaled into the lungs of mice bearing B16F10 lung tumors, revealed a sub-population of lung antigen presenting cells (APC) that are MHC class II+ CD11b+ Ly6G+ neutrophils that ingest VLPs and activate following VLP exposure. Further, the increase in this neutrophil population is accompanied by a decrease of myeloid-derived suppressor cells (MDSCs) that mediate immune-suppression in the tumor microenvironment. Here we set out to investigate the use of plant viruses as in situ vaccines and their combination with chemotherapy regimes.

Recent clinical and preclinical research indicates that the combination of chemo- and immunotherapies can be beneficial because the therapy regimes can synergize to potentiate the therapy and improve patient outcomes. For chemo-immuno combination treatment, the use of the anthracycline doxorubicin (DOX) could be a particularly powerful approach, because 6 DOX itself induces immunogenic cell death that elicits an antitumor immune response. The immune response is induced by calreticulin exposure on the surface of dying cells, which facilitates tumor cell phagocytosis by dendritic cells resulting in tumor antigen presentation. Furthermore, doxorubicin-killed tumor cells recruit intratumoral CD11c+ CD11b+ Ly6Chi myeloid cells, which present tumor antigens to T lymphocytes; therefore, the combination of doxorubicin with tumor vaccines or immunotherapies can synergize and potentiate the overall efficacy.

In this example, we set out to address the following questions:
i) whether the flexuous particles formed by the potato virus X (PVX) would stimulate an anti-tumor response when used as in situ vaccine?
ii) whether the combination of VLP-based in situ vaccine with DOX chemotherapy would potentiate therapeutic efficacy; specifically we asked whether the formulation as combinatorial nanoparticle where DOX is bound and delivered by PVX (PVX-DOX) or the co-administration of the therapeutic regimens (PVX+DOX) would be the most effective treatment strategy?

All studies were performed using a mouse model of melanoma.

Methods

PVX and CPMV Production

PVX was propagated in *Nicotiana benthamiana* plants and purified as previously reported. CPMV was propagated in *Vigna unguiculata* plants and purified as previously reported.

Synthesis of PVX-DOX

PVX (2 mg mL-1 in 0.1 M potassium phosphate buffer (KP), pH 7.0) was incubated with a 5,000 molar excess of doxorubicin (DOX) at a 10% (v/v) final concentration of DMSO for 5 days at room temperature, with agitation. PVX-DOX was purified twice over a 30% (w/v) sucrose cushion using ultracentrifugation (212,000×g for 3 h at 4° C.) and resuspended overnight in 0.1 M KP, pH 7.0. PVX-DOX filaments were analyzed using UV/visible spectroscopy, transmission electron microscopy, and agarose gel electrophoresis.

UV/Visible Spectroscopy

The number of DOX per PVX filament was determined by UV/visible spectroscopy, using the NanoDrop 2000 spectrophotometer. DOX loading was determined using 20 the Beer-Lambert law and DOX (11,500 $M^{-1}$ $cm^{-1}$ at 495 nm) and PVX (2.97 mL $mg^{-1}$ $cm^{-1}$ at 260 nm) extinction coefficients.

Transmission Electron Microscopy (TEM)

TEM imaging was performed after DOX loading to confirm integrity of PVX-DOX filaments. PVX-DOX samples (0.1 mg $mL^{-1}$, in dH$_2$O) were placed on carbon-coated copper grids and negatively stained with 0.2% (w/v) uranyl acetate. Grids were imaged using a Zeiss Libra 200FE transmission electron microscope, operated at 200 kV.

Agarose Gel Electrophoresis

To confirm DOX attachment, PVX-DOX filaments were run in a 0.8% (w/v) agarose gel (in TBE). PVX-DOX and corresponding amounts of free DOX or PVX alone were loaded with 6× agarose loading dye. Samples were run at 100 V for 30 min in TBE. Gels were visualized under UV light and after staining with 0.25% (w/v) Coomassie blue.

Cell Culture and Cell Viability Assay

B16F10 cells (ATCC) were cultured in Dulbecco's modified Eagle's media (DMEM, Life Technologies), supplemented with 10% (v/v) fetal bovine serum (FBS, Atlanta Biologicals) and 1% (v/v) penicillin-streptomycin (penstrep, Life Technologies). Cells were maintained at 37° C., 5%

$CO_2$. Confluent cells were removed with 0.05% (w/v) trypsin-EDTA (Life Technologies), seeded at 2×10³ cells/100 μL/well in 96-well plates, and grown overnight at 37° C., 5% $CO_2$. The next day, cells were washed 2 times with PBS and incubated with free DOX or PVX-DOX corresponding to 0, 0.01, 0.05, 0.1, 0.5, 1, 5, or 10 μM DOX for 24 h, in triplicate. A PVX only control corresponded to the amount of PVX in the highest PVX-DOX sample. Following incubation, cells were washed 2 times to remove unbound DOX or particles. Fresh medium (100 μL) was added and cells were returned to the 21 incubator for 48 h. Cell viability was assessed using an MTT proliferation assay (ATCC); the procedure was as the manufacturer suggested.

Animal Studies

All experiments were conducted in accordance with Case Western Reserve University's Institutional Animal Care and Use Committee. C57BL/6J male mice (Jackson) were used. B16F10 tumors were induced intradermally into the right flank of C57BL/6J mice (1.25×10⁵ cells/50 μL media). Animals were monitored and tumor volume was calculated as V=0.5×a×b2, where a=width of the tumor and b=length of the tumor. Animals were sacrificed when tumor volume reached >1000 mm3 Treatment schedule: Eight days post-tumor induction (day 0), mice were randomly assigned to the following groups (n=3): PBS, PVX, or CPMV. Mice were treated intratumorally (20 μL), every 7 days, with 5 mg kg-1 PVX or CPMV. Mice were sacrificed when tumors reached a volume >1000 mm³. For chemo-immunotherapy combination therapy, mice were randomly assigned to the following groups (n=6): PBS, PVX, DOX, conjugated PVX-DOX, or PVX+DOX mixtures. PVX+DOX samples were prepared less than 30 min before injections and are considered not bound to each other. Mice were treated intratumorally (20 μL), every other day, with 5 mg kg⁻¹ PVX or PVX-DOX or the corresponding dose of DOX (0.065 mg kg-1). Mice were sacrificed when tumors reached a volume >1000 mm³.

Immunostaining

When tumor reached volumes <100 mm³, mice were randomly assigned to the following groups (n=3): PBS or PVX-DOX. Mice were treated intratumorally (20 μL), every 7 days, with 5 mg kg-1 PVX-DOX. Mice were sacrificed when tumors reached a volume >1000 mm3 tumors were collected for analysis. Tumors were frozen in optimal cutting temperature compound (Fisher). Frozen tumors were cut into 12 μm sections. Sections were fixed in 95% (v/v) ethanol for 20 minutes on ice. Following fixation, tumor sections were permeabilized with 22 0.2% (v/v) Triton X-100 in PBS for 2 min at room temperature for visualization of intracellular markers. Then, tumor sections were blocked in 10% (v/v) GS/PBS for 60 min at room temperature. PVX and F4/80 were stained using rabbit anti-PVX antibody (1:250 in 1% (v/v) GS/PBS) and rat anti-mouse F4/80 (1:250 in 1% (v/v) GS/PBS) for 1-2 h at room temperature. Primary antibodies were detected using secondary antibody staining: AlexaFluor488-labeled goat-anti-rabbit antibody (1:500 in 1% (v/v) GS/PBS) and AlexaFluor555-labeled goat-anti-rat antibody (1:500 in 1% (v/v) GS/PBS) for 60 min at room temperature. Tumor sections were washed 3 times with PBS in between each step. Following the final wash, coverslips were mounted using Fluoroshield with DAPI. Slides were imaged on a Zeiss Axio Observer Z1 motorized FL inverted microscope. Fluorescence intensity was analyzed using ImageJ 1.47d (http://imagej.nih.gov/ij).

Luminex Assay

Intradermal melanomas were induced in C57BL/6J male mice (Jackson) as described above. Eight days post-tumor induction (day 0), mice were randomly assigned to the following groups (n=4): PBS, PVX, PVX-DOX, or PVX+DOX. Mice were treated intratumorally (20 μL) once and tumors where harvested at 24 h.p.i. Tumors were weighed and homogenized in T-PER™Buffer (ThermoFisher) at 1 mL of buffer/100 mg of tissue. TPER™Buffer was supplemented with cOmplete™ Protease Inhibitor Cocktail tablets (Roche) at one tablet per 8 mL of Buffer. After homogenization, homogenizer was rinsed with 0.5 mL HBSS (ThermoFisher) and added to the homogenate. Homogenate was centrifuged at 9,000×g for 10 minutes at 2-8° C. Supernatants were frozen and kept at −80° C. until analyses. Millipore Milliplex MAP mouse 32-plex was run at the CRWU Bioanalyte Core.

Results and Discussion

PVX is a filamentous plant virus, measuring 515×13 nm, and is comprised of 1270 identical coat proteins. While different in its physical nature compared to the 30 nm-sized icosahedrons formed by CPMV, PVX and PapMV share similar organization of the nucleoproteins arranged as flexuous soft matter filaments. To test whether PVX would stimulate an anti-tumor response when used as an in situ vaccine, we used the B16F10 melanoma model. B16F10 is a highly aggressive and poorly immunogenic tumor model used extensively for immunotherapy studies; it also has served as a model for the evaluation of the immunotherapeutic potential of virus-based therapies. Its low immunogenicity makes it an attractive platform to investigate new immunostimulatory therapies. B16F10 isografts were induced intradermally on the right flank of C57BL/6J mice. Eight days post-induction (tumor starting volume <100 mm³), mice were randomized (n=3) and treated weekly intratumorally with PBS or 100 μg of PVX or CPMV. Tumor volumes were measured daily and mice were sacrificed when tumors reached >1000 mm³. Treatment with CPMV or PVX alone significantly slowed tumor growth rate and extended survival time compared to PBS (FIG. 7), but there was no significant difference between CPMV and PVX treatment. These data indicate that PVX, like CPMV, can stimulate an anti-tumor response when used as an in situ vaccine.

Having established that PVX in situ vaccination slows tumor growth, we went ahead with a chemo-immuno combination therapy approach. We hypothesized that the combination of chemotherapy delivery, either co-administered (as physical mixture, PVX+DOX) or co-delivered (as complexed version, PVX–DOX), would enhance the anti-tumor effect. The underlying idea was that the chemotherapy would debulk the tumor to provide a burst of tumor antigens in the context of immunogenic cell death. This fosters specific immune recognition and response to those antigens; in turn, VLP-mediated immune-stimulation would further augment anti-tumor immunity and induce memory to protect from outgrowth of metastases and recurrence of the disease.

To obtain the PVX–DOX complex (FIG. 8A), purified PVX was loaded with DOX by incubating a 5,000 molar excess of DOX with PVX for 5 days; excess DOX was removed by ultracentrifugation. Incubation criteria were optimized: increasing molar excess of DOX resulted in extensive aggregation and further increasing incubation time did not increase loading capacity (data not shown). The PVX–DOX complex was characterized by agarose gel electrophoresis, UV/visible spectroscopy, and transmission electron microscopy (TEM) (FIGS. 8B-D). TEM imaging confirmed particle integrity following DOX loading. The PVX–DOX formulation stability was confirmed after 1 month of storage at 4° C.; DOX release was not apparent and the particles remained intact (data not shown). UV/visible spectroscopy was used to determine the number of DOX attached per PVX. The Beer-Lambert law, in conjunction with PVX- and DOX specific extinction coefficients, was used to determine the concentrations of both PVX and DOX in solution. The ratio of DOX to PVX concentration was then used to determine DOX loading. Each PVX was loaded with ~850 DOX per PVX. Agarose gel electrophoresis analysis indicated that DOX was indeed associated with PVX and not free in solution, as free DOX was not detectable in the PVX-DOX sample. The association of DOX with PVX may be explained based on hydrophobic interactions and π-π stacking of the planar drug molecules and polar amino acids.

Efficacy of the PVX–DOX complex was confirmed using B16F10 melanoma cells (FIG. 8E). DOX conjugated to PVX maintained cell killing ability, although with decreased efficacy resulting in an $IC_{50}$ value of 0.84 μM versus 0.28 μM for free DOX. Similar trends have been reported with synthetic and virus-based nanoparticles for DOX delivery. The reduced efficacy may be explained by reduced cell uptake and required endolysosomal processing when DOX is delivered by nanoparticles.

To test the hypothesis that a combination chemo-immunotherapy would potentiate the efficacy of PVX alone, DOX-loaded PVX (PVX–DOX) and PVX+DOX combinations were tested in the B16F10 murine melanoma model. The combination of PVX+DOX served to test whether merely the combination of the therapies or the co-delivery (PVX–DOX) would enhance the overall efficacy. PVX+DOX was combined less than 30 min before injection to ensure that the two therapies did not have time to interact. PBS, PVX alone, and free DOX were used as controls. When tumors were <100 mm3, mice were treated every other day intratumorally with PVX–DOX, PVX+DOX, or corresponding controls (n=6). Tumor volumes were measured daily and mice were sacrificed when tumors reached >1000 mm$^3$. PVX was administered at 5 mg kg$^{-1}$ (corresponding to a dose of 0.065 mg kg-1 DOX). Clinically, doxorubicin is administered at doses of 1-10 mg kg$^{-1}$, intravenously. If 1-10% of the injected dose reaches the tumor site, the resulting intratumoral dose would equate to 0.01-1 mg kg$^{-1}$; thus our intratumoral dose is within a clinically relevant range of DOX.

Figure 9A:
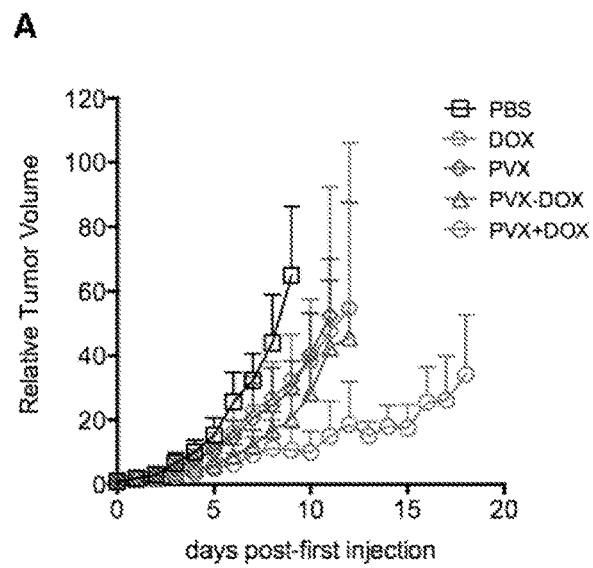
FIGS. 9A-C illustrate chemo-immunotherapy treatment of B16F10 tumors. Groups (n=6) were treated with PBS, PVX, DOX, PVX-DOX, or PVX+DOX. PVX was administered at a dose of 5 mg kg$^{-1}$, DOX was administered at a dose of 0.065 mg kg$^{-1}$. Injections were repeated every other day until tumors reached >1000 mm3. A) Tumor growth curves shown as relative tumor volume. Statistical significance was detected comparing PVX vs. PVX+DOX. B) Survival rates of treated mice. C) Immunofluorescence imaging of three representative PVX-DOX tumor sections after weekly dosing of PVX-DOX (animals received 2 doses of PVX and were collected when tumors reached >1000 mm$^3$. Tumors treated with PVX-DOX (rows 1-3) were sectioned and stained with DAPI (blue), F4/80 (red), and PVX (green). Scale bar=100 μm.
Figure 9B:
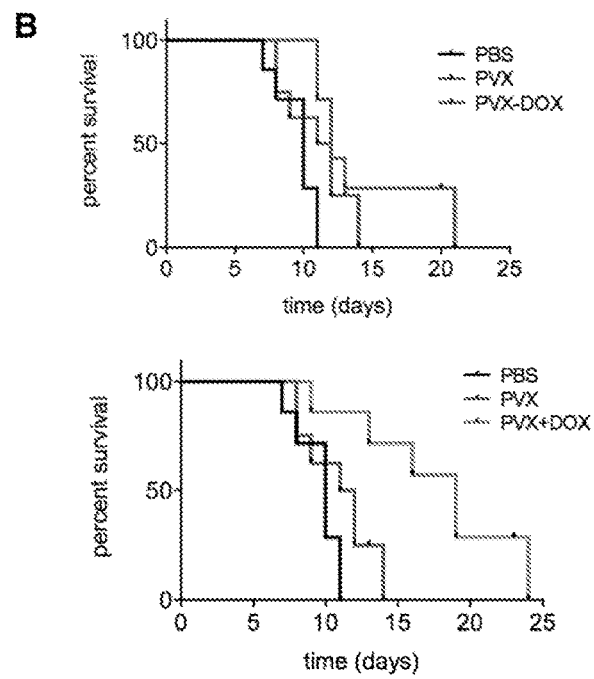

While there was no statistical difference in tumor growth rate or survival time between PVX–DOX complex versus PVX or DOX alone, PVX+DOX did significantly slow tumor growth rate versus PVX and DOX alone (FIGS. 9A+B). Thus, the data indicate that the combination of DOX chemotherapy and PVX immunotherapy indeed potentiates efficacy, however the formulation as a combined nanoparticle, PVX–DOX, did not improve the treatment. The lack of statistically significant enhancement of efficacy of the PVX–DOX complex versus immuno- or chemo-monotherapy may be explained by the fact that the therapies synergize best when they act on their own. DOX targets replicating cancer cells to induce cell death, and PVX likely associated with immune cells to stimulate an anti-tumor effect—most likely through activation of signaling cascades through pathogen-associated molecular pattern (PAMP) receptors and other danger signals. Indeed, we found that PVX was co-localized with F4/80+ macrophages within the tumor tissue (FIG. 9C), which may cause killing of immune cells rather than cancer cells; even if the nanoparticles do not exhibit cytotoxic effect on the immune cell population, the sequestration of PVX–DOX in the immune cells would lower the anti-tumor efficacy of the complex.

To gain insight into the underlying immunology we performed cytokine/chemokine profiling using a 32-plex MILLIPLEX® Luminex® assay. Tumors were treated with PBS, PVX, DOX, PVX–DOX, or PVX+DOX and harvested 24 hours after the first injection. Profiles were obtained using tumor homogenates and normalized to total protein levels by the bicinchoninic acid (BCA) assay. The PVX+DOX group repeatedly showed significantly higher particular cytokine and chemokine levels compared to any other group. Specifically, interferon gamma (IFNγ) and IFNγ-stimulated or synergistic cytokines were elevated. These included, but may not be limited to: Regulated on Activation, Normal T Cell Expressed and Secreted (RANTES/CCL5), Macrophage Inflammatory Protein 1a (MIP-1a/CCL3), Monocyte Chemoattractant Protein (MCP-1/CCL2), Monokine Induced by Gamma interferon (MIG/CXCL9), and IFNγ-induced protein 10 (IP-10). IFNγ is a multifunctional type II interferon critical for inducing a pro-inflammatory environment and antiviral responses and is often associated with effective tumor immunotherapy responses. Under the influence of IFNγ, these chemokines mediate the influx of monocytes, macrophages, and other immune cells. Interestingly, the induction of IFNγ was not associated with the increased expression of its master positive regulator, IL-12, thus in this context, the increased expression of IFNγ is IL-12-independent (data not shown). In the tumor microenvironment, activation of the IFNγ pathway is in accordance with other work, where viruses were applied as an in situ vaccine. Stimulation of the IFNγ pathway alleviates the immuno-suppressive tumor microenvironment promoting an anti-tumor immune response. The molecular receptors and signaling cascades are yet to be elucidated, but the body of data indicates IFNγ to be a key player for viral-based in situ vaccination approaches.

Other noteworthy cytokines/chemokines that were up-regulated include interleukin-1β (IL-1β) and Macrophage Colony-Stimulating Factor (M-CSF). IL-1β is known to be an early pro-inflammatory cytokine activated by many PAMPs and Danger Associated Molecular Patterns (DAMPs). IL-1β signaling was also observed in our earlier work with CPMV, and data suggest that initial recognition of the viral in situ vaccine by innate surveillance cells is promoting immune activation. IL-1β and M-CSF are both major recruiters and activators of monocytes and macrophages to the site of challenge. M-CSF, in particular, enhances monocyte functions including phagocytic activity and cytotoxicity for tumor cells, while inducing synthesis of inflammatory cytokines such as IL-1, TNFα, and IFNγ in monocytes. PVX monotherapy appears to follow a similar trend of increased expression of cytokines/chemokines, with further enhanced response through combination with DOX when coadministered (PVX+DOX), but reduced response when directly coupled together as PVX–DOX.

In this example, we demonstrate that PVX stimulates an anti-tumor immune response when used as an in situ vaccine. Data indicate that the plant virus-based nanoparticles activate the innate immune system locally—this innate immune activation is thought to overcome the immunesuppressive tumor microenvironment re-starting the cancer immunity cycle leading to systemic elimination of cancer cells through the adaptive immune system. It is likely that innate receptors such as pattern recognition receptors (PRR) play a key role recognizing the multivalent nature of the plant virus nanoparticles; the repetitive, multidentate coat protein assemblies are products known as pathogen-associated molecular patterns (PAMPs).

The combination of the DOX chemotherapeutic with PVX was more efficacious than the monotherapies when co-administered as the PVX+DOX formulation, but not when physically linked in the PVX-DOX formulation. Data show that PVX+DOX induced a higher immune mediator profile within the tumor microenvironment, in turn resulting in increased efficacy against B16F10 melanoma. A key conclusion to draw from these studies is that the combination of chemo- and immunotherapy indeed is a powerful tool—yet the formulation of the two regimes into a single, multi-functional nanoparticle may not always be the optimal approach.

Figure 9C:
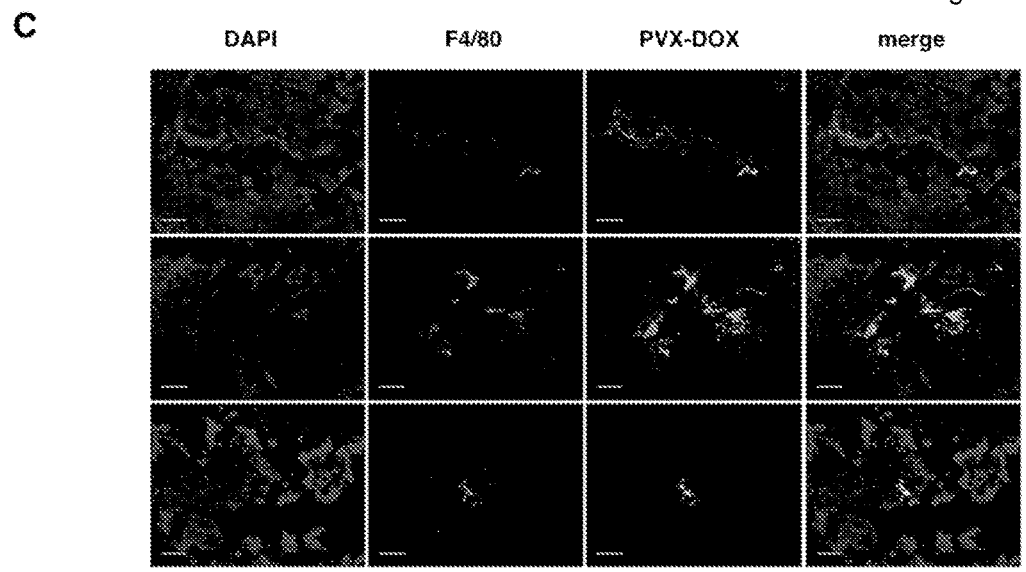

It has long been recognized that nanoparticles are preferentially ingested by phagocytic cells. FIG. 9C confirms this and shows that PVX-DOX is concentrated in F4/80+ macrophages within the tumor. The basis for reduced efficacy of PVX-DOX as compared to PVX+DOX could simply be because when phagocytes ingest PVX-DOX, it reduces the concentration of DOX available to react with tumor cell DNA. If as seems likely, the cells that respond to PVX at least initially are phagocytes, then a nonexclusive alternative could be that ingestion of PVX-DOX by phagocytes leads to a different response than ingest of PVX by itself by those cells, thus blunting the immune response stimulated by PVX.

Chemo- and immunotherapy regimes have been recognized to synergize and several reports have highlighted the potential of combinatorial nanoparticles to deliver chemotherapies while stimulating the immune system. While the nanomedicine field strives to design multifunctional nanoparticles that integrate several functions and therapeutic regimens into single nanoparticle—our data indicate minimal improvement in efficacy using the combinatorial PVX-DOX nanoparticles. Significant therapeutic efficacy with prolonged survival is only achieved when the therapeutic regimes, PVX immunotherapy and DOX chemotherapy, are co-administered separately allowing each drug to act on their own, leading to potent anti-tumor effects.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Example 4

The tumor microenvironment (TME) has been identified as one of the locations where the cancer-immunity cycle is deregulated by functioning as an immune rheostat or "immunostat". The TME can be highly immunosuppressive, due to a variety of factors including the impairment of antigen presenting machinery, increase of immunosuppressive factors, inhibition of dendritic cell maturation, and up regulation of regulatory T cells. Interestingly, instead of avoiding interactions with the immune system, tumors actively recruit immunosuppressive immune cells through cytokine signaling. In addition, once infiltrated in the TME, signaling further modulates immune responses by switching cells from an antitumor phenotype to a tumor enabling phenotype. Not only are these protumor cells tolerant to tumors, they also support tumor development by secreting cytokines and growth factors. A promising avenue in cancer therapy, is the re-programming of the TME to restore the cancer-immunity cycle and thus the body's own defense against tumors.

Cancer immunotherapy approaches generally target one of two mechanisms: blocking immunosuppressive targets (i.e. IL-10, CD73, TIM-3), or activating immune targets (i.e. CD137 and tumor vaccines). Over the past three decades, several immunotherapies like immunostimulatory cytokines and recently checkpoint inhibitors (CTLA4 and PD-1/PDL-1) have been developed. However, the systemic administration of exogenous immune modulators only target specific steps of the cancer immunity cycle, are not delivered at physiological ranges, or lack tumor specificity leading to serious immune side effects and suboptimal responses. To avoid the toxicities, alternative and safer localized strategies are required. The concept of in situ vaccination has emerged. An in situ vaccine, generally an immunostimulatory adjuvant, is administered directly into an identified tumor or metastatic site to reprogram the TME from an immunosuppressive to immunostimulated phenotype, thus restarting the cancer immunity cycle, and if successful mobilizing a systemic anti-tumor immune response. For example, Imlygic® (tamilogene laherparepvec or T-VEC) has shown success as in situ vaccine in the setting of melanoma. T-VEC is a genetically modified oncolytic herpes virus, engineered to express the cytokine granulocyte-macrophage colony-stimulating factor (GM-CSF). While TVEC has shown efficacy in the context of melanoma, concerns surround the safety aspects of using a human pathogen as a therapeutic. Possible safer alternatives are biologics derived from non-human pathogens, such as plant viral-based approaches.

Toward this end, we have recently demonstrated, that plant viral and viral-like particles from cowpea mosaic virus (CPMV), papaya mosaic virus (PapMV) and potato virus X (PVX) can induce immune-mediated anti-tumor responses when introduced into the TME as an in situ vaccine. It is hypothesized that the plant virus-based nanoparticles activate the innate immune system locally. This innate immune activation is thought to overcome the immunosuppressive TME, restarting the cancer immunity cycle, leading to systemic elimination of cancer cells through the adaptive immune system. While the anti-tumor immunestimulation of PapMV was attributed to its packaged RNA and associated stimulation of toll-like receptors (TLRs), our previous studies with RNA-free "empty" CPMV (termed eCPMV) indicated that the RNA cargo is not required (at least in the case of the CPMV platform). Thus it is likely that innate receptors such as pattern recognition receptors (PRRs) play a key role recognizing the multivalent nature of the plant virus or plant viral-like nanoparticles. The repetitive, multivalent coat protein assemblies are products known as pathogen-associated molecular patterns (PAMPs).

The potency of the plant viral in situ vaccination strategy is intriguing and questions remain regarding the underlying immunology as well as the engineering design space, i.e., whether the anti-tumor effect is a property of any (plant) virus-based nanomaterial or whether shape, size, and molecular composition of the virus relate to its efficacy. Therefore, the present work set out to investigate the following; (1) we asked whether tobacco mosaic virus (TMV) could be used as an in situ vaccine to elicit an anti-tumor immune response against melanoma; and if so (2) whether the potency of this response would be influenced by structural parameters. To test this, we compared assembled TMV vs. free coat proteins (CPs), full-length 300×18 nm TMV vs. shorter TMV variants measuring ~50×18 nm (TMVshort) vs. spherical TMV nanoparticles (termed SNPs). (3) We addressed whether the TMV-mediated anti-tumor responses against melanoma would match the efficacy observed with CPMV nanoparticles. While filamentous plant viruses, such as PVX and PapMV were utilized in previous work, TMV provides an interesting alternative because of its robust and well-developed surface chemistry its shape engineering capabilities; the synthesis of complex shapes such as star-shaped TMV and boomerang-shaped TMV has been described in the literature. This level of engineer-ability has not yet been demonstrated with the filamentous plant virus platforms. Another key difference between the filamentous platforms PVX and PapMV vs. TMV is the flexible modulus of the particles: while PVX and PapMV are flexible filaments, TMV is a rigid nanotube. For these reasons, we felt that TMV would be a welcome addition to test as an in situ vaccine.

FIG. 10 depicts the library of viral nanoparticles under consideration. Using a mouse model of dermal melanoma, we compared anti-tumor efficacy of these plant viral nanoparticles side-by-side; temporal changes in cytokine and immune cell profiles were assessed using Luminex assays, histology, and flow cytometry to gain insights into whether differences in efficacy could be explained merely by differences in magnitude of immune activation or underlying differences in the mechanism of immune activation.

Materials and Methods

VLP Production

TMV was propagated in *Nicotiana benthamiana* plants and purified as previously reported. CPMV was propagated in *Vigna unguiculata* plants and purified as previously reported.

TMV disassembly methods to yield purified CPs were as previously described. In brief, particles were exposed to cold glacial acetic acid in a 1:2 ratio (v/v), vortexed, and allowed to sit on ice for 20 minutes. Afterwards tubes were centrifuged for 20 minutes at 20,000 g and 4° C. The supernatant was transferred and diluted in a 1:1 ratio (v/v) with MilliQ water. The CP were dialyzed against MilliQ water for at least 48 hours at 4° C., with daily changing of the water. At the end of the dialysis, CP were centrifuged for 20 minutes at 20,000 g and 4° C. CP were then resuspended in 200 μL sodium phosphate buffer 75 mM pH 7.2 and resuspended overnight. The next day, CPs were centrifuged for 20 minutes at 10,000 g at room temperature.

To produce TMVshort, an RNA-templated self-assembly protocol was used. In brief, DNA plasmid pIDTblue-TMVshort containing the first 1177 nt of the TMV genome (6.5 kb) including the origin-of-assembly site (OAS), a T7 promotor, and an ampicillin gene were amplified in *E. coli* and purified by Qiagen® Maxi-Prep. Plasmid pIDTblue-TMVshort was linearized using BamH1 and NgoMIV restriction enzymes (NEB). Following linearization, DNA fragments were purified and transcribed using a T7-based MegaScript® kit (Thermo Fisher Scientific) and the resulting RNA was purified with the MEGAclear® kit (Thermo Fisher Scientific). To yield TMVshort (measuring 54 nm as defined by the length of the in vitro transcribed RNA template), obtained synthetic RNA transcripts were incubated with purified TMV coat proteins (CPs) at 37° C. in 75 mM sodium phosphate buffer pH 7.2 overnight.

Spherical TMV nanoparticles (SNPs) were produced through thermal shape-transition as previously reported.

Agarose Gel Electrophoresis

To confirm plasmid sizes, restriction digest cuts, and T7 reverse transcription, nucleic acids were loaded with 6× agarose loading dye (Invitrogen) and analyzed in a 0.8% (w/v) agarose gel (in 1×TBE) stained with GelRed® nucleic acid stain (BioRad). DNA/RNA samples were separated at 100 V for 30 min. Gels were then visualized under UV light using an Alpha Imager (Alpha Innotech).

UV/Visible Spectroscopy

The concentration as well as the purity of CPMV, TMV particles, and CPs was determined by UV/visible spectroscopy, using the NanoDrop™2000 spectrophotometer (Thermo Fisher Scientific). Protein concentration was determined using the Beer-Lambert law and the protein/assembly-specific extinction coefficients (ε); TMV ε=3.1 mL mg$^{-1}$ cm$^{-1}$ at 260 nm), TMV CP ε=1.2 mL mg$^{-1}$ cm$^{-1}$ at 260 nm, and CPMV ε=8.1 mL mg$^{-1}$ cm$^{-1}$ at 260 nm. The RNA: protein (260/280) ratios were used to measure the purity of the CPMV (A260/280=1.8), TMV and TMVshort (A260/280=1.2), and TMV CPs (A260/280=0.65).

Transmission Electron Microscopy (TEM), Scanning Transmission Electron Microscopy (STEM), and Scanning Electron Microscopy (SEM)

TEM and STEM imaging was performed after CPMV and TMV particle purification to confirm their integrity. CPMV and TMV samples (0.1 mg mL$^{-1}$, in dH$_2$O) were placed on carbon-coated copper grids and negatively stained with 0.2% (w/v) uranyl acetate. For TEM imaging, grids were imaged using a Zeiss Libra® 200FE Transmission Electron Microscope, operated at 200 kV. For STEM imaging, samples were prepared as described above and imaged using a FEI Helios NanoLab™ 650 Field Emission Scanning Electron Microscope with Focused Ion Beam with XEDS, operated at 30 kV 0.4 nA at 50-100 k magnification. For SEM imaging of SNPs, samples were prepared on silica wafers and sputter coated with gold prior to imaging using a FEI Helios NanoLab™ 650 Field Emission Scanning Electron Microscope with Focused Ion Beam with XEDS, operated at 1 kV at 10 k magnification.

Fast Protein Liquid Chromatography (FPLC)

To further confirm purity and structural integrity of TMV particles and CPs, FPLC was performed using an ÄTKA-purifier and Superose 6 column and methods as previously reported.

Cell Culture

B16F10 cells (ATCC) were cultured in Dulbecco's modified Eagle's media (DMEM, Life Technologies), supplemented with 10% (v/v) fetal bovine serum (FBS, Atlanta Biologicals) and 1% (v/v) penicillin-streptomycin (Life Technologies). Bone marrow derived dendritic cells (BMDCs) were harvested from the femurs and tibias of euthanized C57BL/6 mice. The bones were rinsed in 70% ethanol, epiphyses removed and the marrow flushed. Cells were broken up to a single cell suspension and applied to a 40-μm cell strainer. Red blood cells were depleted with Ammonium Chloride Potassium (ACK) lysing buffer, followed by washing with Phosphate Buffer Saline (PBS). The marrow cells were filtered, washed, and resuspended at 1×10$^6$ cells/ml in T cell media Roswell Park Memorial Institute RPMI (Corning) supplemented with 10% (v/v) Fetal Bovine Serum (FBS), 1% (v/v) penicillin/streptomycin (Pen/Strep), 1% (v/v) MEM non-essential amino acids (Corning), 1 mM sodium pyruvate and 50 mM beta-mercaptoethanol (Life Technologies) supplemented with 10 ng/ml mouse interleukin 4 (IL-4) (BioLegend) and 15 ng/mL mouse GM-CSF (BioLegend). 3 mL of cells were plated/well of a 6-well plate and incubated at 37° C. The media was removed and replaced with fresh T cell media supplemented with IL-4 and GM-CSF on day 3 and an additional 3 mL of fresh T cell media supplemented with IL-4 and GM-CSF was added on day 5. Cells were harvested on day 7.

Animal Studies

All experiments were conducted in accordance with Case Western Reserve University's Institutional Animal Care and Use Committee. C57BL/6J male mice (Jackson Laboratory) were used. B16F10 tumors were induced intradermally into the right flank of C57BL/6J mice ($1.25 \times 10^5$ cells/50 μL DMEM media). Animals were monitored and tumor volumes were calculated as $V=0.5 (a \times b^2)$; where a is length and b is width of the tumor.

Treatment Schedule

Eight days post-tumor induction (day 0), mice were randomly assigned to the following groups (n=8): PBS, TMV, TMVshort, TMV CP, or CPMV. Mice were treated intratumorally (20 μL), every 4 days, with 100 μg of the respective CPMV/TMV particle, CP, or PBS. Mice were sacrificed when tumors reached a volume >1500 mm³ or when tumors exceed 10% body weight.

Luminex Assay

Intradermal B16F10 melanoma tumors were induced in C57BL/6J male mice (Jackson) as described above. Eight days post-tumor induction (day 0), mice were randomly assigned to the following groups (n=4): PBS, TMV, TMVshort, TMV-CP, or CPMV. Two treatment schedules were analyzed: 1) Mice were treated intratumorally (20 μL) once with 100 μg of the respective CPMV/TMV particle, CP, or PBS, and tumors were harvested at 24 hours post treatment. 2) Mice were treated intratumorally (20 μL) on day 0 and day 4 with 100 μg of the respective CPMV/TMV particle, CP, or PBS, and tumors were harvested at 4 hours after the second injection (day 4). Millipore Milliplex MAP mouse 32-plex was run by Eve Technologies Corporation (Calgary, Canada).

In vitro Luminex assays were done with BMDCs. Cells were isolated as previously described and treated with PBS (negative control), TMV, TMVshort, TMV CP, CPMV, or lipopolysaccharides (LPS) (positive control). LPS is a known agonist of TLR4. Media was collected 24 hours post treatment. Millipore Milliplex MAP mouse 32-plex was run by Eve Technologies Corporation.

Cytokine and Chemokine Pathway Analysis

Cytokine and chemokines that were significant between treatment groups in the Luminex assay were imported into Crosstalker software (https://sb4j.case.edu) for pathway analysis. The cytokine/chemokines added function as seeds; crosstalker software then develops networks based on published interactions. Seeds were mapped by corresponding gene symbols to human genes using the BioGRID database. Result networks were tested for functional enrichments by hypergeometric test, to assess over-representation of gene sets from the selected pathway database. A more comprehensive description can be found.

Flow Cytometry

Intradermal B16F10 melanomas were induced in C57BL/6J male mice (Jackson) as described above. Eight days post-tumor induction (day 0), mice were randomly assigned to the following groups (n=4): PBS, TMV, or CPMV. Mice were treated intratumorally as described above. Tumors were harvested at 4 and 10 days post initial treatment. Tumors were prepared for flow cytometry as previously described. Briefly, single tumor cell suspensions were incubated in anti-CD16/CD32 antibody (BioLegend) for Fc receptors blocking for 15 min in the dark. Cell viability was assessed using Zombie Yellow™ Fixable Viability Kit (BioLegend) for 30 min incubation in the dark on ice followed by a single wash in 1×PBS. Surface staining was performed in the dark for 30 min at 4° C. in FACS staining buffer (1 mM EDTA, 1% (v/v) FBS, and 25 mM HEPES, pH 7.0 in $Ca^{2+}$ and $Mg^{2+}$ free PBS). Cells were then washed twice with staining buffer followed by fixation in 3% (v/v) paraformaldehyde. Fluorophore-labeled monoclonal antibodies used for surface staining of cell type-specific markers including CD45, CD11b, CD11c, NK1.1, Ly6C, Ly6G, CD3, CD8, CD4, CD62L, and CD44 (BioLegend). Tumors harvested at day 4 were subjected to the innate cell antibody panel and the day 10 tumors were tested for the adaptive panel (Table 1). Flow cytometry analyses were performed on a BD LSR II flow cytometer (BD Biosciences) and data was analyzed using the FlowJo software (Tree Star Inc.).

TABLE 1

Antibodies used for flow cytometry.

| Dye | Marker | Vendor | Catalog No. | Clone/Host | Isotype | Concentration |
|---|---|---|---|---|---|---|
| Innate panel | | | | | | |
| Pacific blue | CD45 | BioLegend | 103126 | 30-F11 Rat | IgG2b, K | 0.5 mg/ml |
| FITC | CD11b | BioLegend | 101205 | M1/70 Rat | IgG2b, K | 0.5 mg/ml |
| PE | CD80 | BioLegend | 104707 | 16-10A1 A. Hamster | IgG | 0.2 mg/ml |
| PE-Cy7 | CD86 | BioLegend | 105014 | GL-1 Rat | IgG2a, K | 0.2 mg/ml |
| APC | I-A/I-E (=MHCII) | BioLegend | 107613 | M5/114.15.2 Rat | IgG2b, K | 0.2 mg/ml |
| APC/Cy7 | Ly-6G | BioLegend | 127623 | 1A8 Rat | IgG2a, K | 0.2 mg/ml |
| APC | CD11c | BioLegend | 101205 | N418 A. Hamster | | 0.2 mg/ml |
| PE | F4/80 | BioLegend | 123109 | BM8 Rat | IgG2a, K | 0.2 mg/ml |
| PE/Cy7 | Ly6C | BioLegend | 128018 | HK1.4 Rat | IgG2c, K | 0.2 mg/ml |
| BV605 | NK1.1 | BioLegend | 108737 | PK136 | IgG2a, κ | 0.2 mg/ml |
| Adaptive panel | | | | | | |
| Pacific blue | CD45 | BioLegend | 103126 | 30-F11 Rat | IgG2b, K | 0.5 mg/ml |
| FITC | CD4 | BioLegend | 100405 | GK1.5 Rat | IgG2b, K | 0.5 mg/ml |
| PE | CD44 | BioLegend | 103007 | IM7 Rat | IgG2b, K | 0.2 mg/ml |
| PE-Cy7 | CD62L (L-selectin) | BioLegend | 104417 | MEL-14 Rat | IgG2a, K | 0.2 mg/ml |

TABLE 1-continued

Antibodies used for flow cytometry.

| Dye | Marker | Vendor | Catalog No. | Clone/ Host | Isotype | Concentration |
|---|---|---|---|---|---|---|
| APC | CD8α | BioLegend | 100712 | 53-6.7 Rat | IgG2a, K | 0.2 mg/ml |
| APC/Cy7 | CD3ε | BioLegend | 100330 | 145-2C11 A. Hamster | IgG | 0.2 mg/ml |

Histology, Immunostaining, and Immunohistochemistry (IHC)

Intradermal B16F10 melanomas were induced in C57BL/6J male mice (Jackson) as described above. Eight days post-tumor induction (day 0), mice were randomly assigned to the following groups (n=4): PBS, TMV, or CPMV. Mice were treated intratumorally as described above and tumors where harvested at 4 days, 6 days, or 10 days post initial treatment. Tumors were then fixed in 4% (v/v) paraformaldehyde in PBS for 5-7 days then transferred to 1% (v/v) paraformaldehyde in PBS and taken to the Case Western Reserve University Pathology core for sectioning and staining. Tumors for frozen IHC were flash frozen and also delivered to the Pathology core for processing.

Paraformaldehyde tumors were treated serially in 10% (v/v) neutral buffered formalin (twice), 70% (v/v) ethanol, and 80% (v/v) ethanol for 90 minutes at 45° C. each. Subsequently, tumors were serially treated for two hours at 45° C. in 95% (v/v) ethanol, and 100% ethanol (three times). Next tumors were placed in xylene for 90 minutes at 45° C. (this step was carried out twice, i.e., slides were moved to a solution of fresh xylene after the first 90-min incubation step). Finally tumors were kept in paraffin for two hours at 45° C. (this step was carried out three times). Then samples were kept at 60° C. until embedding in paraffin. Paraffin blocks were soaked in cold dH$_2$O followed by sectioning of 5 µM-thin tissue sections using a microtome. Then the sections were placed in 45° C. dH$_2$O, then placed on a charged slide, and allowed to dry overnight at room temperature.

For H&E staining, slides from paraffin embedded tissues were baked at 60° C. for 90 minutes and then deparaffinized in xylene for two minutes. Slides were then rehydrated through a series of graded ethanol washes for two minutes each: 100% (v/v), 95% (v/v), and 70% (v/v) followed by a rinse in dH$_2$O. Slides were stained by placing them for 15 minutes in Harris Modified Hematoxylin (Fisher Scientific) followed by rinsing in water five times (10 dips each). Slides were differentiated with eight dips in 1% (v/v) acid alcohol (hydrochloric acid in 70% (v/v) ethanol) followed by five dips in saturated lithium chloride (1% (v/v) in dH$_2$O); then slides were washed by rinsing in tap water (10 dips five times). Slides were placed in 70% (v/v) ethanol and then 95% (v/v) ethanol for two minutes each prior to counterstaining with Esosin Y (Fisher Scientific) for three minutes. Slides were subsequently dehydrated in 100% ethanol for two minutes (five times) and cleared in Xylene for two minutes (twice). Slides were mounted with resinous mounting medium (Mercedes Medical, OpticMount) and allowed to dry overnight.

For IHC slides from paraffin embedded tissues were baked at 60° C. for 75 min and then deparaffinized in xylene twice for seven minutes. Slides were then rehydrated through a series of graded ethanols: 100% (twice for two minutes each), 95% (twice for two minutes each), and 70% for two minutes followed by a rinse in dH$_2$O. Antigen retrieval was achieved using 0.01 M citrate buffer pH 6.0 (Vector Labs, H3300) and by placing slides in a pressure cooker for 30 seconds at 123° C. followed by cooling at room temperature for 20 min, and followed by a rinse in dH$_2$O for two minutes. The endogenous peroxidase activity was then blocked in Peroxidazed (PX968M, BioCare Medical) for 8 minutes, followed by rinsing in dH$_2$O. Following peroxidase block, endogenous mouse IgG was blocked using Rodent Block (RBM961, BioCare Medical) for 20 minutes, followed by a rinse using Tris-buffered saline (TBS) with Tween-20 (TBST). The slides were then immunostained with the corresponding primary antibodies (Table 2) or with without antibodies for the negative controls (Protein Block Serum-Free [Antibody Diluent], X0909, DAKO Cytomation) for 1 hour at room temperature, followed by TBST rinse. Slides were then treated with Rabbit-on-Rodent HRP Polymer (RMR622H, BioCare Medical) for 30 minutes and rinsed with TBST. The slides were incubated with the Betazoid DABKit (BDB2004L, Betazoid DAB Chromogen, BioCare Medical) mix for 5 min in the dark followed by rinsing with dH$_2$O. This was followed by counterstaining with CAT Hematoxylin (CATHE-M, BioCare Medical).

After processing, all slides were scanned digitally using the Leica SCN400 Slide Scanner (Leica Biosystems, Wetzlar, Germany) for digital image storage and analysis.

TABLE 2

Antibodies used for immunohistochemistry

| Marker | Vendor | Catalog No. | Clone/Host |
|---|---|---|---|
| CD45 | Abcam | ab10558 | Rabbit |
| CD3 | Abcam | ab16669 | Rabbit |

Results
CPMV and TMV Library Production

In this example we set out to address i) whether TMV would be effective as in situ vaccine against melanoma, and whether the shape (TMV rod vs. SNP), aspect ratio (AR17 for native TMV measuring 300×18 nm and AR3 for TMVshort measuring 54×18 nm), or state of assembly (multivalent TMV particle vs. soluble CP) of TMV would impact its efficacy as in situ vaccine. The icosahedron CPMV, measuring 30 nm in diameter, was used as a standard, because we previously reported its potent efficacy when used as in situ vaccine against melanoma amongst other metastatic tumors.

The viral nanoparticle library was obtained using a combination of molecular farming and self-assembly methods (FIG. 11). CPMV, a 30 nm-sized icosahedron with P3 symmetry consisting of 60 copies each of a small (S) and large (L) coat protein, was produced and isolated from *Vigna unguiculata* (black-eyes peas or cowpea plants No. 5, FIG. 11A). The following TMV configurations were obtained: native TMV measuring 300×18 nm was produced in and isolated from *Nicotiana benthamiana* (Australian tobacco, FIG. 11B). To obtain TMV CP and TMVshort, established dis- and re-assembly methods were employed. CP was obtained through disassembly of native TMV; and purified CP was assembled on synthetic TMV transcripts containing an origin of assembly site (OAS) to initiate the self-assembly reaction; TMV transcripts containing 1177 nt of the 6.5 kb TMV genome (FIG. 11) were used as template yielding TMVshort particles measuring 54 nm in length; the width is constant at 18 nm (FIG. 11C+D). Lastly, SNP measuring ~250 nm in diameter were obtained through previously described heat-transformation of TMV-to-SNP (FIG. 11E).

The CPMV and TMV particles and CPs thereof were characterized by UV/visible spectroscopy, FPLC, and S/TEM to confirm concentration, purity, and structural integrity prior to use in animal studies (FIG. 12).

Figure 12A:
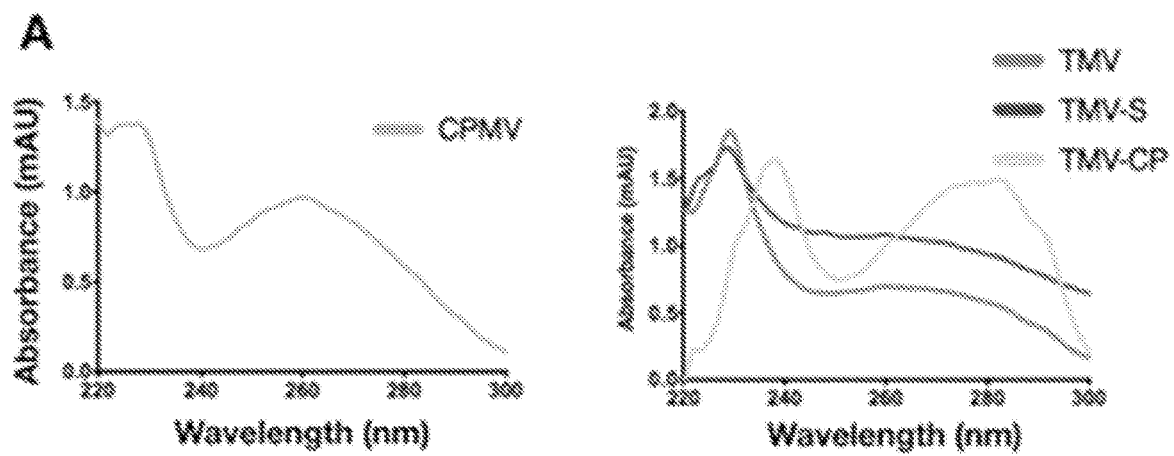
FIGS. 12A-C illustrate characterization of viral nanoparticle libraries. (A) UV/visible spectroscopy of CPMV, TMV, TMVshort (TMV-S), and TMV-CP. (B) Fast Protein Liquid Chromatography (FPLC) of CPMV, TMV, TMVshort (TMV-S), and TMV-CP. (C) TEM of CPMV and TMV and STEM of TMVshort; all samples were negatively stained with 0.2% (w/v) uranyl acetate.
Figure 12B:
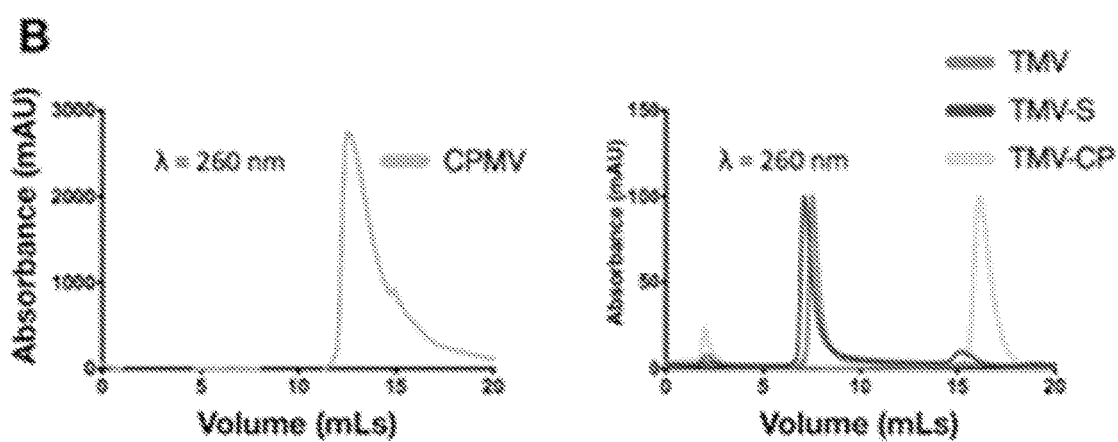
Figure 12C:
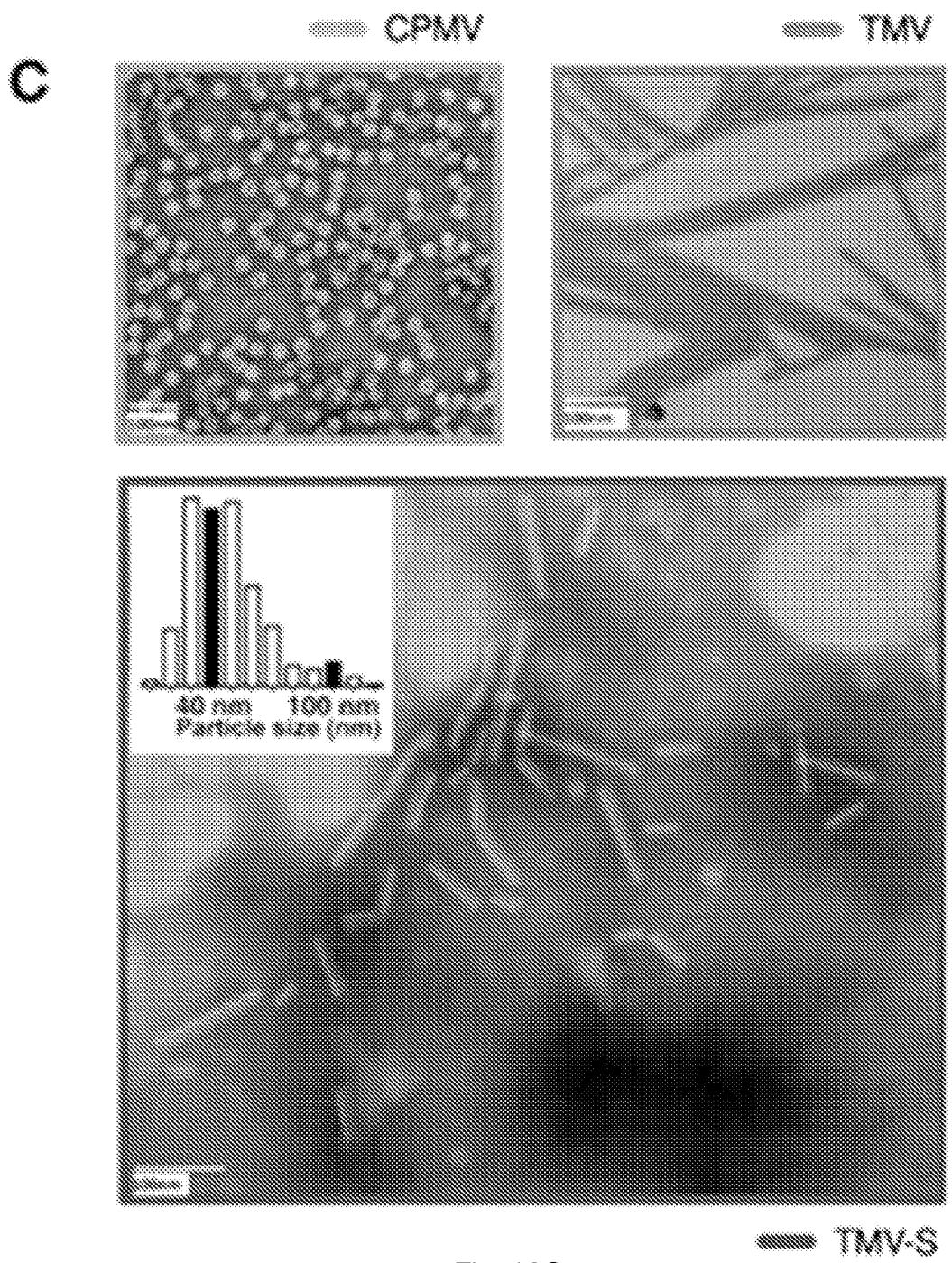

The concentration as well as the purity of CPMV and TMV particles and CPs was determined by UV/visible spectroscopy. The RNA:protein (260/280) ratios indicated that pure and intact CPMV (A260/280=1.8), TMV and TMVshort (A260/280=1.2), and TMV CPs (A260/280=0.65) were produced (FIG. 12A). FPLC using ATKA-purifier and Superose6 column showed the typical elution profiles for intact CPMV at 12-15 mL, for intact TMV and TMVshort at ~8 mL (due to the high molecular weights of either assembly, $5.6 \times 10^6$ kDa and $40 \times 10^6$ kDa for TMVshort and TMV, respectively, differences in elution profiles are not apparent due to the limitations of the pore size resolution of the Superose6 column), and for soluble CPs at 16-17 mL (FIG. 12B). TEM and STEM analysis of negatively-stained samples further confirmed structural integrity and the expected sizes of the viral nanoparticles (FIG. 12C) with CPMV nanoparticles appearing spherical in shape with a diameter of 30 nm and native TMV forms high aspect ratio soft-matter nanorods measuring 300×18 nm. 240 TMVshort particles were analyzed and their length measured (FIG. 12C); the mean length was determined at 50 nm±20 nm (with the 57 nm in the 75%), the minimum length was 13 nm (likely incomplete assemblies) and the longest length was measured at 155 nm (either non-RNA templated assemblies or end-to-end assemblies of multiple TMVshort or fragments thereof). SNPs were also characterized by STEM and the averaged diameter was determined at ~250 nm.

In Vivo Efficacy of TMV Vs. CPMV In Situ Vaccines Against Dermal Melanoma

To test whether TMV, TMVshort, its CP, or SNPs would stimulate an anti-tumor response when used as an in situ vaccine, we used the B16F10 melanoma model. B16F10 is a highly aggressive and poorly immunogenic tumor model used extensively for immunotherapy studies; it also has served as a model for the evaluation of the immunotherapeutic potential of virus-based therapies; for example we and others have previously shown efficacy of icosahedral CPMV as well as filamentous PapMV and PVX. Its low immunogenicity makes it an attractive platform to investigate new immunostimulatory therapies. B16F10 isografts were induced intradermally on the right flank of C57BL/6J mice. Eight days post-induction (tumor starting volume <100 mm³), mice were randomized (n=8) and treated every 4 days intratumorally with PBS or 100 μg of CPMV, TMV, TMVshort, TMV CP, or SNP. Tumor volumes were measured daily and mice were sacrificed when tumors reached >1500 mm³ or 10% body weight.

As previously shown CPMV particles elicited a potent anti-tumor response in this mouse model and significantly slowed tumor growth rate and extended survival time compared to PBS (p<0.005, Mantel Cox log-rank, FIGS. 13A-D). Disassembled TMV CP had no effect on B16F10 tumor growth and progression. Interestingly, TMV and TMVshort slowed tumor growth and increased survival time (p<0.05, Mantel Cox log-rank, FIGS. 13A-D), however at significantly lower potency compared to that of CPMV. There were no apparent differences between TMV and TMVshort indicating the aspect ratio (and rate of phagocytosis) does not necessarily play a role in plant viral in situ vaccines.

Figure 13A:
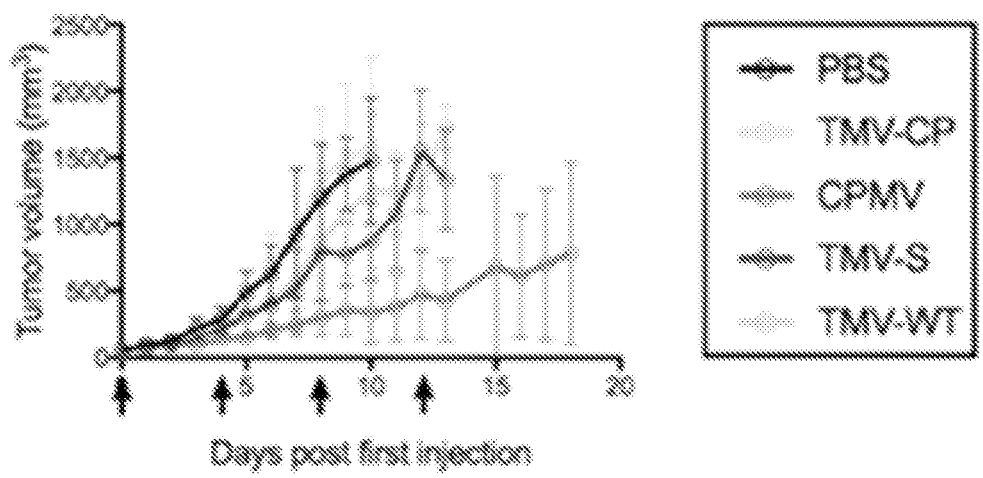
FIGS. 13A-F illustrate the efficacy study. Tumors were induced with an intradermal injection of 125,000 cells/mouse. Mice (n=8) were treated with 100 μg of particle or PBS control once every four days, starting 8 days post-induction. Arrows indicate in situ vaccination schedule. Time course tumor growth curves with overall growth (A), by treatment group (B), and compared at individual time-points (C). (D) Survival curve of mice post first in situ vaccination (time 0). (E) SNP Tumor growth curve [left] and survival curve [right]. (F) TMV dosing experiment tumor growth curve (100 μg vs. 500 μg).
Figure 13B:
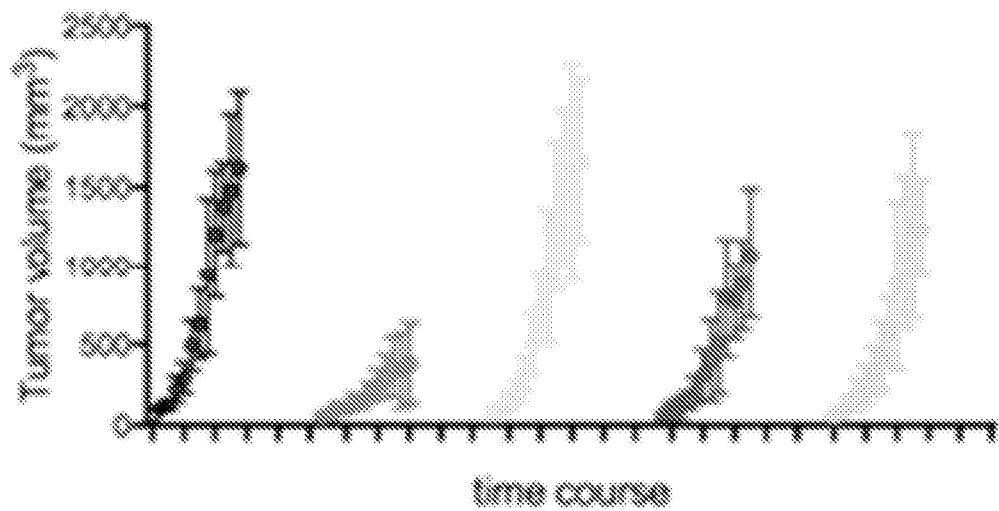
Figure 13C:
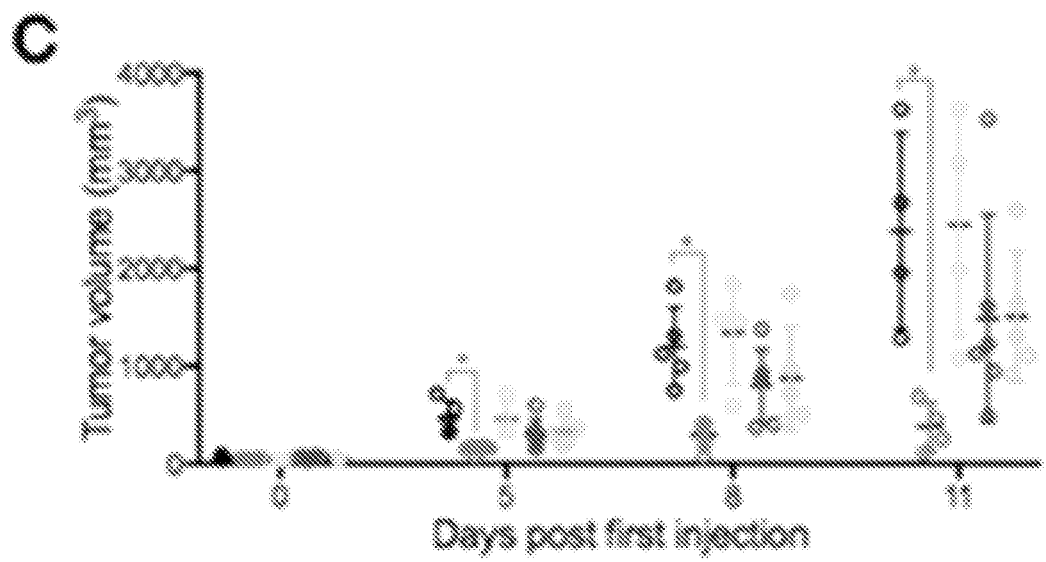
Figure 13D:
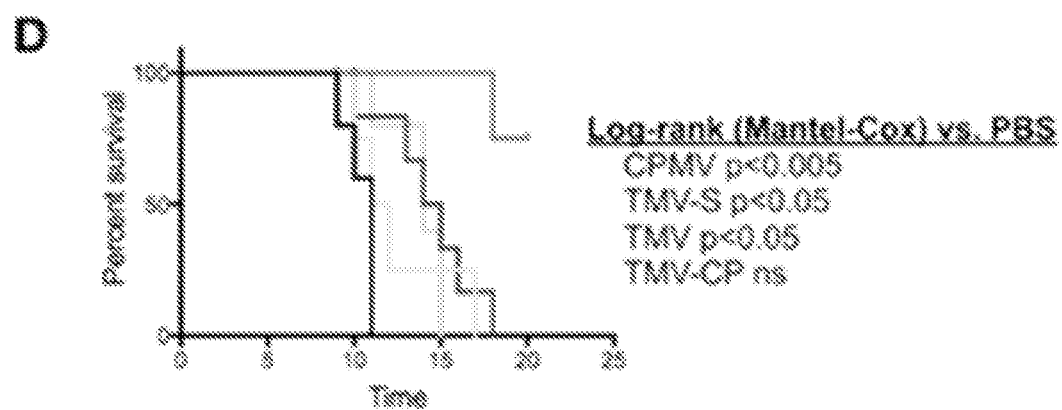
Figure 13E:
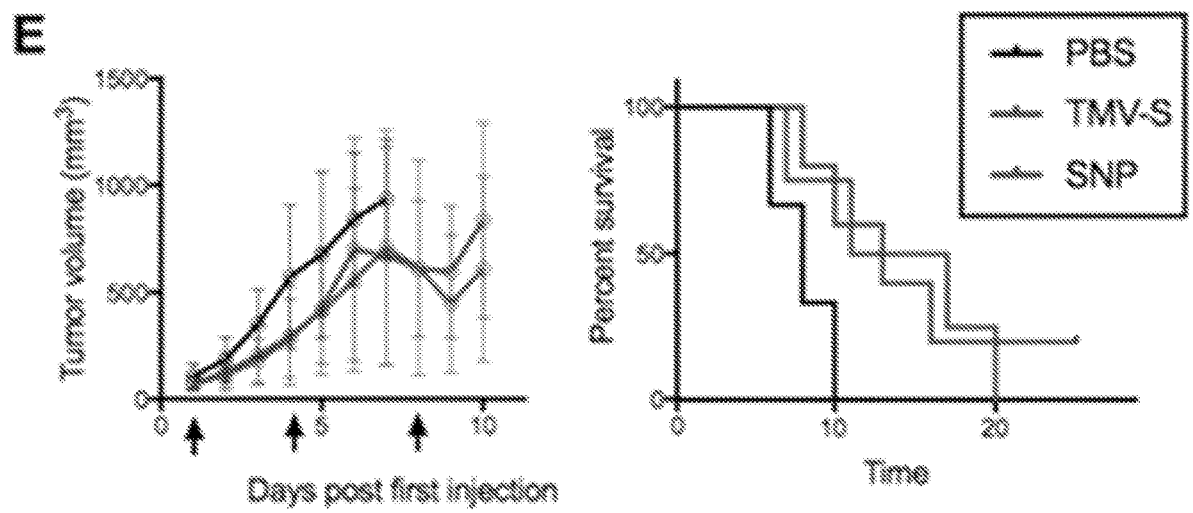

To address whether nanoparticle shape would impact the effectiveness of the TMV vaccine, TMVshort vs. SNP were tested side-by-side using the dermal B16F10 model: the SNP in situ vaccination approach also reduced tumor growth rates and thus increased survival time (FIG. 13E), nevertheless, the tumor growth curves and survival curves between the SNP and TMVshort groups indicated matched efficacy (it should be noted that the SNPs tested here were ~250 nm in size—we cannot rule out that SNPs of smaller diameters may trigger more potent responses and this question could be addressed in future work).

Figure 13F:
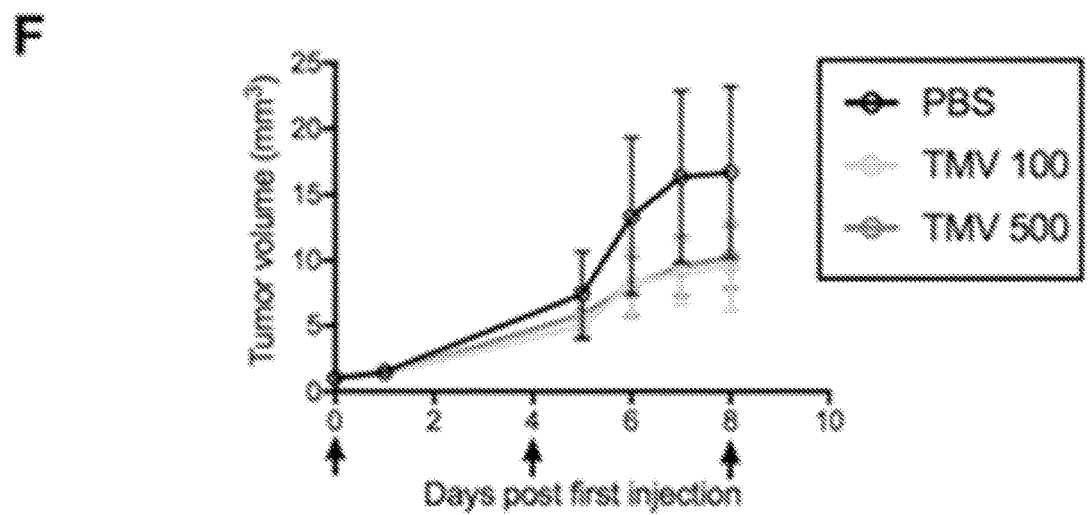

Lastly, to test whether increased dosing would allow to increase the potency of the TMV in situ vaccination approach, TMV was administered every 4 days, 8 days post B16F10 tumor establishment at a dosage of 100 μg vs. 500 μg (higher dosing is technically challenging to achieve, due to the small intratumoral injection volume of <20 μl): both dosing schedules led to slowed tumor growth rates vs. the PBS group, but there were no apparent differences between the treatment groups, indicating that higher doses do not increase efficacy (FIG. 13F).

In summary, while in situ vaccination with TMV, TMVshort, and SNP resulted in delayed tumor growth and increased survival time in mice with B16F10 tumors, no efficacy was observed when animals were treated with soluble CPs, thus indicating that mutivalency and particle assembly is a requirement. Nevertheless, neither shape nor aspect ratio were indicated as parameters influencing outcomes. While delayed tumor growth was observed after in situ vaccination with TMV, TMVshort, and SNP the significantly lower rate of efficacy compared to CPMV, may indicate distinct mechanism of action. To further investigate this immune cells and chemo/cytokine profiles were assessed in temporal studies as described below.

Cytokine Profiling of BMDCs and Tumor Cell Suspensions from Tumor-Bearing Animals Treated with CPMV Vs. TMV-Based In Situ Vaccine While immune cell profiling provides information on which cell types infiltrate and become activated within the TME in response to the viral in situ vaccine, cytokine and chemokine profiling provides clues about how this cellular response is orchestrated. Therefore, we first measured cyto/chemokine expression levels in vitro and ex vivo using either isolated BMDCs or homogenized tumor lysates. Furthermore, we performed a pathway analysis to gain insights into how these identified cyto/chemokines are interconnected and to gain clues about the key pathways that are being activated.

BMDCs were stimulated in vitro with PBS (negative control), TMV, CP, TMVshort, and LPS (positive control, TLR4 agonist) and cytokine/chemokine panels were assessed using Luminex 32-plex panels. Data indicate that all plant virus-based samples, including the free CPs are immune-stimulatory with no apparent differences between any of the formulations under the conditions tested (FIG.

14A). Nevertheless, it is difficult to draw conclusions from in vitro studies that only consider a single cell type in 2D culture, therefore in vivo studies were performed.

To determine whether CPMV vs. TMV particles elicit different cytokines profiles in vivo, B16F10 isografts were induced intradermally on the right flank of C57BL/6J mice. Eight days post-induction (tumor starting volume <100 mm$^3$), mice were randomized (n=4) and treated with PBS or 100 μg of CPMV, TMV, TMVshort, or TMV CP. Tumors were harvested at 24 hours post initial injection, homogenized, and prepared for Luminex assay. At 24 hours post treatment, data indicate that the TMV formulation elicited more profound cytokine/chemokines release within the TME compared to CPMV (FIG. 14B). Comparing the various TMV formulations, it appears that while both TMV and TMVshort prime immunostimulation within the TME, intratumoral treatment of B16F10 melanomas with free CP did not stimulate cytokine/chemokine release within the TME, which is in line with the lack of efficacy of free CP (FIG. 14B).

While somewhat similar, different trends could be observed comparing the cytokine/chemokines released upon TMV vs. TMVshort treatments, with the following cytokines and chemokines showing statistical significant differences between TMV vs. TMVshort: G-CSF, IL-1α, IL-3, IL-6, IL-17 were elevated for TMV, but not for TMVshort (or CPMV), while IP-10 and RANTES were elevated for the TMVshort vs. TMV (or CPMV). Overall it was apparent that in particular pro-inflammatory cytokines were upregulated in the TME post TMV treatment: IL-6 vs. PBS (p=0.006, fold change [fc]=13.4), IL-1β vs. PBS (p=0.0006, fc=8.9), IL-17 vs. PBS (p=0.002, fc=7.8), and TNF-α vs. PBS (p=0.005, fc=10.6). Furthermore, macrophage inflammatory proteins MIP-1β vs. PBS (p=0.006, fc 23.2) and MIP-2 vs. PBS (p=0.0002, fc=58) were up-regulated. Both chemokines are produced by macrophages and they activate granulocytes, such as neutrophils; as such these chemokines are also key players in inducing pro-inflammatory responses toward infection and inflammation. This may also be consistent with the observation that the cytokine G-CSF appears to be released upon TMV treatment with G-CSF vs. PBS (p=0.0001, fc=170) showing significant elevation in the TME (FIG. 14B).

At 24 hours, CPMV did not elicit a strong response for most of the cytokines/chemokines tested. Nevertheless, CPMV did have a statistical significant increase in the expression of in IFN-γ (p=0.009, fc=2.4) and the downstream IFN-γ-regulated genes IP-10 (p=0.001, fc=4.8), MCP-1 (p<0.0001, fc=4.5), RANTES (p<0.0001, fc=5.8), and MIG (p=0.0044, fc=3.1) (FIG. 14B).

Together the cytokine/chemokine profiles indicate that at early-time points (i.e., 24 hours post treatment), TMV and CPMV-based viral nanoparticle in situ vaccines, both activate the immune system with TMV having a more profound effect and cytokine/chemokine profiles appearing to be related to distinguishable pathways (see discussion below).

To gain insights into how the initial tumor cytokine/chemokine profile changes would maintain or change over time, we repeated the above Luminex experiments at four days post initial treatments on day one and day four. This time point was chosen, because at day 4-post first treatment, one can appreciate the anti-tumor effect based on the tumor growth curves that bifurcate for the various treatment arms (see FIG. 13). In these experiments (and studies going forward) we simplified our experimental set up and only considered PBS vs. CPMV and TMV; this was done because i) there were no apparent differences in efficacy comparing TMV vs. TMVshort and ii) there were no stark differences in the early cytokine profile.

At first glance, the Luminex results indicate that at 4 days, CPMV instead of TMV had the preeminent profile, or in other words that CPMV at this time point established a more robust cytokine/chemokine secretion within the TME (FIG. 14). Another considerable difference is that expression levels of cytokines and chemokines were significantly higher at 4 days compared to levels measured at the 24-hour time point.

Noticeably, the characteristic IFN-γ CPMV profile that was seen at 24 hours was maintained (FIG. 14C, yellow arrows; see also pathway analysis and discussion below). Moreover, another subset of cytokines and chemokines became apparent: this set includes Eotaxin (p=0.0003, fc=2.1), G-CSF (p<0.0001, fc=7.5), GM-CSF (p<0.0001, fc=11.3), IL-12 (p=0.02, fc=2.7), KC (p<0.0001, fc=8.2), MIP2 (p<0.0001, fc=14.5), and TNF-α (p<0.0001, fc=8.4) (FIG. 14C; green arrows highlight cytokines that were specific to CPMV; i.e., only CPMV showed statistically significant elevation of these cytokines).

Together data indicate that while TMV elicits a pro-inflammatory response upon injection, it does not establish a long-lasting response. In stark contrast, the onset of the CPMV induced cytokine/chemokine profile is delayed and distinct, likely due to initial recruitment and/or reprogramming of immune cells, which in turn mount more potent anti-tumor immunity. While data indicate differences in immune activation, the underlying mechanism for these differences are yet to be identified: it is possible that CPMV and TMV are recognized by different receptors, but it is also possible that different pathways are triggered due to differences in metabolic processing of CPMV vs. TMV. Answering these particular questions however was beyond the present study.

Immune Networks and Pathway Analysis Comparing CPMV Vs. TMV In Situ Vaccination

To gain a deeper understanding of the differential cyto/chemokine profiles measured within the TME upon in situ treatment of B16F10 dermal tumors with CPMV vs. TMV, immune network and pathway analysis was conducted. Cytokine pathway analysis is a powerful tool to gain insights into the global interplay of the immune mediators. Case Western Reserve University's Crosstalker software (https://sb4j.case.edu) was used for pathway analysis. Cyto/chemokines with significant expression levels (compared to PBS controls) and/or cyto/chemokines expressed differentially (with statistical significance) between the treatment arms CPMV and TMV were used as "seeds" for the computation. The Crosstalker software considers these "seeds" or entry points globally based on established networks—the output is a map of the identified signaling pathway highlighting how the different cyto/chemokine players are interconnected and how this may differ between the treatment arms.

At 24 hours compared to PBS, CPMV produced seven "seeds" that were significantly expressed: MCP-1, RANTES, IFN-γ, IL-5, MIG, IP-10, and M-CSF (FIG. 15B, seeds are shown in red). Computed protein networks and pathways are shown in FIG. 15; this analysis showed that CPMV-treated tumors were preferentially signaling through regulation of IFN-γ pathway (FIG. 15B, highlighted in green and aqua). At the same time point, when comparing PBS and TMV, 18 "seeds" that were significantly expressed were imported for analysis, of which the following 16 mapped to the software-predicted networks: IL-6, IL-3, M-CSF, LIF, MCP-1 and IL-1β, IL-4, IL-10 and MIP-1β, MIP-1α, TNF- α, IL-15, IL-17, KC, IL-7 and IL-1α (the following 2 "seeds" did not produce any hits with the predicted networks: IL-12 and MIP-2). The main pathways identified were IL-6 and IL-3 signaling pathways (FIG. 15C, highlighted in aqua and brown, respectively). Lastly, TMV vs. CPMV "seeds" were loaded into the Crosstalker software; and data further support that TMV and CPMV treatment activates distinct, non-overlapping pathways: for TMV signaling occurs through IL-6 and IL-3 (aqua and blue) and CPMV signaling occurs through IFN-γ (orange) and there was no apparent crosstalk between the involved immune mediators (FIG. 15D). These results corroborate that the different cyto/chemokine profiles measured at 24 hours are indeed a coordinated profile with distinct signaling pathways at play.

At 4 days post injection, as predicted by the Luminex data (see FIG. 15), there was a significantly higher level of immune activation in tumors from CPMV-treated animals; 21 significant "seeds" were identified with 17 mapped; chemokine signaling was most apparent: IFN-γ and GM-CSF, KC, TNF-α, MIP-1β, MIP-1α, RANTES, MCP-1, Eotaxin and IL-12p40, IL-17p70 and IL-10, IL-1β and MIP-2, IL-6, M-CSF, LIX (FIG. 15E). TMV vs. PBS only resulted in 12 "seeds" and data analysis indicated that TMV also preferentially enriched for chemokine inter-signaling (data not shown). Comparing CPMV vs. TMV showed 14 significant "seeds" and 9 could be mapped to IFN-γ signaling and regulation as well as TNF-α signaling (FIG. 15F, highlighted in red and orange): IL-10 and MIP-1β, MIP-1α, RANTES, TNF-α, GM-CSF, IFN-γ, Eotaxin, and IL-17 (FIG. 15F). Throughout the time points considered (24 hours and 4 days), IFN-γ signaling remained a key differentiator for CPMV. In addition, several cytokines emerged for the CPMV-treatment arm at 4 days, these include GM-CSF (CSF2) and Eotaxin (CCL11), both of which are interconnected to the main network, therefore further indicating manifestation of an IFN-γ-mediated antitumor response.

Overall, Luminex and pathway analysis are in agreement and support that CPMV vs. TMV intratumoral injection leads to immune activation, however distinct cyto/chemokine profiles were observed and data point toward distinct pathways of immune-activation and signaling.

Tumor Histology and Immunohistochemistry Comparing CPMV Vs. TMV In Situ Vaccination Tumor growth curves and cyto/chemokine analyses indicate differential efficacy of CPMV vs. TMV-based in situ vaccines based on inherent differences in immune activation. Therefore, histology and flow cytometry (see next section) were performed to gain insights into the immune cells at play. For histology and immunohistochemistry (IHC), dermal B16F10 tumor-bearing animals were treated with PBS, TMV vs. CPMV as described above; tumors were harvested and analyzed six days post first treatment (i.e., these animals received two treatments, one of day 1 and the second on day 4). First, tumors were stained with H&E to assess the gross tumor morphology. In sections, tumors were circumscribed, which was attributed to proper placement in the dermis (FIG. 16A-C). Due to the fast growth rate of the B16F10 tumors, there was a noticeable central necrosis (FIG. 16A-C middle row); central necrosis was apparent in all treatment groups; with a higher degree of necrosis being noticed in tumors from animals receiving the PBS sham treatment. B16F10 tumor morphology is characterized by sheets of cells that have diffuse nuclei (FIG. 16A-C, top inset). In areas of tumor death, the tumor tissue appears darker with nuclear condensation and reduction of cytoplasmic volume (FIG. 16B-C, bottom inset). Second, sections were stained for total leukocytes (CD45). At six days, PBS tumors showed minimal presence of leukocytes shown by the absence of red signal throughout the tumor (FIG. 16D). TMV treated tumors showed a presence of leukocytes that were concentrated pericentrally (FIG. 16E) while CPMV was littered with CD45$^+$ cells throughout the sections (FIG. 16F). The diffuse presence of CD45$^+$ correlated with the diffuse alteration of tumor morphology on H&E. This was the case at all time points (4 days and 10 days [data not shown]).

Flow Cytometric Analysis of B16F10 Tumors Receiving CPMV Vs. TMV In Situ Treatment Histology and IHC indicates differences in tumor morphology and increased infiltration of leukocytes into tumors of animals receiving the CPMV in situ vaccine (see FIG. 16). Flow cytometry analysis was used to gain further insights into the differences in immune cell profiles within the TME comparing PBS, CPMV vs. TMV treatment groups. Dermal B16F10 tumors were studied and treated as described above; tumor tissue was harvested at day four or ten days post first treatment. Day four was considered for innate panel analysis: four hours after the day four treatment (animals received two treatments; one on day one and one on day four), tumor tissue was collected and analyzed by FACS to characterize innate immune-cell infiltration. The numbers of live leukocytes (CD45$^+$) in tumors were increased in TMV (p=0.0192) and CPMV (ns) treated mice compared to PBS control group (FIG. 17A). However, among the elevated infiltrating leukocytes, CPMV treatment induced slightly more monocytic cells (FIG. 17E, p=0.0289), while TMV treatment induce more granulocytic cells (FIG. 17D, p=0.0056) in tumors, in particular granulocytic myeloid-derived suppressor cells (G-MDSCs, CD11b$^+$ LY6G$^{hi}$LY6C$^{lo}$) (FIG. 17G, p=0.0005 vs. PBS and p=0.0013 vs. CPMV). While MDSCs have been considered to promote tumor growth and induce CD8$^+$ T cell tolerance, G-MDSCs can also be converted to neutrophils in the presence of GM-CSF. Significant increase of GM-CSF levels were found in the TME in response to CPMV and TMV treatment (see FIG. 17). Therefore, these changes could lead to G-MDSC activation and enhanced phagocytic function leading towards a better prognosis. In line with this discussion, both treatments induced recruitment of tumor-infiltrating neutrophils (TINs, CD11b$^+$LY6G$^{hi}$F4/80$^+$), however only the CPMV group showed statistical significance (p=0.0227). Lastly, CPMV-treated tumors showed high levels of proportions of NK cells (FIG. 17I, p=0.0034 vs. PBS and p=0.0108 vs. TMV).

We also evaluated the population of infiltrated monocytic MDSCs (M-MDSCs, CD11b$^+$LY6G$^-$LY6C$^+$) among different treatment groups (FIG. 17F) and found that CPMV treatment resulted in higher cell population of M-MDSCs compared to TMV or PBS. M-MDSCs have the ability to differentiate to macrophage and DCs under appropriate cytokines/chemokines stimulation (e.g., GM-CSF). Different trends in tumor-infiltrated dendritic cells (CD11b$^+$CD11c$^+$) and macrophage (CD11b$^+$F4/80$^+$) populations were also observed comparing CPMV vs. TMV: the percentages of both, DCs (p=0.0143) and macrophages (p=0.0023) significantly increased in CPMV-treated mice; in contrast, these cell populations decreased in TMV-treated mice (p=0.0008 for DCs; p<0.0001 for macrophages) (FIG. 17B-C).

Next, tumors were collected at later time points, i.e. 10 days post first treatment to investigate whether adaptive immune responses are mounted by either treatment. CPMV treatment led to significant recruitment of both, CD4$^+$ (p<0.0001) and CD8⁺ (p=0.0040) T cells. TMV treatment only enhanced the CD4⁺ T cells infiltration (p=0.0023) (FIG. 17J+K). To assess whether memory T cells were generated in tumor tissues after treatments, the levels of effector memory T cells (EMT, CD44⁺CD62L⁻) were quantified. Higher proportion of effector memory CD4⁺ (p=0.0001) and CD8⁺ (p=0.0040) T cells were found in CPMV-treated mice (FIG. 17L) whereas the TMV treatment only accumulated higher level of CD4⁺ EMT (p=0.0287) (FIG. 17M).

Together, these results indicate that CPMV and TMV in situ vaccination of B16F10 tumors accelerates the recruitment of innate and adaptive immune-cell in TME; with TMV and CPMV leading to the recruitment of differential immune cell profiles; these differences alongside with the observed distinct cyto/chemokine profiles explain the observed differential potency of CPMV vs. TMV applied as in situ vaccine.

While the potential of mammalian viruses or other microbes in medicine has long been recognized, the application of plant virus-based materials, in particular their use as in situ vaccines is a novel and emerging field. Recent data indicate that plant viral nanoparticles and virus-like particles thereof can stimulate an anti-tumor response when administered as in situ vaccine. While plant viruses are neither oncolytic or do they replicate or infect mammalian cells, it is thought, that plant virus-based nanoparticles activate the innate immune system locally through interaction with PRRs, thereby re-programming the immunosuppressive TME toward an immune-activated state. This in turn restarts the cancer immunity cycle leading to systemic elimination of cancer cells through the adaptive immune system. Previously, it has been shown that nanoparticles from CPMV (a 30 nm-sized icosahedron) and filamentous platforms PapMV and PVX can induce anti-tumor responses upon intratumoral application. The high aspect ratio filamentous particles were able to significantly decrease the growth of the tumors and increase survival upon intratumoral administration. Furthermore, these particles were able to modulate intratumoral cytokine and chemokine production. Nonetheless, neither was able to eliminate tumors as was seen with the nanoparticles from CPMV. Here we demonstrate that CPMV, and to a lesser degree TMV, elicits anti-tumor immunity after intratumoral treatment in a mouse model of dermal melanoma. Comparing the various TMV-based formulations: native 300×18 nm-sized TMV vs. TMVshort measuring ~50×18 nm vs. SNP, there was no difference in efficacy or underlying immune-stimulation—each formulation elicited a pro-inflammatory response that resulted in moderately slowed tumor growth. The free CPs did not elicit an anti-tumor response or immune-stimulation, which may indicate that a multivalent assembly is required to trigger innate immune recognition and activation. Differential potency of CPMV vs. is explained with differences in immune activation. While the initial receptor recognizing CPMV has not been identified yet, data indicate that CPMV stimulates an anti-tumor response through recruitment of monocytes into the TME, establishing signaling through the IFN-γ pathway, which also leads to recruitment of TINs and NKs. Data indicate that initial priming of the innate immune system mounts also an adaptive response with CD4⁺ and CD8⁺ T cell recruitment and establishment of effector memory cells. While the TMV treatment also lead to the recruitment of innate immune cells as well as T cells (although to a lesser degree), key differences were noted in cyto/chemokine profiling with TMV inducing a potent immune response early on characterized by strong pro-inflammatory cytokines, primarily IL-6. While CPMV had more modest responses early, but those responses were much higher by day four compared to TMV and that would make a clear biological difference. Additionally, and perhaps surprisingly, only CPMV made high levels of IFN-γ early or late and this cytokine is commonly associated with potent T cell mediated antitumor immunity.

It is clear that further research is required to fully elucidate the mechanism of plant viral in situ vaccines. Our data indicate that some plant viral nanotechnology platforms are more potent than others, the enhanced efficacy of CPMV vs. TMV-based nanoparticles could be explained with underlying differences in immune activation. The question as to how or why CPMV in particular is more effective requires further investigation, i.e., a critical question to answer would be what is the molecular receptor that recognizes CPMV and initiates and orchestrates the potent anti-tumor immune response. Once this question is answered one may test this hypothesis by re-engineering TMV or other platforms to target the identified receptor and/or pathway. Understanding the intricate differences and underlying mechanism of immune activation of different (plant) virus-based platforms may set the stage for clinical development of these technologies.

Example 5

We demonstrated that in a syngeneic, orthotopic mouse model of ovarian cancer, weekly intraperitoneal (IP) treatment using the CPMV in situ vaccine significantly delayed tumor growth and improved survival. Injection of CPMV into cancer tissue induced a potent immune response that is thought to be related, in part, by conversion of the resident immune suppressive neutrophils present in tumors to pro-inflammatory type neutrophils. These activated neutrophils are capable of both directly killing tumor cells and priming T cells and NK cells toward antitumor activity. While IP infusions of chemo-therapies are currently approved for use clinically, and have been shown to provide a survival advantage in the treatment of ovarian cancer, this method of administration is underutilized. In contrast to intravenous (IV) administration that can be done in the out-patient setting, IP administration often requires a hospital admission leading to increased cost and decreased quality of life. Therefore, to alleviate the need for repeat administration, we set out to develop a slow-release formulation of the CPMV in situ vaccine that would maintain sustained immune stimulation without the need for repeat IP injections. Maintaining an immunostimulatory effect through depot formation could reduce the number of IP administrations, making this treatment strategy more attainable for clinical implementation.

A number of slow-release formulations of cancer drugs and immune-therapies are currently under investigation; these include hydrogels for delayed release of tumor associated antigens, chemotherapeutics, and a variety of other cargo including nucleic acids, as well as microparticle and microneedle administration of antibodies for immunotherapy. These diverse approaches all seek to improve cancer treatment efficacy by maintaining a constant therapeutic concentration and improve cancer patient quality of life by reducing the number of administrations.

In this example, we aimed to develop slow-release assemblies of CPMV making use of charged dendrimers and electrostatic self-assembly protocols. While zwitterionic in nature, CPMV carries an overall negative surface charge, therefore we chose to program coassembly with positively-charged polyamidoamine (PAMAM) dendrimers. A variety of different dendrimer formulations are under investigation for use in drug delivery and nanomedicines; they have the advantage of being highly tunable, multivalent, and possessing a low polydispersity. In addition to their use in drug delivery, dendrimers have been used in combination with oncolytic adenovirus in order to improve intratumoral accumulation and in virus-dendrimer assemblies as a method to create well-controlled higher order structure on a nanoscale-to-mesoscale level. PAMAM dendrimers in particular are well-understood, uniform, and commercially available; our lab has successively used them in the past to create virus-dendrimer hybrid materials for photon capture applications. The potential for in situ vaccination applications using virus-dendrimer hybrids however, has not yet been fully explored. Therefore, we investigated the assembly and disassembly of CPMV-dendrimer hybrids, their IP trafficking, and efficacy of treatment using them in a mouse model of ovarian cancer.

Experimental Section

Preparation of CPMV Nanoparticles and Generation 4 PAMAM Dendrimer

CPMV was propagated in black-eyed pea plants (*V. unguiculata*) and isolated using previously reported protocols.

For biodistribution studies, the CPMV particles were conjugated with an Alexa Fluor 647 dye (NHS-AF647) using a previously described reaction. In brief, dye labeling was carried out overnight at a concentration of 2 mg mL$^{-1}$ CPMV in 0.1 m potassium phosphate buffer (pH 7.0) and 10% DMSO with an excess of 2000 dyes per CPMV. The dye-functionalized CPMV particles (CPMV-AF647) were purified by ultracentrifugation and characterized using UV-vis absorption spectroscopy using a Nanodrop instrument. Dyes per particle were determined using the extinction coefficients and absorption maximums 8.1 mg$^{-1}$ cm$^{-1}$ at 260 nm for CPMV and 270 000 m$^{-1}$ cm$^{-1}$ at 650 nm for AF647 (per company website). Attachment was confirmed with electrophoresis using 4-12% NuPage bistris gels (Invitrogen).

Generation 4 PAMAM dendrimers with an ethylenediamine core (10 wt % in methanol) used in the study was purchased from Sigma Aldrich. PAMAM-G4 was isolated by removing methanol through rotary evaporation and resuspended in MilliQ water at a 10 mg mL$^{-1}$ concentration.

Dynamic Light Scattering

To study the assembly and disassembly of CPMV-G4 DLS measurements were performed: CPMV (≈50 mg mL$^{-1}$ in 0.1 m PBS, pH 7.0) and PAMAM-G4 dendrimers (10 mg mL$^{-1}$ in MilliQ water) were mixed at 0.15 mg mL$^{-1}$ of virus and 0.15 mg mL$^{-1}$ dendrimer concentration. The ionic strength was modified by adding small amounts of either 2 M NaCl or 10×PBS stock solutions. The hydrodynamic radius of the virus-polymer assemblies was measured using a DynaPro Nanostar DLS instrument (Wyatt Technology, Goleta, Calif.) at a wavelength of 658 nm, 90° scattering angle, 25° C.

Atomic Force Microscopy

The morphology of the CPMV-G4 assemblies was imaged using a 5500 atomic force microscope (Keysight Technologies, Inc., formerly Agilent Technologies) in tapping mode. High-resolution noncontact gold-coated NSG30 silicon cantilevers (NT-MDT Spectrum Instruments, Tempe, Ariz.) with a resonant frequency of 240-440 kHz were used and mounted onto the piezoelectric scanner for AFM imaging. The resulting AFM images were processed using Gwyddion Ver. 2.47.

Ovarian Cancer In Vivo Efficacy and Biodistribution

Animal studies were carried out using IACUC-approved protocols. Female C57BL/6 mice (Jackson Labs) were injected intraperitoneally with 2 million cells of the highly aggressive, luciferase-positive, murine ovarian cancer cell line ID8-Defb29/Vegf-A in sterile PBS. ID8-Defb29/Vegf-A cells were transfected with luciferase as previously described. Cancer cell growth was monitored using the Perkin Elmer IVIS Spectrum; mice were injected intraperitoneally with luciferin (15 mg mL$^{-1}$, 150 µL intraperitoneally) and imaged 5 min postinjection with a 3 min exposure time. Total luminescence was determined using Living Image software and total counts per mouse were graphed. Treatment was initiated 7 d following cell injection and administered either weekly (PBS and CPMV 100 µg per mouse) or once (1 mg CPMV and 1 mg CPMV in the described CPMV-G4 assembly). CPMV-G4 was vortexed immediately prior to injection. Prior to treatment group assignment, total luminescence was determined on day seven and used to match total cancer burden between treatment groups (n=5-6).

For biodistribution studies, mice were injected with 2 million ID8-Defb29/Vegf-Luc cells intraperitoneally and cancer cells were allowed to grow for 1 week. Following establishment of intraperitoneal disease as determined by IVIS imaging, mice were injected with PBS, 1 mg of AF647-CPMV, or 1 mg of AF647-CPMV-G4. Mice were imaged prior to injection, immediately after injection, and at times 1 h, 3 h, 6 h, 12 h, 24 h, 48 h, 72 h, 7 d, 11, and 14 d. Images were obtained in Spectral unmixing mode and each time-point was unmixed to isolate AF647 signal using the same library; an unmixing library was established separately for each cage immediately following injection. ROI analysis was performed on unmixed images from each time-point and radiant efficiency ((p s$^{-1}$ cm$^{-2}$)/(µW cm$^{-2}$)). Graphed relative fluorescence intensities are a summary of two successive biodistribution studies of n=1 followed by n=2.

Results and Discussion

Formation of the CPMV-G4 Assembly

CPMV was propagated in and isolated from black-eyed pea plants. Molecular farming of pharmaceuticals in plants is advantageous because plant-based production avoids contamination with mammalian pathogens or contaminants such as endotoxins. In recent years, plant virus-based nanotechnologies have been recognized for their possible applications in human health. Their well-defined nanoscale structures in combination with genetic and chemical programmability make them an attractive platform technology. CPMV is the type member of the comovirus genus in the family Comoviridae. Members of this family are also known as plant picorna-like viruses as they share similarities in structure, genome organization, and replication strategy with animal picornaviruses. CPMV infects legumes and was first reported in *Vigna unguiculata*. In sys-temic infected plants CPMV typically causes mosaic or mot-tling symptoms. CPMV has a bipartitite positive-sense RNA genome encapsidated separately in isometric, icosahedral nano-particles measuring 30 nm in diameter. The structure of CPMV is known to near atomic resolution. The virions are formed by 60 copies each of a small and large coat protein yielding a pseudo T=3 symmetry.

While the CPMV structure, like any proteinaceous macromolecule, is zwitterionic and patchy in nature, the electrostatic surface map and zeta potential measurement indicate that the net surface charge is negative=−12 mV), thus enabling coassembly with positively charged polymers.

Figure 18A:
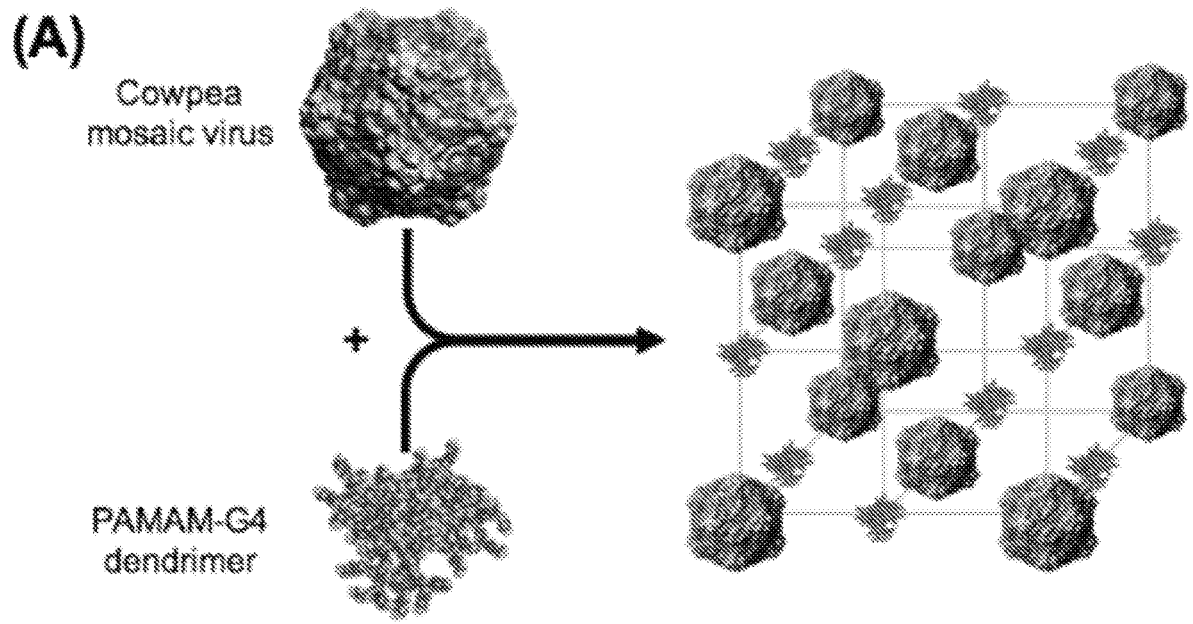
FIGS. 18A-E illustrate A) Schematic illustration of the assembly of CPMV with PAMAM-G4 dendrimer (space model with minimized energy calculated using Spartan software). DLS measurements for the assembly and disassembly of CPMV and PAMAM-G4 dendrimer in B) increasing NaCl and C) PBS concentrations. D) Stability study for the CPMV-G4 assembly, wherein the ionic strength was initially fixed at 25×10$^{-3}$ m NaCl for 1 week, gradually increased, and was kept at 300×10$^{-3}$ m NaCl for another 7 d. E) Aggregates of high concentration (2.5 mg mL$^{-1}$) CPMV and PAMAM-G4 in 25×10$^{-3}$ m NaCl, UV-vis spectroscopy of the supernatant from these aggregates was found to be below the linear range for detection of protein in solution indicating that there is minimal CPMV remaining in the solution
Figure 18B:
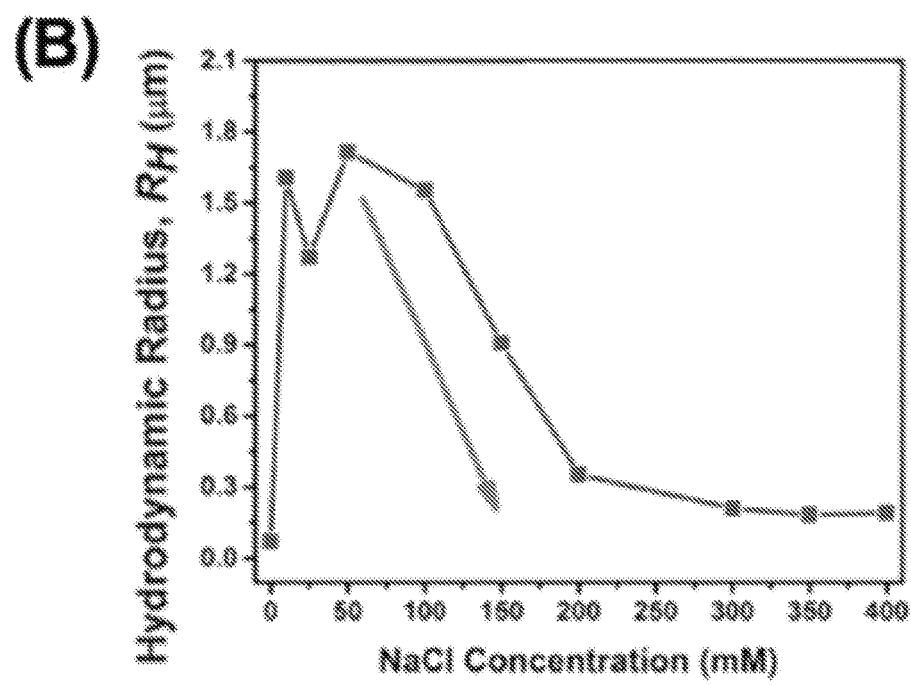
Figure 18C:
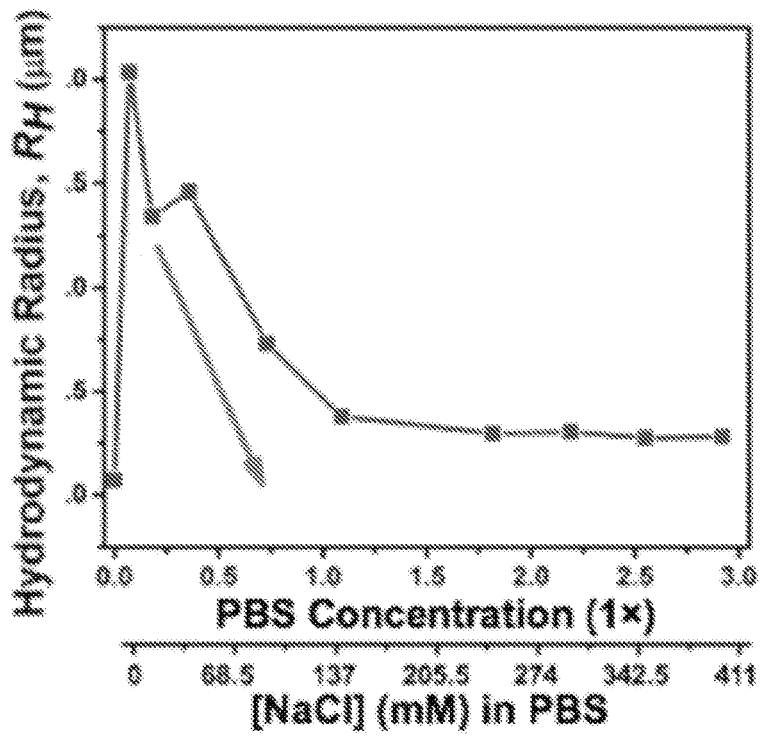

FIG. 18A depicts the overall assembly scheme; the electrostatically driven assembly of the CPMV nanoparticles with the amine-terminated generation 4 PAMAM dendrimer was investigated through dynamic light scattering (DLS) measurements. Combining both, CPMV and G4, at a concentration of 0.15 mg mL$^{-1}$ each in pure MilliQ water immediately resulted to an increase in hydrodynamic radius RH; from 15 nm (for CPMV), 56% of the assembly increased to an RH of 71±5 nm, while 44% measured to be 841±363 nm. Increasing the ionic strength to 10×10$^{-3}$ m NaCl abruptly induced the formation of larger aggregates with diameters greater than 1.5 μm (97% of the assemblies). These large aggregates, which constituted at least 96% of the assemblies, were observed at salt concentrations up to 150×10$^{-3}$ m; higher concentrations gradually disassembled the CPMV-G4 aggregates, with concentrations greater than 200×10$^{-3}$ m forming aggregates with two RH distributions aver-aging at 10-13 nm (25% of the assemblies) and 200-350 nm (75-78% of the assemblies) (FIG. 18B). A similar trend was observed when a related experiment was conducted with increasing phosphate buffered saline (PBS) concentration. From 0.07 to 0.36×PBS, which corresponds to approximately NaCl concentrations of 10 to 50×10$^{-3}$ m, 95-99% of the assemblies reached an RH between 1.3 to 2 micrometers; less than 5% of the assemblies had diameters less than 150 nm. The hydrodynamic radius of the assemblies gradually decreased starting at PBS concentrations higher than 0.36×, while other smaller aggregates with RH<10 nm start to be observed as well (FIG. 18C). At 3.65×PBS, 7% of the assemblies have an RH of 14 nm, which may correspond to CPMV; 65% resulted to 2.46 nm which could be aggregated PAMAM dendrimers; only 30% of the assemblies maintained an RH of ≈250 nm. These data indicate that the presence of a low salt concentration promotes formation of larger aggregates; while CPMV and the G4 dendrimers still have some interaction at zero salt concentration, as indicated by the measured hydro-dynamic radius of 70 nm for 56% of the assembly, the repulsion between the positively charged G4 limits greater aggregation in the absence of ions for some electrostatic shielding. When the salt level is increased too high however, salt screening effects limit the interactions between the dendrimers and CPMV, thus reducing overall aggregate size. These properties are thought to be useful for in vivo biomedical applications, i.e., the use of slow-release formulation: at low salt the assembly is triggered, and postinjection into the tissue, under physiologic salt concentrations (136-145×10$^{-3}$ m), disassembly and CPMV release is induced.

Figure 18D:
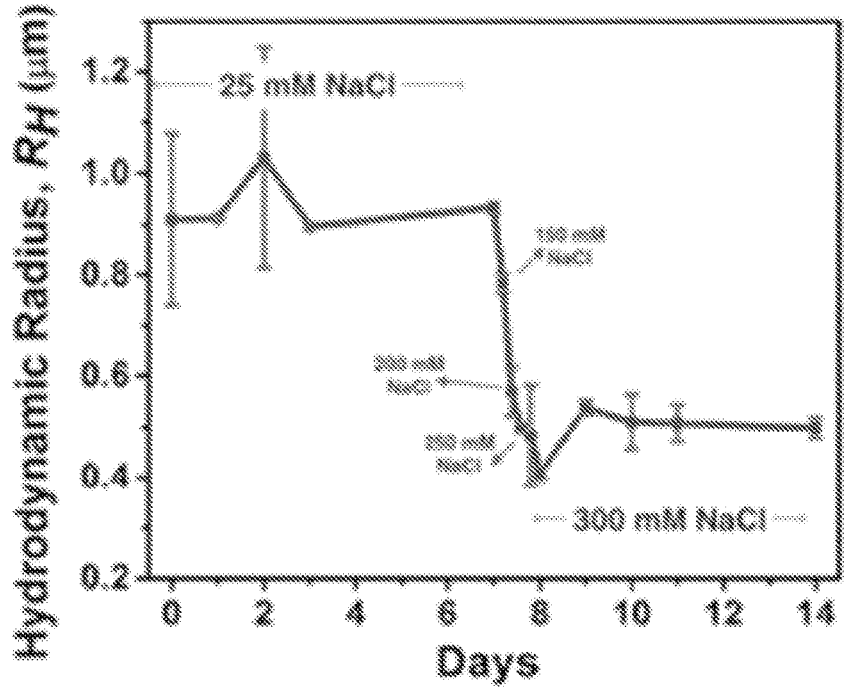

The stability of the CPMV-G4 assembly was investigated by storing the mixture in a low ionic strength environment (25×10$^{-3}$ m NaCl) for a week, disassembled by gradually increasing the salt concentration, and held in high ionic strength conditions (300×10$^{-3}$ m NaCl) for another week. The assembly maintained its large hydrodynamic radius at low salt concentrations for 7 d. Exposure to higher ionic concentrations (150-300×10$^{-3}$ m NaCl) led to a burst release into smaller aggregates with an RH of 500 nm; then slow decrease in size that may indicate slow-release of CPMV from the smaller aggregates (FIG. 18D).

Figure 18E:
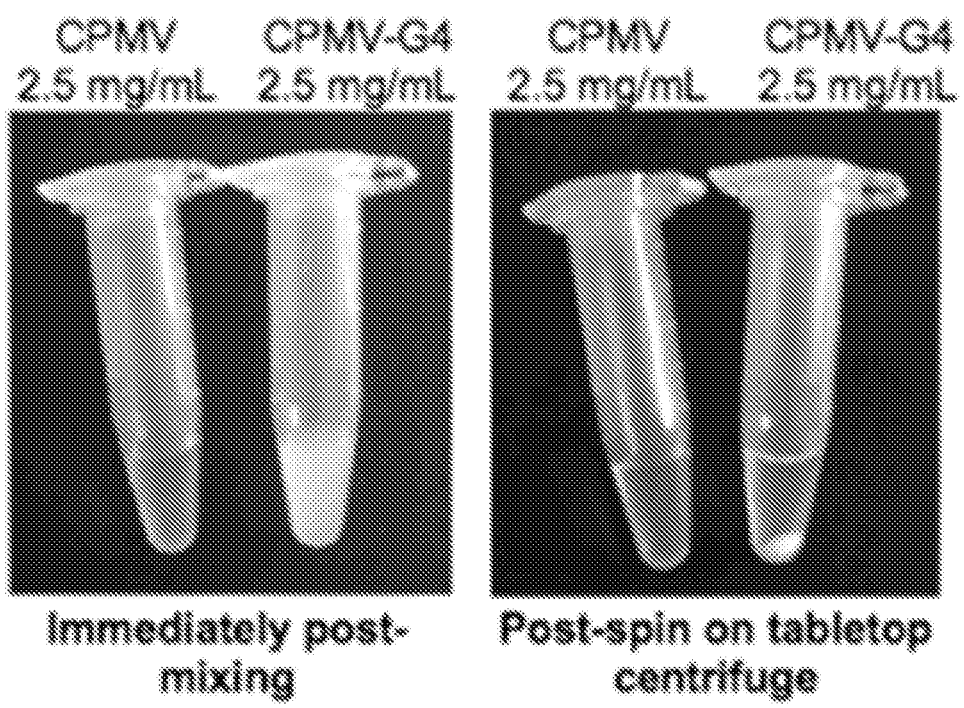

For animal studies, the concentration of CPMV was increased to 2.5 mg mL$^{-1}$ to form larger aggregates and reduce the total volume of injection necessary, this concentration resulted in aggregates large enough to immediately become visible upon mixing but still capable of being resuspended in solution and passed easily through a syringe. The CPMV:G4 ratio was maintained at 1:1 and salt concentration was kept low (25×10$^{-3}$ m NaCl). Due to the high concentra-tion of CPMV and G4, large aggregates formed immediately and RH could not be determined by DLS, supporting that the aggregates were at least larger than 2.5 μm. A cloudy appearance was observed immediately and aggregates were collected at the bottom of the tube following a brief spin using a tabletop centrifuge following a 30 s spin in a tabletop centrifuge at 15 000×g, indicating successful formation of CPMV-dendrimer aggregates (FIG. 18E). UV-vis spectroscopy of the supernatant from these aggregates was found to be below the linear range for detection of protein in solution indicating that there is minimal CPMV remaining in the supernatant and the overwhelming majority of CPMV interacts with PAMAM-G4 to form the visible aggregates. The colloidal suspension was mixed well prior to use in animals.

Figure 19A:
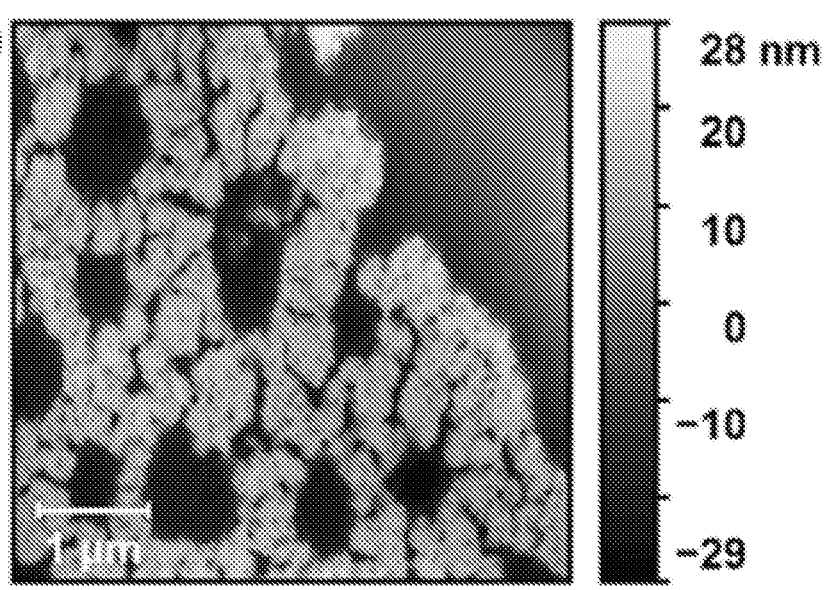
Figure 19D:
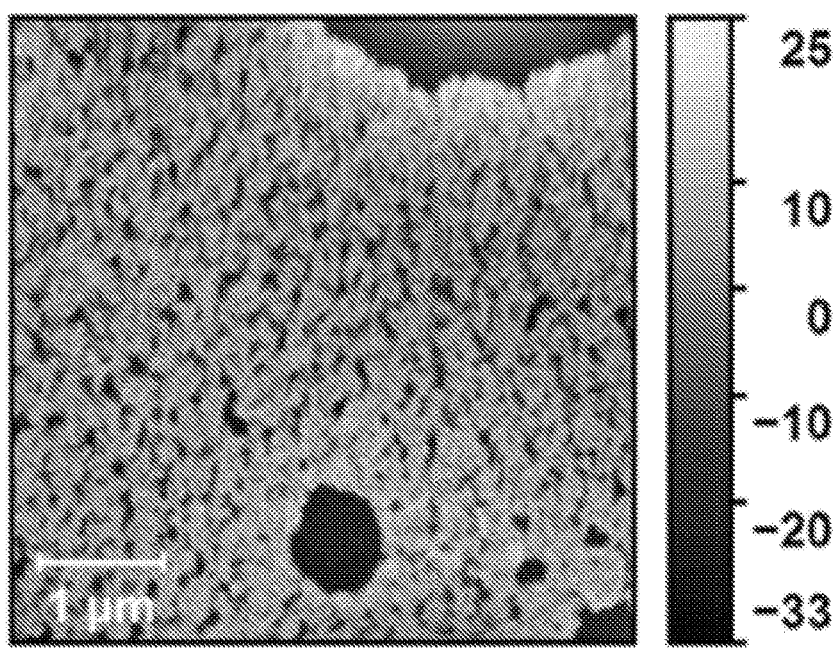

The morphologies of the assemblies were further investigated through tapping mode-atomic force microscopy (AFM). A 0.15 mg mL$^{-1}$ solution of CPMV, in the absence of the G4 dendrimer, shows areas of packed CPMV when cast on a freshly cleaved mica surface, however the presence of large empty spaces demonstrates that there are not strong interactions between the nanoparticles (FIG. 19A). In contrast, when 0.15 mg mL$^{-1}$ CPMV is mixed with G4 at a 1:1 ratio in a salt-free solution, particles form large areas of tightly packed CPMV nanoparticles on the surface (FIG. 19B). Increasing the ionic concentration to 50×10$^{-3}$ m NaCl induced formation of stacks of packed CPMV nanoparticles (FIG. 19C), indicating further increased interactions between CPMV and the G4 dendrimers. At higher ionic concentration (150×10$^{-3}$ m NaCl) a layer of tightly arranged CPMV formed, similar to the formation observed in the absence of salt (FIG. 19B,D), supporting the conclusion that high salt concentrations reduce formation of large aggregations. Overall, the morphological variations of the CPMV-G4 assembly correlate to the DLS hydrodynamic radius measurements, which exhibit the responsive assembly and disassembly of the electrostatic interactions as a function of salt concentration.

These findings are in agreement with previous work showing that increasing salt concentrations reduce the size of aggregate formation through reducing electrostatic interactions between dendrimers and viral nanoparticles. While salt concentration has been known to be important in the assembly formation of virus-dendrimer hybrid materials, to our knowledge, the disassembly of these hybrid materials has not been investigated or utilized for biomedicine.

Together, our data indicate that while the larger aggregates are stable for extended periods of time at low salt concentrations, the larger structures disassemble at ionic concentrations found in the IP space, sodium concentrations in the IP space are similar or slightly lower than found in serum (136-145×10-3 m). Even at the highest salt concentration measured however, CPMV-G4 aggregates would still be too large to passively diffuse across blood vessels to enter systemic circulation from the intraperitoneal space (size limit <100 nm) and would require disassembly or lymphatic drainage for eventual clearance. Further, the slow time course of disassembly of the aggregates at physiological salt concentrations (FIG. 18C), makes this assembly a promising candidate for continued presence in the IP space with slow release over time.

Treatment of Ovarian Cancer in a Syngeneic Mouse Model

Treatment efficacy of the CPMV-G4 formulation was assessed using an aggressive, syngeneic, and orthotopic mouse model of ovarian cancer. To monitor tumor development, we transfected the cells with luciferase. Treatment was started 1 week following injection of 2 million ID8-Defb29/

Figure 20A:
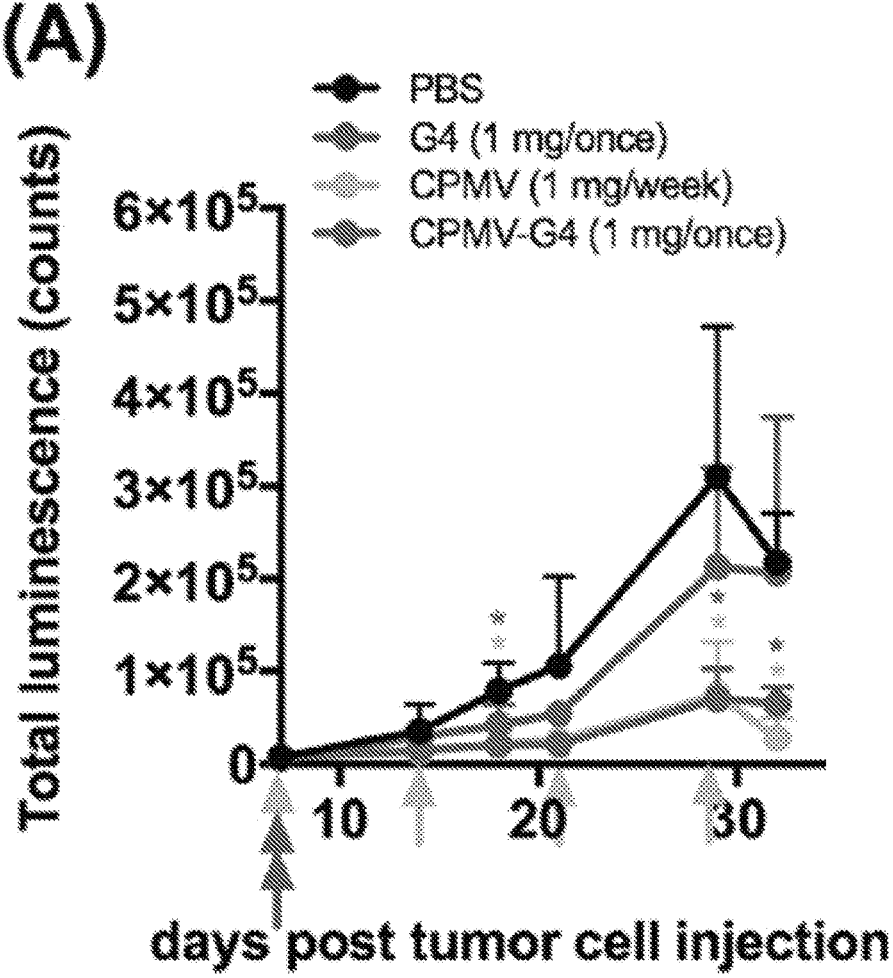
FIGS. 20A-B illustrate growth of ovarian cancer cells in the intraperitoneal space. Treatment was injected intraperitoneally 7 d following injection of 2 million luciferase-positive ID8-Def29/Vegf-A cells. Injection of each treatment group is indicated with a color-coordinated arrow. PBS was also injected weekly. Total bioluminescence was measured in intraperitoneal space until ascites development was apparent in the PBS control group (n=5-6). PBS/weekly in black, G4/1 mg once (normalized to the amount of G4 in CPMV-G4) in blue, CPMV-G4/1 mg once in purple, CPMV/1 mg weekly in orange, CPMV/100 μg weekly in red, CPMV/1 mg once in green. Graphs represent two successive experiments. (*p<0.05 as calculated by Excel two-tailed t-test when treatment group is compared to PBS, no statistical difference was found was between G4 only and PBS or a PBS and a single injection of CPMV 1 mg).

Vegf-A-Luc cells into the IP space using female C57BL/6 mice. Establishment of disease was confirmed and then monitored using in vivo imaging system (IVIS) imaging. Groups were treated with the following treatments: a single dose of 1 mg of CPMV versus a single dose 1 mg CPMV equivalent of CPMV-G4 versus 100 µg of free CPMV administered weekly (100 µg per week is the dosing previously shown to be effective at treating ovarian cancer growth); intraperitoneal PBS was administered as a control. An additional study compared 1 mg PAMAM-G4 alone to 1 mg CPMV equivalent of CPMV-G4. A dose of 1 mg was chosen for delayed release formulations as it provides a high enough initial dose for continuous release while still being well tolerated in treated animals. Disease burden was monitored twice weekly by tracking total luminescence indicating cancer cell growth. As it is difficult to directly compare tumor growth curves in studies not conducted at the same time these studies are plotted separately (FIG. 20A,B).

Figure 20B:
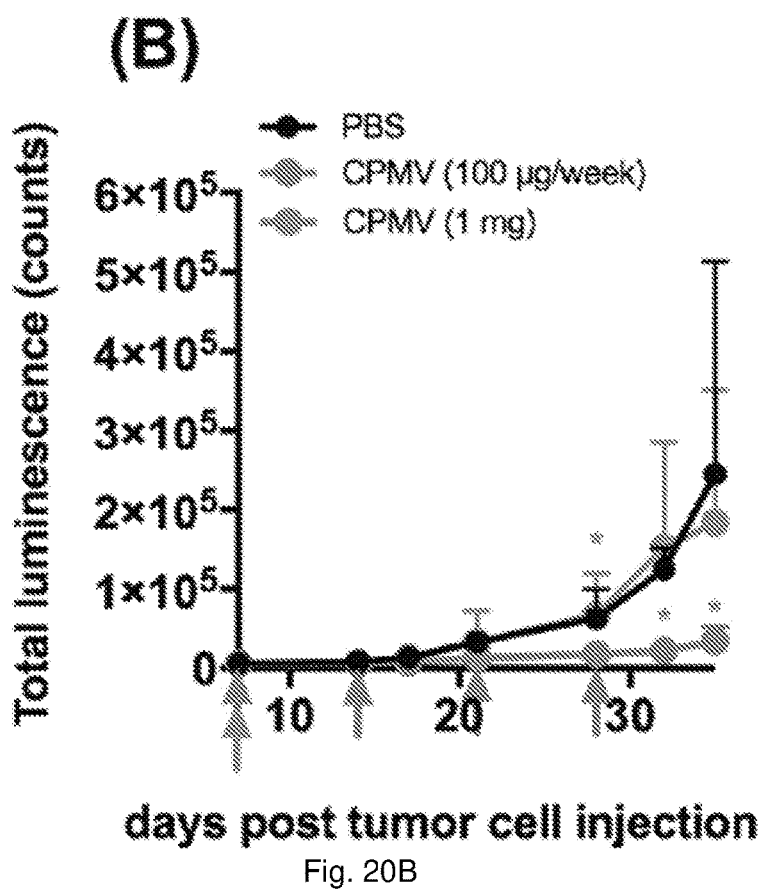

Tumor burden in mice treated with a single dose of CPMV-G4 (1 mg) was very similar to total luminescence observed in mice treated weekly with soluble CPMV (100 µg), and both treatment groups had significantly delayed cancer cell growth (FIG. 20). In contrast, a single 1 mg dose of soluble CPMV did not slow tumor growth, indicating that not the total dose but the treatment schedule, (maintaining the therapeutic CPMV concentration within the IP space over prolonged periods), is critical (FIG. 20). The G4 administered alone did not have a significant effect on tumor growth—while not statistically significant, there is trend that tumors grow slower in mice treated with G4, likely due to nonspecific cytotoxicity and immune stimulation associated with PAMAM dendrimers.

Together these studies indicate that CPMV-G4 assemblies can function as depots for slow-release of the CPMV in situ vaccine, prolonging its therapeutic efficacy in a mouse model of ovarian cancer after a single IP administration. The retention of CPMV when administered as soluble versus assembled formulation in the IP space was further tested by examining the biodistribution of fluorescently labeled CPMV and CPMV-G4.

Biodistribution of CPMV-G4 Adminis-tered Intraperitoneally

Figure 21A:
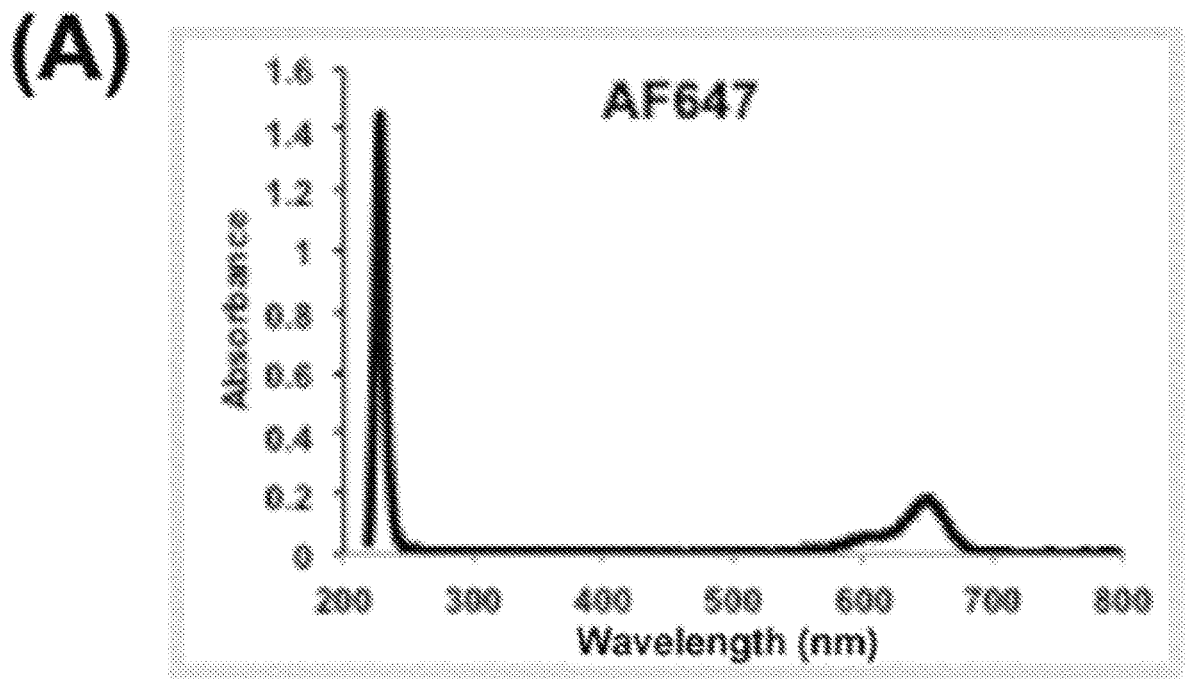
Figure 21A:
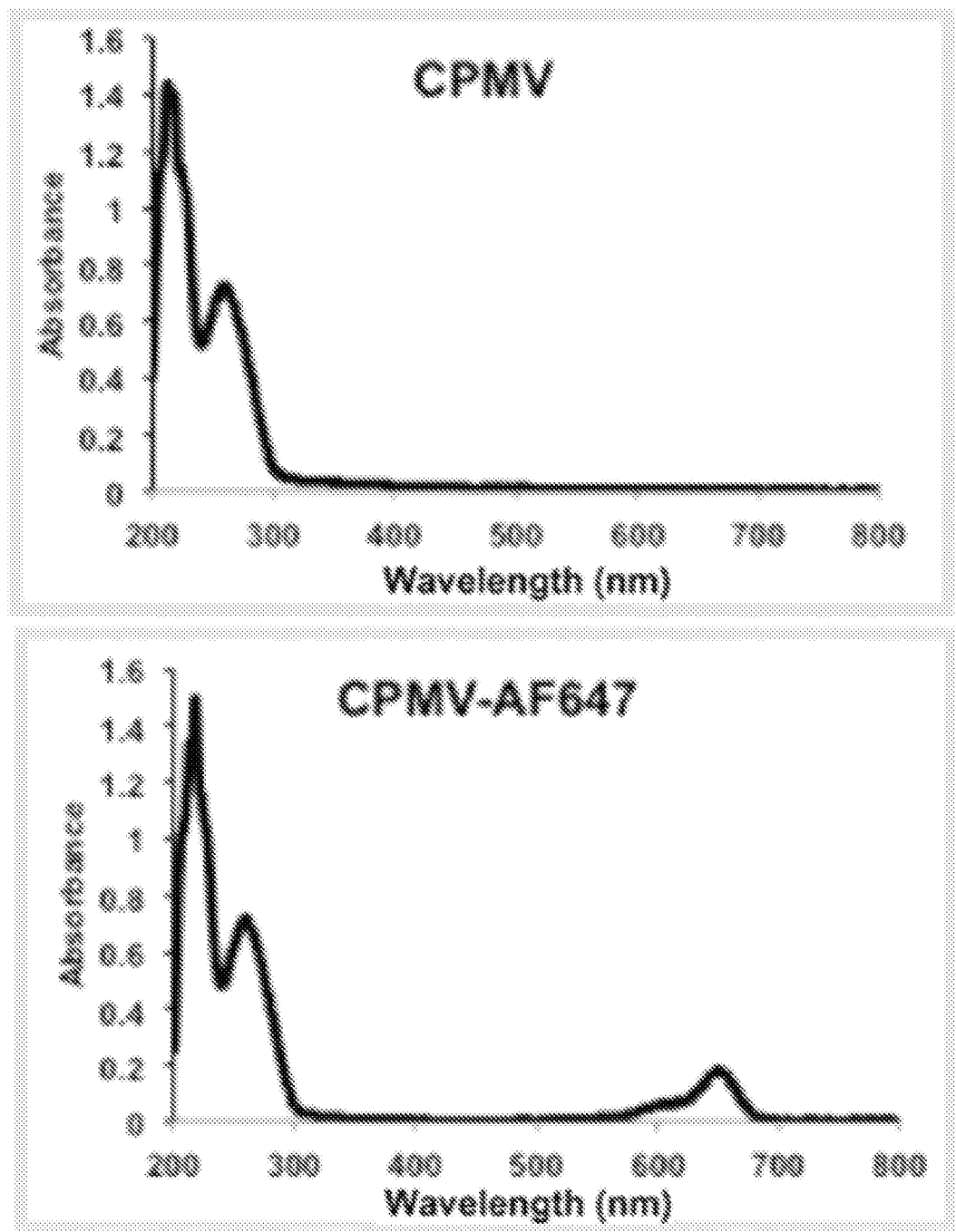
Figure 21B:
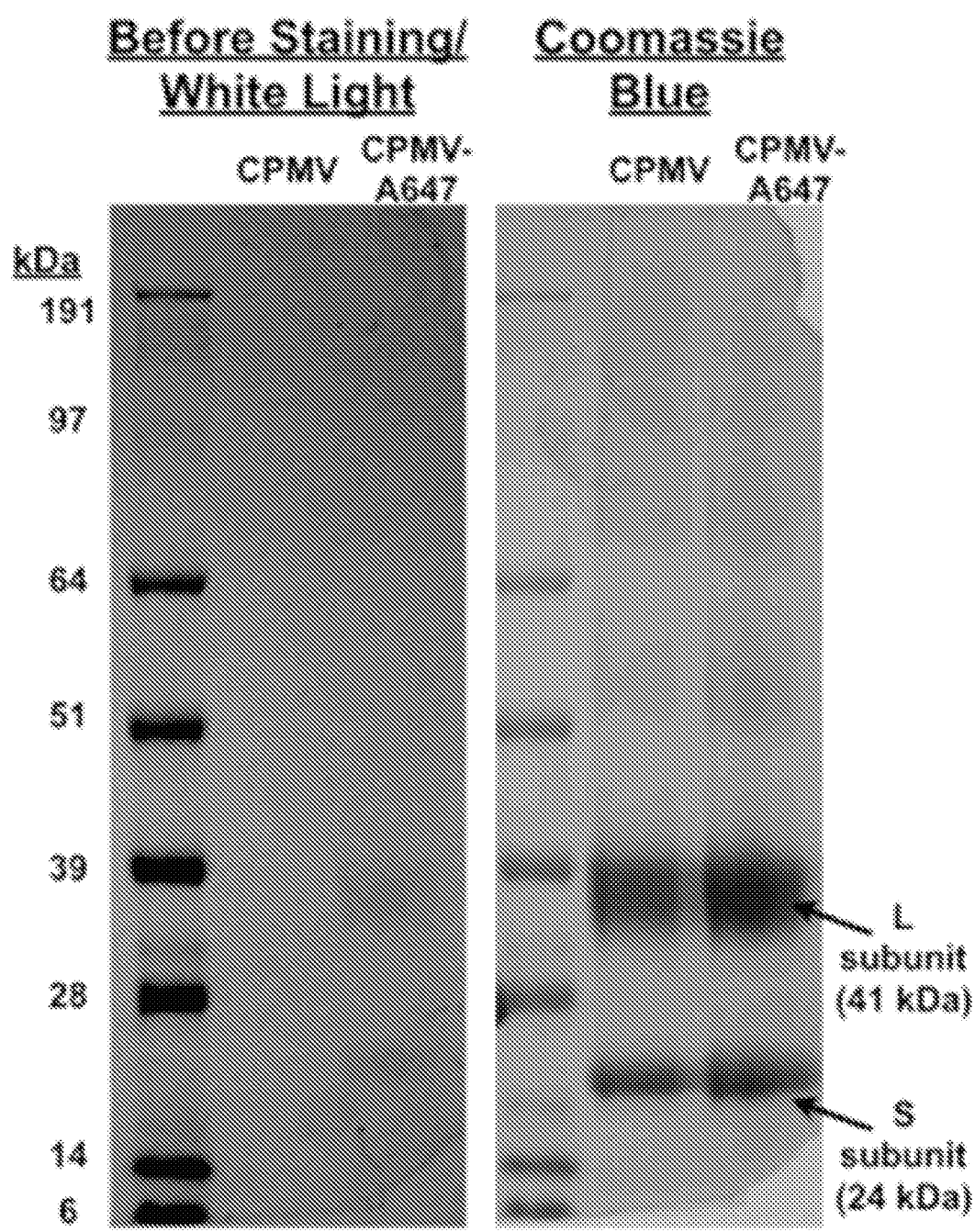

The biodistribution and clearance rate of CPMV compared to CPMV-G4 was evaluated using in vivo fluorescence imaging (Spectrum BLI). Mice without tumors were injected with 1 mg of CPMV labeled with AlexaFluor 647 either as free CPMV or formulated as the CPMV-G4 assembly as described above. CPMV nanoparticles were covalently functionalized with NHS-AF647 dye molecules using the exposed lysine residues on the capsid surface. The successful chemical labeling of the CPMV particles post purification was verified using UV-vis absorption spectroscopy; an average of 40 dye molecules per CPMV were attached (FIG. 21A). A sodium dodecyl sulfate (SDS) gel electrophoresis was also conducted to confirm the covalent conjugation of AF647 dye molecules to the CPMV coat proteins (FIG. 21B). Under white light, bright blue bands were observed matching the small and large subunit proteins of CPMV-AF647, which was not evident for CPMV; staining with Coomassie Blue, shows that CPMV coat proteins are colocalized with the dye. Successful assembly of fluorescent AF647-CPMV-G4 formulation was confirmed by immediate visual changes in the mixture as well as accumulation in the bottom of a centrifuge tube following a 30 s spin on a tabletop centrifuge (at 15 000 g) (FIG. 21C).

Figure 22A:
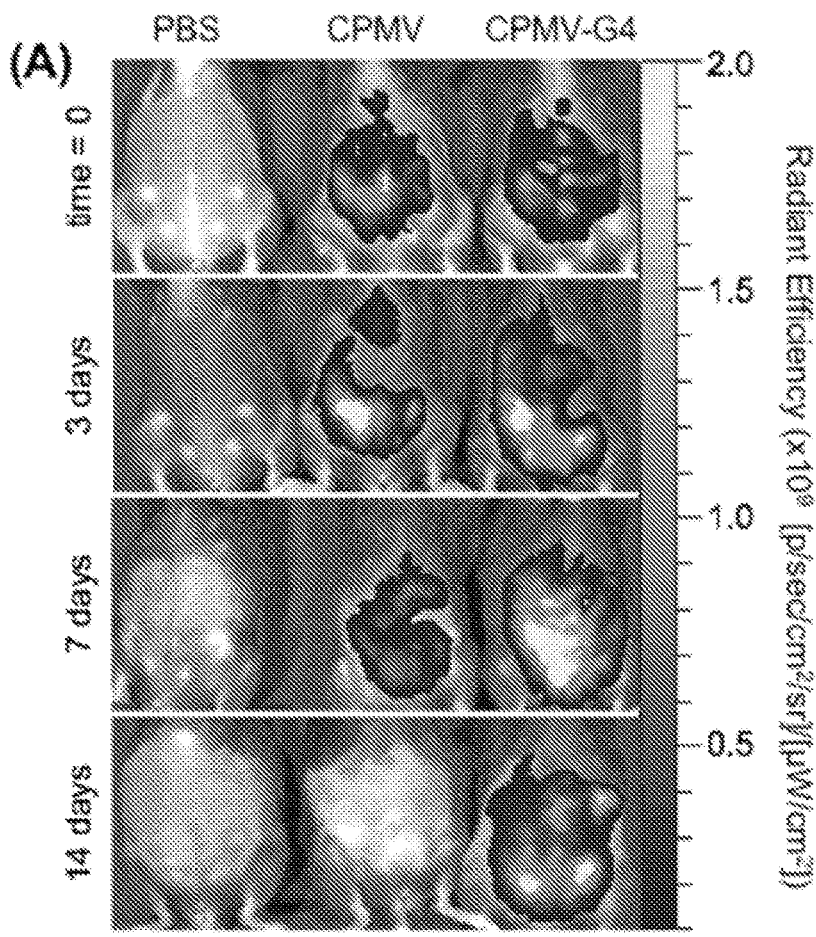
FIGS. 22A-B illustrate the retention of CPMV and CPMV-G4 in the intraperitoneal space. A) Fluorescence imaging of C57/BL6 mice immediately following injection, on days 3, 7, and 14. B) Normalized fluorescent intensity as determined by ROI analysis; the highest measured fluorescence intensity in the intraperitoneal space over the course of the study was established as 1 and relative intensity for all subsequent time-points was calculated as a portion of this intensity (n=3).
Figure 22B:
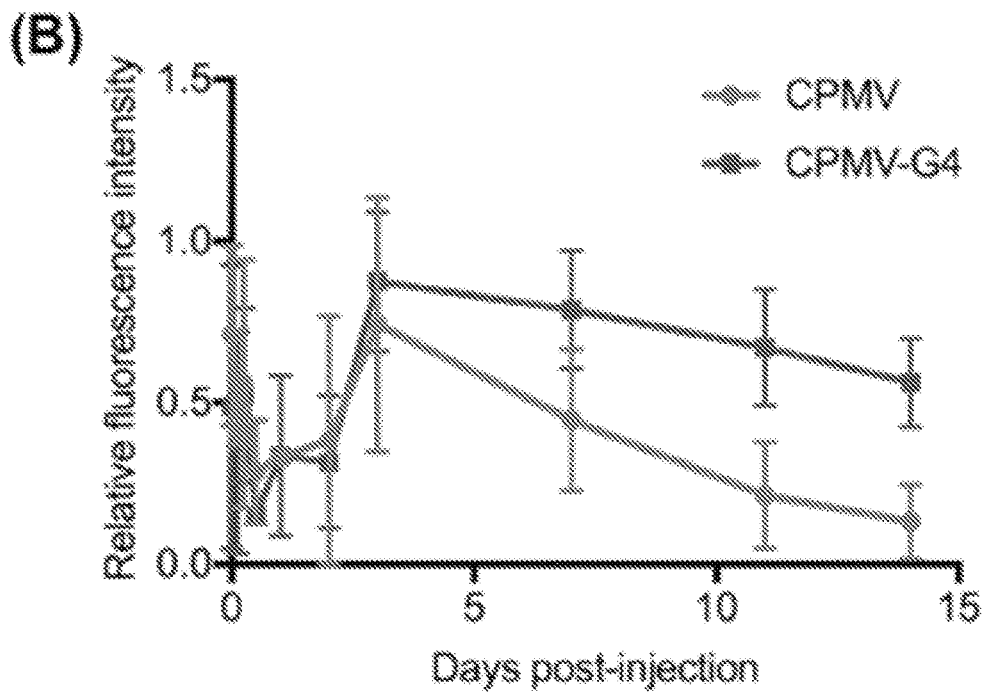

Biodistribution was then determined using a longitudinal imaging approach; at defined time points over a 14 d course, total fluorescence in the IP space was determined using Spec-trum BLI and region of interest (ROI) analysis (FIG. 22). Free CPMV was cleared from the IP space more quickly than CPMV-G4; ≈50% of the maximal measured fluorescence intensity was present for free CPMV at 7 d, in contrast over 50% of the maximal measured fluorescence intensity in CPMV-G4 treated animals persisted at day 14. Overall CPMV-G4 has roughly a 3 fold longer half-life in the peritoneum than free CPMV. Both groups showed an initial increase in measured fluorescent intensity, likely due to a reduction in the fluorescence quenching of the fluorophores; perhaps as the CPMV spread throughout the IP space, the overall concentration of fluorophores was reduced and measured fluorescence increased. To prevent this early quenching from causing artificially high percent retention to be calculated, relative fluorescence intensity was calculated from the maximum fluorescence measured and not the initial intensity measurement. While this quenching effect limits the utility of in vivo fluorescent imaging to determine the absolute concentration of CPMV still present in the IP space, it still provides useful information as to the relative speed at which free CPMV and CPMV-G4 assembly is cleared and supports enhanced retention of CPMV in the CPMV-G4 assembly com-pared to free CPMV.

These biodistribution studies are in good agreement with the efficacy studies that show a single administration of CPMV-G4 was as effective as weekly injections of free CPMV (FIG. 20). This confluence of data supports the conclusion that CPMV, when formulated as CPMV-G4 assemblies, forms a depot and is detach-able over prolonged periods of time, continually stimulating anti-tumor immunity. For this depot strategy of in situ vaccination to be effective, the depots must be retained within the peritoneal site of ovarian cancer. We hypothesize that the larger CPMV-G4 aggregates are not easily cleared through leaking into blood vessels or lymphatic drainage in the IP space without disassembly.

Compared to other systems, the observed retention time for CPMV-G4 is longer; for example polymer-based hydrogels injected intraperitoneally were found to persist at 8 d following injection. Further, while hyaluronic acid based hydrogels have been shown to persist in the IP space for a com-parable or longer time, their use as a drug carrier has led to both decreased and increased tumor growth, indicating that further investigation of this system, especially its degradation byproducts, is needed before it can be considered for use in slow-release formulations. Finally, our system has several advantages over other types of slow-release formulations including implantable devices that typically require an invasive surgery; the virus-dendrimer colloidal solution is nonviscous and can be administered with a syringe without surgical intervention. As with any nanotechnology, the advantages and disadvantages must be carefully considered; unlike plant-virus based materials, PAMAM dendrimers have been shown to be toxic at high concentrations and further study of the in vivo properties of dendrimers and associated hybrid materials is still needed in order to better understand associated toxicity and interaction with the immune system. Future studies may explore the assembly with other polymeric systems.

Virus-dendrimer hybrid materials are a novel class of materials with a number of potential applications targeting materials and human health. Here we present the application of the CPMV-G4 hybrid assembly as an immunotherapy; specifically the assembly functions as a depot with slow release of the immunostimulatory nanoparticle CPMV in the IP cavity, therefore prolonging its therapeutic antitumor effect in a mouse model of IP disseminated ovarian cancer. A single administration of the CPMV-G4 hybrid resulted in matched efficacy compared to weekly treatment using the soluble CPMV formulation. This is an important finding and may enable the in situ vaccine application of CPMV assemblies for difficult to inject tumors, such as ovarian cancer or gliomas; in these disease settings reducing the number of necessary administrations while maintaining a potent immunotherapy effect is an important goal to enable successful translation of in situ applied (immune)therapeutics.

Example 6

Our group has developed an in situ vaccination approach using virus-like nanoparticles derived from the plant virus cowpea mosaic virus (CPMV). In previous work, we demonstrated efficacy across various mouse tumor models; our data indicate that the plant viral in situ vaccine acts in part to activate intratumoral neutrophils which in turn lead to immune-mediated, systemic and memory responses against tumors, including melanoma, colon cancer, breast cancer, and ovarian cancer. Specifically, weekly intraperitoneal (IP) treatment with CPMV has been shown to significantly improve survival after IP tumor challenge with a hyperaggressive clone of ID8 epithelial mouse ovarian cancer cells compared to phosphate-buffered saline (PBS)-treated controls.

Nevertheless, although these studies highlight the potential of plant viral nanoparticles as in situ vaccines, immunotherapy as monotherapy is generally effective only against small tumors, and most patients do not respond to single-approach immunotherapy. Combining multiple treatment regimes, however, could form the basis for success. Therefore, in the present work, we examined the combination of CPMV in situ vaccination with radiation therapy (RT). We hypothesized that the combination of RT with our CPMV in situ vaccine would enhance the antitumor effect. Specifically, the hypothesis is that RT would debulk the tumor to provide a burst of tumor antigens in the context of immunogenic cell death that fosters specific immune recognition and response to those antigens; in turn, CPMV-mediated immune stimulation would further augment antitumor immunity to protect from outgrowth of metastases and recurrence of the disease. Here, we report a test of this hypothesis using a mouse model of serous ovarian cancer.

Experimental Section
Preparation of CPMV Nanoparticles

CPMV was propagated in black-eyed pea plants (*Vigna unguiculata*) and isolated using previously reported protocols.

Cells

The highly aggressive murine ovarian cancer cell line ID8-Defb29/Vegf-A was maintained in RPMI 1640 medium supplemented with 10% (v/v) heat-inactivated fetal bovine serum, 2 mM L-glutamine, 1 mM sodium pyruvate, 0.05 mM 2-mercaptoethanol, and 100 U penicillin/streptomycin. The cells were stably transfected with luciferase to enable in vivo tracking. Luciferase was expressed using vesicular stomatitis virus-glycoprotein (VSVG) retroviral transduction of pBabe, and luciferase-expressing cells were selected with puromycin. In brief, plasmids VSVG and pBabe-puro-Luc (10 µg each) were added to GP2-293 packaging cells at 40% confluency in a 75 cm2 flask (maintained in 7 mL of complete Dulbecco's modified Eagle's medium) following a 30 min incubation with 60 µL of TransIT (Mirus). GP2-293 cells and plasmids were a generous gift from Dr. William Schiemann, Case Western Reserve University. Following a 48 h incubation, the medium was collected, filtered to remove cellular debris, and added to ID8-Defb29/Vegf cells in the presence of polybrene (8 µg/mL, Santa Cruz Biotechnology (SCBT)) in a ratio of 50:50 with modified RPMI 1640 medium typically used with this cell line. ID8-Defb29/Vegf cells were incubated with retroviral particles for 24 h and allowed to recover in fresh medium for an additional 24 h; cells expressing the plasmid were selected with puromycin for 5 days (5 µg/mL medium, SCBT). Expression of luciferase was confirmed by IVIS Spectrum BLI (PerkinElmer) imaging of cells in a 96-well plate in the presence of 15 µg of luciferin/well. Measured luminescence was found to be linearly correlated with cell number in the range of 5000-500 000 cells per well. The resultant cell line is referred to as ID8-Defb29/Vegf-A-Luc.

Tumor Model

Animal studies were carried out using IACUC-approved protocols. Female C57BL/6 mice were obtained from Jackson Labs and used in these experiments at 8-10 weeks of age. Mice were shaved, and 5 million ID8-Defb29/Vegf-A-Luc cells in a 50:50 mixture of PBS cell suspension and matrigel were injected subcutaneously in the right flank. Once tumors were approximately 100-150 mm3, mice were randomized into four treatment groups (n=4): radiation (RT) alone, RT+CPMV, CPMV alone, and PBS placebo injections. RT was delivered on day 0 via a Cs-137 irradiator (Shepard Mark I; dose rate ~2.75 Gy/min) to a total dose of 10 Gy with a source aligned with the tumor and the rest of the animal shielded with lead blocks. On day 1 and then once weekly for a total of five treatments, 100 µg of CPMV in x µL of PBS or the same volume of PBS were injected intratumorally. Tumor growth was monitored using caliper measurements as well as by luminescence imaging of the luciferase-expressing cancer cells. For the latter, mice were injected intraperitoneally with luciferin (15 mg/mL, 150 µL) and imaged 5 min post-injection with a 3 min exposure time using a PerkinElmer IVIS Spectrum in vivo imaging system. Total luminescence was determined using Living Image software, and total counts per mouse were graphed.

Immunohistochemistry

Primary antibody for CD4 was purchased from TONBO Biosciences, purified antimouse CD4 (clone GK1.5) and CD8 from eBioscience, and purified antimouse CD8a (clone 53-6.7). IHC was performed on tumor sections from the mice of each treatment group to characterize and quantify tumor immune cell infiltrate on day 1 and 10, following the initiation of treatment using a previously established protocol. Briefly, tumors were surgically dissected and immediately cryopreserved in optimal cutting temperature compound. Tissue sections were microsectioned and plated on slides. Frozen sections on slides were fixed with acetone and washed with PBS, and then antigen blocking was performed with 5% (v/v) rabbit serum. Next, primary antibodies were added to coat the tissue sample and allowed to incubate at 4° C. overnight. Slides were then washed with PBS and stained with immPRESS HRP anti-rat IgG peroxidase polymer detection kit (Vector Laboratories) and 3,3'-diaminobenzidine tetrahydrochloride solution. Sections were also stained with hematoxylin and washed with PBS, dehydrated with ethanol, cleaned with xylene, and finally permanently mounted. Slides were imaged using a Zeiss Axio Imager.Z1 inverted high-resolution microscope with motorized stage.

Results

Tumor Growth Delay. Subcutaneous ID8-Defb29/Vegf-A-Luc tumors in C57BL/6 female mice were treated with RT, in situ vaccine (CPMV), both RT+CPMV, or PBS (placebo group); treatment was begun when tumors reached a volume of 100-150 mm³. RT (10 Gy) was given in a single session on day 0, whereas the CPMV treatment was repeated 5 times in weekly intervals starting on day 1 (FIG. 23A). As evidenced by tumor volume measurements, the tumor growth was delayed after day 5 in both RT arms compared to the arms receiving CPMV alone or PBS ($p<0.05$) (FIG. 24B). From day 18 post-RT through the end of the study, the combination of RT+CPMV produced significantly greater tumor growth delay than did RT alone ($p<0.05$). Tumor volumes of animals treated with RT+CPMV combination were on average 2-3× smaller than those measured for animals receiving the RT alone; and this difference was apparent 14 days post-treatment (FIG. 23B).

Tumor growth as assessed by bioluminescence showed similar results, with the RT and RT+CPMV arms having significantly reduced ($p<0.05$) tumor burden compared to the arms receiving CPMV alone or PBS (FIG. 23C). There was also a trend toward a reduction in the luminescence counts in the combination RT+CPMV arm compared to the RT alone arm ($p=0.06$). Although we previously observed a potent efficacy of CPMV in situ as solo therapy in early-stage IP disseminated ID8-Defb29/Vegf-A in C57BL/6 mice, in the present study, we did not observe the same efficacy using the same dose of CPMV administered directly into the subcutaneous tumors.

Tumor Immune Cell Infiltration

Figure 24:
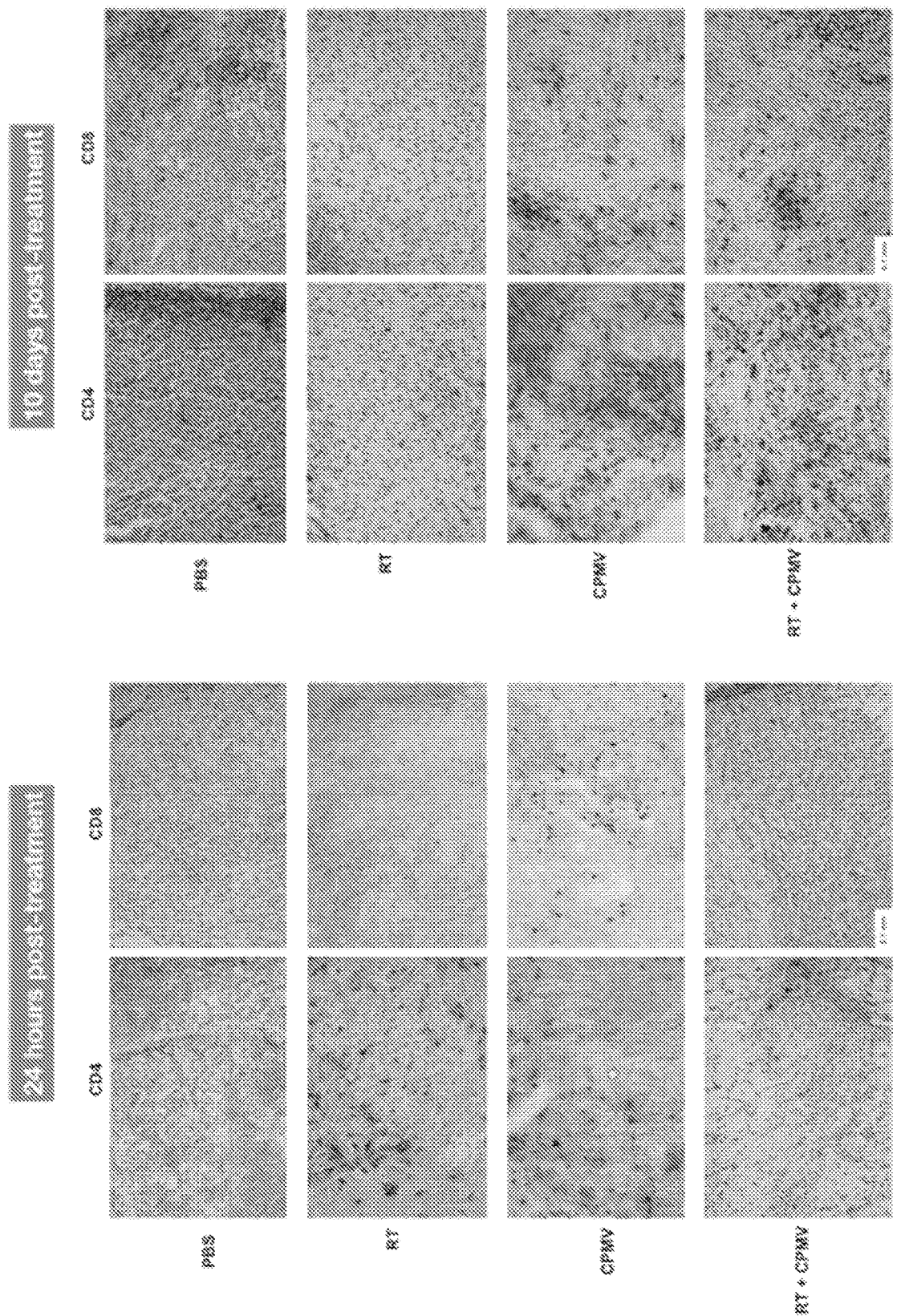
FIG. 24 illustrates tumor sections stained for CD4 and CD8 lymphocytes on day 2 and 11 corresponding to 24 h and 10 days post CPMV or PBS placebo treatment.

Tumor immune cell infiltration was determined by immunohistochemistry (IHC) on samples of tumors recovered on day 2 and 11, following treatment with RT, CPMV, RT+CPMV, or PBS (FIG. 24). Early-stage PBS-treated tumors (volumes of 100-150 mm3) did not reveal significant levels of CD4- or CD8-positive cells. By day 11, the untreated later-stage tumors (volumes of ~500 mm³) showed some degree of CD4- or CD8-positive cells; however, compared to other treatment groups, this level of T cell infiltration was minimal. By day 2, 24 h after the start of CPMV treatment, a modest CD4-positive infiltrate was seen in tumors treated with RT or CPMV alone or in combination, with no significant CD8-positive effector immune cell infiltrate in any group at that time. In contrast, 10 days following initiation of CPMV treatment, both the CPMV alone group and the RT+CPMV group showed significant infiltration of CD8-positive effector immune cells, in addition to the CD4-positive immune infiltrate. The lymphocyte infiltration was observed only in groups exposed to CPMV or RT+CPMV and not in those given RT alone or PBS. While quantitative studies were not carried out, there appears to be a trend toward a greater lymphocyte infiltration into RT+CPMV-treated tumors than into tumors treated with CPMV alone (FIG. 24).

Ovarian cancer remains difficult to treat and a deadly malignancy even with the advent of new therapeutic approaches and novel drug agents. Therefore, the initial promise of newer immunotherapy paradigms is of significant interest. In our study, we examined a novel immunotherapeutic viral nanoparticle, CPMV, which has previously been shown to be an effective in situ vaccination strategy in a syngeneic mouse ID8 ovarian cancer model. Although we previously observed high potency of the CPMV in situ vaccine in early-stage metastatic disseminated disease, the CPMV monotherapy had no apparent effect on the growth of subcutaneous tumors derived from the same cell line (ID8-Defb29/Vegf-A) (FIG. 23). This difference may be explained by the fact that in our previous study early-stage disease was treated, that is, the CPMV in situ vaccine was given as early as 3 days post-IP ID8-Defb29/Vegf-A cell injection. In contrast, in the present study, mice were treated ~10-14 days post-ID8-Defb29/Vegf-A cell injection when subcutaneous tumors reached a volume of 100-150 mm³. Differences in tumor burden at the time of treatment and the different anatomical locations may both explain the difference in response to CPMV monotherapy.

Another difference between our earlier work and the present study is the fact that we used a nucleic-acid-free, viruslike particle of CPMV, termed "empty" CPMV (eCPMV), for the treatment of early-stage, IP tumors, whereas the present study used nucleic-acid-containing CPMV particles to treat later-stage subcutaneous tumors. CPMV contains a bipartite RNA genome, with RNA-1 and RNA-2 encapsulated separately into virions of identical protein composition. The RNA cargo may affect the type of immune response induced; RNA is an immune-stimulatory danger-associated molecular pattern known to stimulate innate immune responses through Tolllike receptor signaling. Although others reported the encapsulated RNA in the plant viruslike nanoparticle derived from papaya mosaic virus to be beneficial in triggering an antitumor immune response, the underlying mechanism of immune stimulation comparing different plant virus-based nanoparticles of different geometry and molecular composition remains to be elucidated. It cannot be ruled out that RNAcontaining CPMV and nucleic-acid-free eCPMV have distinct potencies based on differences in immune activation. Our laboratory is investigating this question, but this is beyond the present study.

Nevertheless, even though the potency of CPMV monotherapy was less profound than in our previous animal model treated with eCPMV, luminescence measurements indicated reduced disease burden for CPMV versus PBS control groups at the conclusion of the study (FIG. 23C). The reduced disease burden at the endpoint and the observation of immune cell infiltration into the tumor tissue upon CPMV in situ vaccination indicate that animals with the subcutaneous ID8 tumors indeed responded to the treatment, although dosing may be suboptimal. It is clear that dosing and administration schedules need to be optimized for each disease model; however, this was beyond the scope of the present study. In fact, the suboptimal dosing was advantageous to allow testing of RT+CPMV combination therapy. ID8 ovarian tumors are known to be radiosensitive; thus, it was expected that RT alone would produce a tumor growth delay. Nevertheless, the combination treatment, RT+CPMV in situ vaccine, resulted in significantly reduced tumor growth compared to RT or CPMV treatment alone. These findings were also confirmed by our bioluminescence studies (FIG. 23B,C).

There are several mechanisms by which RT can improve the efficacy of immunotherapeutic agents, including inducing immunogenic cell death, enhancing release of neoantigens, altering the tumor cell phenotype, and stimulating the immune system via the STING pathway and IFN signaling. The mechanism of cell death traditionally attributed to radiation is the mitotic catastrophe or p53-mediated intrinsic pathway apoptosis. However, radiation can also upregulate CD95/Fas, tumor necrosis factor (TNF)-related apoptosis-inducing ligand, and TNF alpha death receptor pathways involved in the extrinsic pathway of apoptosis. Upregulation of CD95/Fas on tumor cells has been shown to improve tumor cell kill by CD8+ T lymphocytes. In addition to enhancing immune-mediated cell death, radiation has also been shown to alter tumor cell phenotype. Tumor cells often downregulate major histocompatibility complex I (MHC-I) to evade the immune system. However, radiation exposure can also elicit a TNF and IFN response that results in MHC-I upregulation on tumor cells, as well as increased ICAM-1 expression, to improve the binding and interaction of T cells with MHC-I in multiple patient-derived human EOC cell lines. Moreover, tumor cells exposed to radiation have been shown to have a greater diversity of antigens presented on their surface MHC-I molecules. Finally, radiation itself can induce an inflammatory response via the Cgas/STING pathway either via cytosolic DNA or via DNA double-strand breaks within micronuclei. Although activation of this pathway may initially lead to a cytotoxic T-cell-mediated anti-tumor response, IFN-mediated immune-suppressive pathways are also activated with recruitment of myeloid-derived suppressor cells, regulatory T cells ($T_{regs}$), and induction of tumor cell PDL1 expression.

In contrast to RT, which has been exhaustively studied, CPMV is a novel immunotherapeutic agent and to date, we have limited data surrounding its mechanism of immune activation. Our IHC results demonstrate that CPMV with or without RT can increase both CD4+ and CD8+ tumorinfiltrating lymphocytes. In our study, we targeted relatively "cold", well-established tumors; although CPMV monotherapy did not show apparent efficacy over placebo-treated control groups, IHC data indicate that CPMV alone recruits large numbers of T cells, particularly CD4+ T cells. Although CPMV clearly initiates an immune response, the inflammatory response that it generates in this model likely recruits both effector and immunosuppressive cells. It is possible that a significant number of recruited CD4+ T cells are CD4+ T regulatory cells that are strongly immunosuppressive through multiple mechanisms. If this is the case, it likely explains why CPMV alone had minimal effect on tumor growth in this model, in that both effector and suppressive T cells are being recruited, and the regulatory T cells can limit effector T cell antitumor responses. Exposure to RT prior to CPMV in situ vaccination may help shift the balance toward a more cytotoxic immune response. Detailed time-dependent phenotyping of recruited T cells would better elaborate how and when the T cell subsets are recruited to these tumors in response to various treatments. An alternative possibility that was not explored is that the innate cell responses which can also be immunosuppressive or immunostimulatory were tilted toward immunosuppressive with CPMV alone but were altered toward immunostimulation in combination with RT.

Although our results demonstrated significantly improved tumor growth delay, as measured both by tumor volume and by bioluminescence, we were unable to achieve complete tumor regression, even in the RT+CPMV arm. Future optimization of dosing and administration schedule is expected to further increase efficacy. Another possible approach to improve our treatment paradigm would be to add a checkpoint inhibitor to eradicate suppressive regulatory T cells prior to priming with RT and initiating an effector immune response with CPMV. Anti-CTLA4 treatments have previously been shown to eradicate regulatory T cells and help illicit a robust immune response in syngeneic mouse breast cancer models. Therefore, anti-CTLA4 checkpoint blockade may also eradicate suppressive regulatory T cells in our ovarian cancer model and hence remove suppressive immune cell barriers prior to RT and CPMV. Furthermore, the checkpoint blockade has been shown to synergize with viral immunotherapy. It is thought that the viral in situ vaccination approach augments other immunotherapies by expanding antigen-specific T cells.

We have demonstrated the potent efficacy of RT+CPMV in a mouse model of serous ovarian cancer. Data indicate that the combination of RT+CPMV enhances efficacy over RT alone, and that this may be attributed to expansion of T cells within the tumors. Although it is clear that more studies are needed on the mechanism(s) of immune activation by CPMV and other viral nanotechnologies, our data indicate this to be a promising immunotherapy. In situ vaccination with plant-derived viral nanotechnologies has advantages over mammalian vectors or systemically administered checkpoint blockade: plant virus based nanotechnologies are not infectious toward mammals; the localized treatment is safer than systemic administration of immunotherapeutic reagents; and there is no requirement to identify antigens in the tumor or relate those antigens to the patient's human leukocyte antigen. The combination of the viral in situ vaccine with RT may be a particularly powerful strategy because RT debulks tumors, providing a burst of tumor antigens in the context of immunogenic cell death, therefore, synergizing with the CPMV in situ immune stimulation that further augments antitumor immunity.

Example 7

Immunotherapy to treat cancer is being aggressively developed and clinically utilized. With respect to immunotherapy and radiation treatment, new research studies are beginning to confirm what has long been theorized, that local radiation treatment has a very important immune component that can be enhanced by appropriate RT dose delivery and the addition of compatible immune stimulants. In previous studies, we have shown that moderate magnetic nanoparticle hyperthermia (mNPH) treatment of an established murine melanoma tumor can generate immune-based systemic resistance to tumor rechallenge in a contralateral tumor in the same mouse.

Radiation is a well-established local cancer therapy that rarely demonstrates the ability to affect unirradiated metastatic tumors distant from the primary tumor treatment site. This uncommon and unpredictable effect on untreated tumors is termed the "abscopal effect", and while it is accepted to be immune-based, the pathophysiologic mechanisms are not well-defined. This immune basis of the abscopal effect got initial support from mouse studies performed more than 39 years ago demonstrating the contribution of T cells to radiation-induced tumor control. Recent clinical studies have begun to show that radiation and immunotherapy treatments such as checkpoint inhibitors are capable of generating a quantifiable positive response in unirradiated tumors. Another recent radiationabscopal effect study of more that 6000 men with metastatic prostate carcinoma, treated with local prostate RT+androgen deprivation therapy, demonstrated significant improvement in the overall survival rate, as compared to androgen deprivation therapy alone. This study shows that the treatment of a primary prostate tumor with RT can improve the outcome for patients with metastatic disease. Other important factors when assessing the immune effects of RT are radiation fraction number and size. Recent studies indicate that a single radiation dose compared to multiple smaller radiation doses, at the same effective total dose, induces markedly different gene and protein expression profiles. Many believe that delivering RT with larger but fewer doses/fractions (hypofractionated RT, HFRT), while potentially more damaging to normal tissue, might be more immunogenic and therapeutically effective. The basic concept of the impact of RT on the antitumor immune response is that RT damages the tumor and/or microenvironment to create a more immunogenic local environment.

RT by itself is rarely sufficient to create clinically effective antitumor immunity. Rather, the common local response to RT is thought to be immunosuppressive. Studies suggest the RT damage generally recruits M2-type tissue repair macrophages that suppress adaptive immunity. The crucial aspect appears to be the potential of RT to generate an "immunogenic cell death" (ICD) or sublethal injury that occurs when cells die or are altered in a manner that stimulates an immune response. ICD is characterized by a grouping of dangerassociated molecular signals (DAMPs), among which are calreticulin expression on the cell surface, release of ATP, release of HMGB1 protein, and expression of type one interferons. When the tumor environment is sufficiently immunogenic, tumor-associated antigens and neoantigens are taken up by antigen presenting cells that go to the lymph nodes, present these antigens to T cells, and stimulate an adaptive immune response against tumor cells. This adaptive immune response not only impacts local tumors but can also generate a systemic response against the same tumor in unirradiated sites. Recent studies using T-cell receptor (TCR) transgenic mice have shown that radiation can prime T cells to interact with exogenous tumor antigens and that radiation can induce a tumor specific T cell response and subsequent immunogenic cell death.

In vivo murine tumor studies have demonstrated the safety, efficacy, and abscopal-type effects of both mNPH and VLP. Additional studies have demonstrated the improved tumor treatment efficacy when combining mNPH with radiation. We have used this information to assess the feasibility and efficacy of two different nanotechnology-based immune adjuvants (mNPH and VLP) combined with hypofractionated RT in a spontaneous canine oral melanoma model. Our rationale is that the nanoparticle immune adjuvants will combine with RT-induced ICD to expand the tumor specific effector T cell population resulting in longer local and distant tumor remission.

Dogs are genetically variable animals with a cancer incidence and prevalence, tumor type, and tissue origin site that is comparable to human cancer. Behaviorally, the canine oral melanoma is very similar to an aggressive human dermal melanoma. Canine oral melanomas grow at rates roughly similar to aggressive human melanoma, metastasize aggressively, and are often well-established when detected in the oral cavity. Most oral canine melanomas are treated with excisional surgery with completeness of tumor removal status unknown at the time of surgery. Approximately 85-90% of these tumors recur locally and/or at distant site within 5-9 months. RT alone, using varied total dose and fraction delivery regimens, has demonstrated a similar prognosis, with a median recurrence/metastasis time of 5-7 months. Variables such as age, tumor size, and tumor location influence the prognosis; however, most studies suggest that these influences do not alter the time to recurrence or metastasis more than 20% for any situation.

Methods

Canine Oral Melanoma Patient Recruitment and Experimental Treatment

The canine oral melanoma cancer patients were recruited from local veterinary practices. Study inclusion required a tissue biopsy diagnosis of oral malignant melanoma, a tumor less than 5 cm in diameter, the lack of both metastatic disease (clinical examination/CT scan) and chroniclife threatening disease, and legally documented owner consent. All diagnostic examinations and clinical treatments were performed at Geisel School of Medicine, Dartmouth Hitchcock Medical Center, Lebanon, N.H. Referring veterinarians remained part of the clinical team, receiving all relevant patient treatment and health information from the Dartmouth team. When appropriate, the referral veterinarians performed follow up examinations and supportive treatments.

Radiation Treatment Planning and Delivery

Following generation of a CT-based 3-D radiation treatment plan, all patients received 6 doses of 6 Gy photon radiation (36 Gy total, Varian 2100C linear accelerator) to the local tumor and 1 cm peri-tumor margin. Treatment was applied on a Monday, Wednesday, Friday schedule over a 2 week period. All treatments were performed under general anesthesia.

Magnetic Iron Oxide Nanoparticle (IONP) Hyperthermia Treatment (mNPH)

NT-01 iron oxide nanoparticles (Micromod Partikeltechnologie GmBH, Rostock, Germany) were used. NT-01 magnetic nanoparticles consist of multiple ~20 nm hematite crystals embedded in a dextran matrix core (40 nm diameter), surrounded by a dextran shell. The final average hydrodynamic NP diameter was 110 nm. The mNP were delivered in a sterile water-based NP concentration of 44 mg/mL with an iron concentration of 28 mg/mL and a volume of 500 µL. The amount of iron oxide nanoparticles was constant regardless of tumor size. A cooled Fluxtrol pancake coil (20 cm diameter) or a cooled custom copper helical coil, with an inner diameter of 20 cm, was used to generate AMF. The AMF coils were powered by a variable 25 KW generator (Huttinger Elektronik GmbH, Freiburg, Germany) at a field of 150 kHz and 400 Oe. The AMF coil and generator were cooled by a chiller (Tek-Temp Instruments, Croydon, Pa.) operating at 20° C. and 4 gallons per minute. mNPs were delivered intratumorally at a dose of 7.5 mg into 4 equally spaced tumor sites. mNP were incubated for 90 min prior to AMF exposure. Tumors were treated to a thermal dose equivalent to 43° C. for 60 min (cumulative equivalent minutes/CEM=60). Each tumor receiving mNPH was treated twice (once each week) over the 2 week treatment period. Temperatures were measured using 0.3 mm fiberoptic sensors (FISO Corp, Quebec, Canada) accurate to 0.1° C. placed in 3 tumor sites, 2 peri-tumor sites, and 1 core/rectum site.

Plant Virus-Like Nanoparticles (VLP)

VLPs from cowpea mosaic virus were produced in plants. VLPs were delivered intratumorally 2 times/week×2 weeks (four treatments). Each 200 µg (200 µL) intratumoral VLP injection was distributed in 3 locations within the tumor. The amount of VLPs per treatment was constant regardless of the tumor size.

Treatments and End Points

Using a feasibility study design, five tumors were treated with four treatment regimens:
 (a) Hypofractionated radiation therapy (HFRT) @ 36 Gy (6×6 Gy). n=1,
 (b) Magnetic/iron oxide nanoparticle hyperthermia (mNPH) @ 2×CEM 60. n=1
 (c) HFRT+virus-like nanoparticles (VLP) @ 4×200 µg. N=2
 (d) HFRT+VLP+mNPH. n=1

Clinical end points included time to recurrence or metastasis and survival. Primary tumor response and potential metastasis was assessed clinically every 2 weeks for 3 months posttreatment and every 2-3 months thereafter, including a radiological exam (X-ray, CT). The immunopathology end point was histomorphological quantification of the cell/tissue composition of the tumor. Samples were assessed before and 14-21 days post-treatment.

Quantification of Tumor Cellularity Following RT, mNPH and/or VLP

To assess the immune response, quantification of the inflammatory/immune cell infiltration into the tumor and the peri-tumoral region was performed in tissues taken before treatment and 14-21 days following treatment completion. We used the well-established Chalkley histomorphometric technique to quantitate cell types in standard histology images. This method, using conventional hematoxylin and eosin (H&E) stained slides, consists of placing a 100-point optical grid over randomly determined microscopic fields (we used 10 fields). At each cross-hair grid point, the cell or tissue type is identified by its morphology and recorded, providing a relative cell/tissue composition of the sample being assessed. We assessed four different cell/tissue parameters: (a) tumor cell, (b) mononuclear immune cell (lymphocyte/monocyte/macrophage), (c) polymorphonuclear cells (PMN, neutrophils), and stroma (fibrous connective tissues, vascular tissue, etc.). Hematoxylin and eosin stain is a routine histochemical dye-type stain that is commonly used to assess morphological cell and tissue detail. H&E stain does not involve an antibody and is not capable of tagging/staining a specific molecule or protein. Rather, the eosin (pink color) is an acidic dye that stains almost all cellular proteins, and the hematoxylin (blue color) is basophillic dye that stains nucleic acid (nucleus/DNA).

Results

Figure 25:
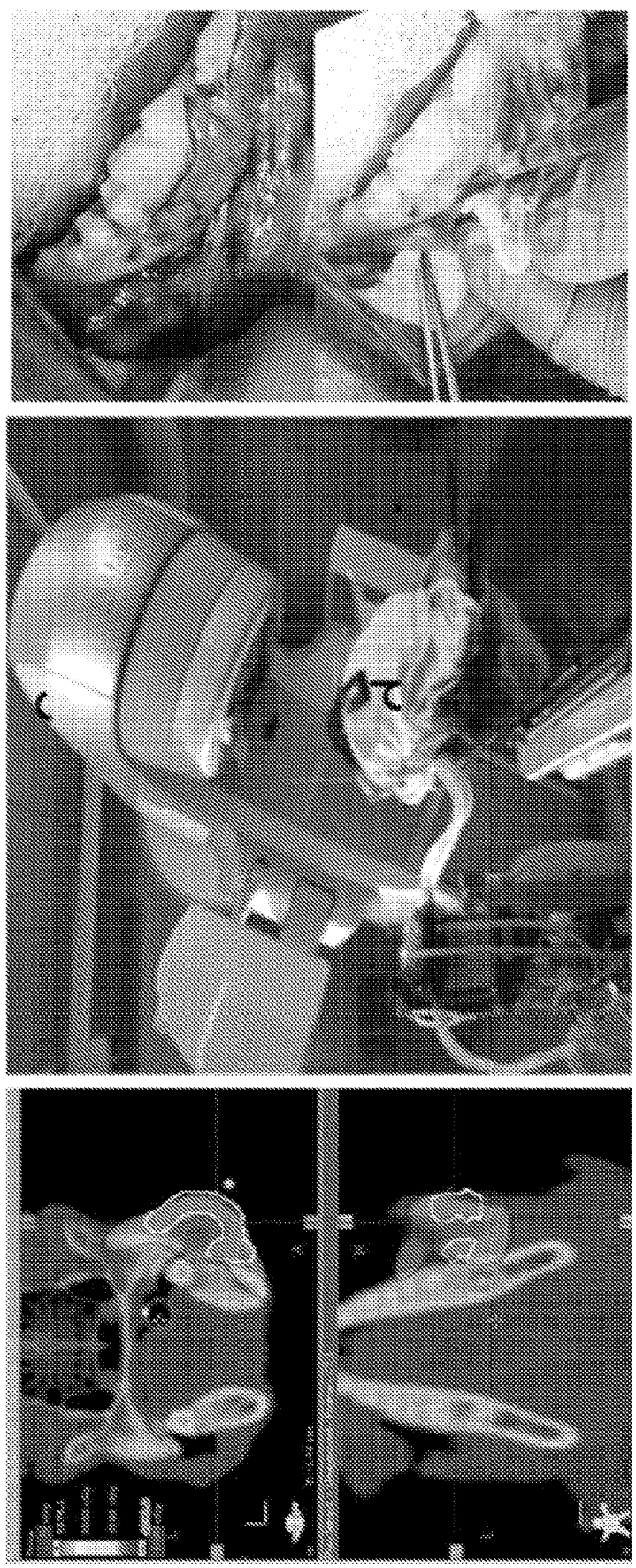
FIG. 25 illustrates the treatment of 9 year old Rottweiler with left mandibular oral melanoma. The tumor received 6×6 Gy radiation, mNPH, and 4×200 μg of VLP. Left figures demonstrate the 3-D radiation treatment plan. Center figure shows patient in position for radiation delivery via the Varian Truebeam linear accelerator. Right figures show intratumoral injection of VLP.

This example reports results from RT combined with nanotechnology-based in situ vaccination in canine oral melanoma. The application of radiation utilized clinical equipment and CT-based 3-D treatment planning similar to what is done for human patients. Study results, using quantitative tumor composition histomorphometry, demonstrate the effects of combining hypofractionated RT with mNPH and/or VLP (FIG. 25, Table 3). Histomorphometric quantification of the cellular composition of the melanoma tumors before and 14-21 days after treatment was used to document cellular immunopathology changes. Time to tumor recurrence and/or metastasis demonstrate clinical treatment responses. The radiation treatment utilized clinical treatment planning as shown in FIG. 25, and radiation was applied using clinical treatment equipment. This enabled the control and precision of radiation dosimetry that is utilized clinically.

Tumor response data from five patients is summarized in Table 3. It is important to note that while we quantified the immune cell response in the tumor and peri-tumor normal tissue in all patients, peri-tumor normal tissue samples (biopsies) were more challenging to acquire and were not acquired from all patients. Therefore, although we give an example of the comparative tumor and peri-tumor normal tissue response in the FIG. 26 patient, the cell response quantification information demonstrated in Table 1 includes only pretreatment and post-treatment information for tumor tissues, not peri-tumor tissue.

Figure 26:
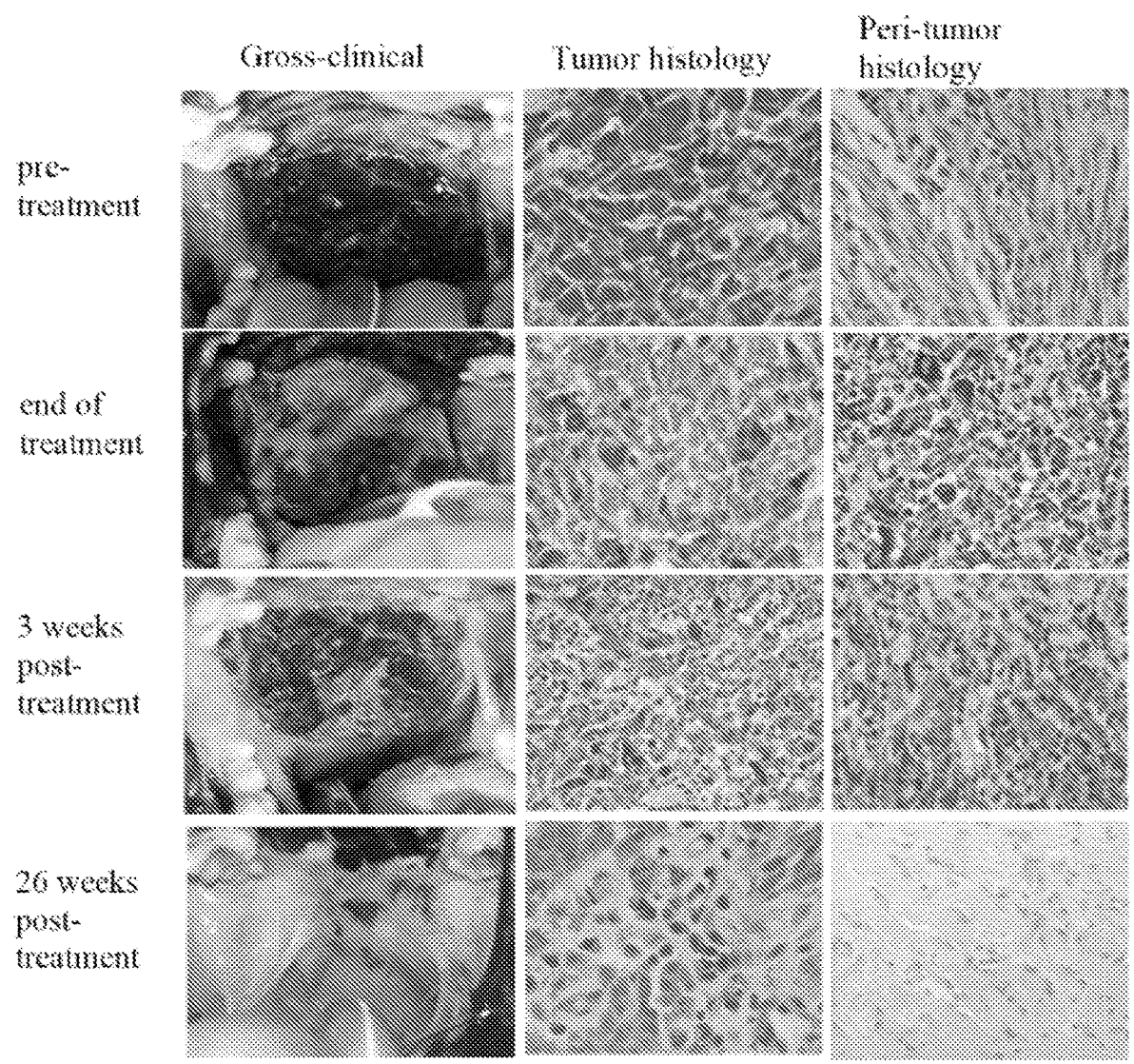
FIG. 26 illustrates tumor regression and cellular changes in a large soft palate oral melanoma following HFRT and VLP treatment. The images are from a 12-year old female beagle patient. In addition to complete tumor resolution, that is now durable at 20 months, there is a dramatic inflammatory/immune response in the weeks following treatment. The figure provides visual comparison of the gross clinical response, and the level of immune cell infiltration in the tumor and peri-tumor tissue at the selected times and illustrates sample histologic images used for quantitation of immune infiltrate in Table 1. The response is largely mononuclear cell (macrophage/lymphocyte, small blue cells with high nucleus/cytoplasm ratio); however, pockets of neutrophils are also seen in some areas. As noted in the final two histology photomicrographs, while there is no residual tumor, there is some ongoing active fibroplasia, however most of the response at this point is mature fibrosis.

Although the sample is small, the combination of HFRT+VLP appears to be the most promising treatment, since both patients fully resolved the treated tumor, neither patient relapsed, and one patient is clinically cancer free 20 months after treatment, which is well outside of the expected time to relapse of 5-9 months. The histology of multiple tumor and peri-tumor tissue samples at different time points from this patient is shown (FIG. 26, 12 month old female beagle). This oral melanoma case received 6×6 Gy HFRT (days 1, 3, 5, 7, 9, 12) and 4×200 µg VLP (days 2, 5, 7, 12) to treat an ~35 cm3 melanoma located on the dorsal soft palate that virtually occluded the oropharynx. While the complete clinical response of this very large melanoma is striking, the immunological reaction in the tumor and peri-tumor tissue is noteworthy for correlating with the clinical response. It is especially relevant to note the dramatic increase in immune cell infiltration on the final day of treatment in the peri-tumor and 3 weeks posttreatment, in both the tumor and peri-tumor tissue. While there is a complete array of immune cell types in this response, the increase in lymphocytes/monocyte is notable.

In this feasibility, immunopathology, and efficacy study of the treatment of spontaneous canine oral melanoma tumors using HFRT and nanotechnology-based immunotherapy, we demonstrate a significant increase in immune cell infiltration of tumors receiving HFRT with the nanotechnology immune adjuvants, especially the VLP adjuvants. However, the low numbers of patients per treatment arm precludes statistical analysis. The study successfully demonstrates the feasibility, safety, and promising efficacy of these treatments in a highly translatable spontaneous preclinical model.

Specifically, the data enables assessment of changes in cellularity between the pretreatment biopsy and the post-treatment biopsy 14-21 days after treatment completion. There appears to be a preliminary correlation between increased leukocyte concentration in the tumor, (potentially turning an immunologically "cold" tumor into a "hot" tumor), and clinical efficacy. The "RT only" patient had very minimal changes in leukocyte concentration and was the only patient that had metastatic disease at 5 months post-treatment, within the expected time to metastasis of less than 9 months. Treatments that included VLP and/or mNPH all had very clear increases of leukocyte numbers in the tumor due to treatment. The increased leukocyte numbers were accompanied by improvement over the expected outcome with two animals being euthanized tumor free for unrelated clinical reasons 5 months (HFRT+VLP) and 10 months (HFRT+mNPH+VLP) post-treatment, and one dog (HFRT+VLP, FIG. 25) who remains tumor free 20 months after treatment.

The histomorphometric technique used to identify and quantify the immune cell response in the treated tumors is a standard pathological approach requiring histomorphological skills. This approach is very reproducible and accurate for determination of global cellular immune responses in the treated tumor/normal tissue. However, the information it provides is limited from a specific immune cell identification standpoint, and specific immunohistochemical (IHC) labeling will be necessary to define the specific types of cells involved in the immune infiltrate. While appropriate immune cell IHC antibodies are available for many standard immune cell markers in dogs, labeling inconsistencies associated with individual dogs and markers precluded effective use in this study. It should also be noted that the hypofractionated radiation treatment regimen (6×6 Gy over 2 weeks) is not a global clinical standard but is becoming so in a variety of cancer sites, including breast cancer.

TABLE 3

Data Summary from the five patients that are the subject of this study

| Treatment | Patient information | Pretreatment information | Post-treatment cellularity | Patient outcome |
|---|---|---|---|---|
| Hypofractionated radiation | 10 year old, male, Labrador | Tumor 68% lymph/mono 12% PMN 2% stroma 19% | Tumor 55% lymph/mono 15% PMN 4% stroma 26% | Euthanized due to local and metastatic cancer; 5 months post treatment |
| Magnetic nanoparticle hyperthermia | 11 year old, male, Siberian Husky | Tumor 70% lymph/mono 11% PMN 2% stroma 17% | Tumor 26% lymph/mono 18% PMN 18% stroma 38% | Euthanized due to local and metastatic cancer; 26 months post treatment |
| Hypofractionated radiation + virus-like particles | 7 year old, male, Labrador | Tumor 74% lymph/mono 16% PMN 1% stroma 13% | Tumor 18% lymph/mono 21% PMN 13% stroma 48% | Tumor free when euthanized due to GI torsion; 5 months post treatment |
| Hypofractionated radiation + virus-like particles | 12 year old, female Beagle | Tumor 87% lymph/mono 6% PMN 1% stroma 13% | Tumor 29% lymph/mono 45% PMN 9% stroma 17% | Alive and tumor free; 20 months post treatment |
| Hypofractionated radiation + virus-like particles + magnetic nanoparticle hyperthermia | 9 year old, male Rottweiler | Tumor 69% lymph/mono 14% PMN 2% stroma 25% | Tumor 21% lymph/mono 22% PMN 11% stroma 46% | Tumor free when euthanized due to noncancer issue: 10 months post treatment |

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

What is claimed is:

1. A method of treating cancer in a subject in need thereof, the method comprising administering directly to the cancer a therapeutically effective amount of an in situ vaccine, the in situ vaccine comprising at least one of cowpea mosaic virus or cowpea mosaic virus-like particles, wherein the cowpea mosaic virus and cowpea mosaic virus-like particles are not used as a vehicle for drug or antigen delivery, and wherein the subject is a non-human animal.

2. The method of claim 1, wherein the cancer is metastatic cancer.

3. The method of claim 1, wherein the cancer is selected from the group consisting of melanoma, breast cancer, colon cancer, lung cancer, and ovarian cancer.

4. The method of claim 1, wherein the cancer is lung cancer.

5. The method of claim 4, wherein the in situ vaccine is administered by inhalation.

6. The method of claim 1, further comprising the step of ablating the cancer by treating the subject with a therapeutically effective amount of radiotherapy, chemotherapy, high intensity focused ultrasound or immunotherapy.

7. The method of claim 6, wherein the treating by chemotherapy comprises the administration of an anticancer agent to the subject in a therapeutically effective amount.

8. The method of claim 7, wherein the anticancer agent comprises doxorubicin.

9. The method of claim 6, wherein the treating by immunotherapy comprises the administration of monoclonal antibodies to the subject in a therapeutically effective amount.

10. The method of claim 1, wherein the therapeutically effective amount of the in situ vaccine is an amount effective to stimulate a systemic immune response in the subject.

11. The method of claim 1, wherein the cancer is dermal melanoma and the in situ vaccine is administered intratumorally.

12. The method of claim 1, wherein the in situ vaccine comprises cowpea mosaic virus.

13. The method of claim 1, wherein the in situ vaccine comprises cowpea mosaic virus-like particles.

14. The method of claim 1, wherein the in situ vaccine comprises empty cowpea mosaic virus-like particles.

15. The method of claim 1, wherein in situ vaccine comprises cowpea mosaic virus that includes a nucleic acid, and wherein said nucleic acid is RNA.

16. The method of claim 1, wherein the non-human animal is a canine subject.

17. The method of claim 1, wherein the non-human animal is a feline subject.

* * * * *

UNITED STATES PATENT AND TRADEMARK OFFICE
CERTIFICATE OF CORRECTION

PATENT NO. : 11,617,787 B2  
APPLICATION NO. : 16/612214  
DATED : April 4, 2023  
INVENTOR(S) : Steinmetz et al.

Page 1 of 1

It is certified that error appears in the above-identified patent and that said Letters Patent is hereby corrected as shown below:

On the Title Page

Item (71) Applicants: Insert --TRUSTEES OF DARTMOUTH COLLEGE, Hanover, NH (US)-- as the second applicant.

Item (73) Assignees: Insert --TRUSTEES OF DARTMOUTH COLLEGE, Hanover, NH (US)-- as the second assignee.

Signed and Sealed this  
Twenty-first Day of November, 2023

Katherine Kelly Vidal  
*Director of the United States Patent and Trademark Office*